United States Patent [19]

Smart et al.

[11] Patent Number: 5,650,276
[45] Date of Patent: Jul. 22, 1997

[54] MORPHOGENIC PROTEIN SCREENING METHOD

[75] Inventors: John E. Smart, Weston; Hermann Oppermann, Medway; Engin Ozkaynak, Milford; Thangavel Kuberasampath, Medway; David C. Rueger, Hopkinton, all of Mass.; Roy H.L. Pang, Etna, N.H.; Charles M. Cohen, Medway, Mass.

[73] Assignee: Creative BioMolecules, Inc., Hopkinton, Mass.

[21] Appl. No.: 278,729

[22] Filed: Jul. 20, 1994

Related U.S. Application Data

[63] Continuation of Ser. No. 938,021, Aug. 28, 1992, abandoned, which is a continuation-in-part of Ser. No. 752,861, Aug. 30, 1991, abandoned, and Ser. No. 752,764, Aug. 30, 1991, abandoned, which is a continuation-in-part of Ser. No. 752,861, which is a continuation-in-part of Ser. No. 667,274.

[51] Int. Cl.$^6$ .................. C12Q 1/68; C12Q 1/02
[52] U.S. Cl. .......................... 435/6; 435/29
[58] Field of Search ............... 435/4, 6, 240.1, 435/29

[56] References Cited

U.S. PATENT DOCUMENTS

| | | | |
|---|---|---|---|
| 4,968,590 | 11/1990 | Kuberasampath et al. | 530/326 |
| 4,980,281 | 12/1990 | Housey | 435/29 |
| 5,011,691 | 4/1991 | Oppermann et al. | 424/423 |

FOREIGN PATENT DOCUMENTS

| | | |
|---|---|---|
| 8909788 | 10/1989 | WIPO . |
| 8909787 | 10/1989 | WIPO . |
| WO90/00619 | 1/1990 | WIPO . |
| WO91/02744 | 3/1991 | WIPO . |

OTHER PUBLICATIONS

Piqueras et al. (1993), "Localization of Osteogenic Protein-1 (OP-1) mRNA and Protein Expression in Kidney," *J. American Soc. Nephrology* 4(3), 700(A).
Lyons et al., *Genes & Dev.*, vol. 3, 1989, pp. 1657–1668.
Bonewald et al., *Clin. Orthop.*, vol. 250, 1990, pp. 261–276.
Celeste et al., *J. Cell. Bioch.*, vol. 54, p. 105.
Nakayama et al., *FEBS Letters*, vol. 261, 1990, pp. 93–96.
Israel et al., *Growth Factors*, vol. 7, 1992, pp. 139–150.
Boyd (1989) *Cancer Research*, vol. 49, pp. 2427–2432.
Zhou et al., *Journal of Bone and Mineral Research*, vol. 6, No. 7, pp. 767–777, Jul. 1991.
Lee, *Proc. Natl. Acad. Sci. USA*, 88:4250–4254, May 1991.
Reddi (1981), Cell Biology and Biochemistry of Endochondral Bone, Collogen Rel. Res. 1:209–206.
Huggins, The Formation of Bone Under the Influence of Epithelium of the Urinary Tract, (1931, Arch. Surg. 22:377–408).
Urist, Bone Formation by Autoinduction, (1965, Science 150:893–899).

Sampath et al., Bovine Osteogenic Protein is Composed of Dimers of OP-1 and BMP-2A, Two Members of the Transforming Growth Factor-β Superfamily, J. Biol. Chem. 265:13198–13205, 1990.
Reddi et al., Biochemical Sequences in the Transformation of Normal Fibroblasts in Adolescent Rats, Proc. Nat. Aca. Sci. 69:1601–1605 (1972).
Sampath et al., Homology of bone–inductive proteins from human, monkey, bovine, and rat extracellular matrix, Proc. Natl. Acad. Sci. 80:6591–6595, 1983.
Ozkaynak et al., OP–1 cDNA Encodes an Osteogenic Protein in the TGF–β family, EMBO J. 9:2085–2093, (1990).
Panganiban et al., Biochemical Characterization of the Drosphila dpp Protein, a Member of the Transforming Growth Factor β Family of Growth Factors, Mol. Cell. Biol. 10:2669–2677, (1990).
Lyons, et al., Vgr–1, a Mammalian Gene Related to Xenopus Vg–1, is a Member of the Transforming Growth Factor β Gene Superfamily, (1989) PNAS 86:4554–4558.
Chomczynski et al., Single–Step Method of RNA Isolation by Acid Guanidinium Thiocyanate–Phenol–Chloroform Extraction, Anal. Biochem. 162:156–159, 1987.
Rosen et al., An Alternative Method for the Visualization of RNA in Formaldehyde Agarose Gels, Focus, 12:23–24, 1990.
Miller et al., Phenotypic Modulation of the Swarm Rat Chondrosarcoma Induced by Morphogenetic Bone Matrix, Cancer Research, Jul. 1, 1987.
Ozkaynak et al., Murine Osteogenic Protein (OP–1): High Level of mRNA in Kidney, Biochemical and Biophysical Research Communications, Aug. 30, 1991, pp. 116–123.
Wharton et al. (1991) *PNAS* 88:9214–9218.
Von Heijne (1986) *Nucleic Acids Research* 14:4683–4691.
Wozney, et al. (1988) *Science* 242:1528–1534.
Padgett, et al. (1987) *Nature* 325 81–84.
Weeks (1987) *Cell* 51:861–867.
Celeste, et al. (1991) *PNAS* 87:9843–9847.
Celeste, et al. (1990) *PNAS* 87:9843–5847.
Dayoff et al. *Atlas of Protein Sequence and Structure;* vol. 5, Suppl. 3, pp. 345–362, (M.O. Dayoff, ed., Nat'l Biomed. Research Fdn., Washington, D.C. 1979).
Needleman et al. (1970) J. Mol. Biol. 48:443–453.
Wang et al., *PNAS,* 85:9484–9488 (1988).

(List continued on next page.)

*Primary Examiner*—James S. Ketter
*Attorney, Agent, or Firm*—Testa, Hurwitz & Thibeault, LLP

[57] ABSTRACT

Disclosed is a method of screening candidate compounds for the ability to modulate the level of morphogenic protein in mammalian system. The method includes determining a parameter indicative of the level of production of a morphogenic in a cell culture known to produce the morphogen, incubating a candidate compound with the culture for a time sufficient to allow the compound to affect the production of the morphogenic protein, and then assaying the culture again to detect a change in the level of morphogenic protein production.

16 Claims, 3 Drawing Sheets

OTHER PUBLICATIONS

Rosen et al.; Wang et al. and Wozney et al., *Calcified Tissue Int* 42 (Suppl.): A35(136), A37(146,147) 2 Abstracts (1988).

Rosen et al., *Connect Tissue Res*, 20 (1–4):313–9 (1989).

Wozney et al., *Progress In Growth Factor Reserach*, 1:267–280 (1990).

Wang et al., *PNAS*, 87 :2220–2224 (1990).

2 Abstracts Rosen et al., Celeste et al., *J Cell Biochem Suppl.*, 0 (14 Part E): 33(004, 54(105) (1990).

Katagiri et al., *Biochem Biophy Res*, (172(1):295–299 (1990).

Wozney et al., *Journal Of Cell Science Suppl.*, 13:149–156 (1990).

Takuwa et al., *Biochem Biophys Res Comm*, 174(1):96–101 (1991).

Yamaguchi et al., *J Cell Biol*, 113 (3):681–7 (1991).

Abstract Q–105 D'Alessandro et al., *Journal Of Cellular Biochemistry*, (1991).

Abstract Q–111, *Journal Of Cellular Biochemistry*, (1991).

Thies et al., *Endocrinology*, 130 (3):1318–1324 (1992).

Wozney et al., *Mol Reprod Dev*, 32 (2):160–167 (1992).

Rogers et al., *Mol Biol Cell*, 3 (2):189–196 (1992).

3 Abstracts Wozney et al.; Celeste et al.; and Rosen et al., *J Cell Biochem Suppl*, 0 (16 Part F): 76(WO26); 100(W502); 103(W513) (1996).

Israel et al., *Growth Factors*, 7:139–150 (1992).

Padgett et al., *Proc. Natl. Acad. Sci. USA*, 90:2905–2909 (1993).

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label=GENERIC-SEQ-1
        / note= "EACH XAA INDICATES ONE OF THE 20 NATURALLY
        OCCURRING L- ISOMER, ALPHA-AMINO ACIDS, OR A DERIVATIVE
        THEREOF"

( x i ) SEQUENCE DESCRIPTION: SEQ ID NO:1:

```
Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Cys Xaa Xaa Xaa Cys Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Cys Cys Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Cys Xaa Cys
            85                  90                  95

Xaa
```

( 2 ) INFORMATION FOR SEQ ID NO:2:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label=GENERIC-SEQ-2
        / note= "EACH XAA INDICATES ONE OF THE 20 NATURALLY
        OCCURRING L- ISOMER, ALPHA-AMINO ACIDS, OR A DERIVATIVE
        THEREOF"

( x i ) SEQUENCE DESCRIPTION: SEQ ID NO:2:

```
Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Cys Xaa Xaa Xaa Cys Xaa Xaa
                20                  25                  30

Xaa Xaa Xaa Cys Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Cys Cys Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Cys Xaa Cys
            85                  90                  95

Xaa
```

(2) INFORMATION FOR SEQ ID NO:3:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label=GENERIC-SEQ-3
            / note= "WHEREIN EACH XAA IS INDEPENDENTLY SELECTED FROM
            A GROUP OF ONE OR MORE SPECIFIED AMINO ACIDS AS DEFINED
            IN THE SPECIFICATION "

(xi) SEQUENCE DESCRIPTION: SEQ ID NO:3:

```
Leu  Tyr  Val  Xaa  Phe  Xaa  Xaa  Xaa  Gly  Trp  Xaa  Xaa  Trp  Xaa  Xaa  Ala
 1                   5                        10                       15

Pro  Xaa  Gly  Xaa  Xaa  Ala  Xaa  Tyr  Cys  Xaa  Gly  Xaa  Cys  Xaa  Xaa  Pro
               20                  25                       30

Xaa  Xaa  Xaa  Xaa  Xaa  Xaa  Xaa  Xaa  Asn  His  Ala  Xaa  Xaa  Xaa  Xaa  Leu
          35                       40                       45

Xaa  Xaa  Xaa  Xaa  Xaa  Xaa  Xaa  Xaa  Xaa  Xaa  Xaa  Xaa  Cys  Cys  Xaa  Pro
     50                            55                       60

Xaa  Xaa  Xaa  Xaa  Xaa  Xaa  Xaa  Xaa  Leu  Xaa  Xaa  Xaa  Xaa  Xaa  Xaa  Xaa
 65                       70                       75                       80

Val  Xaa  Leu  Xaa  Xaa  Xaa  Xaa  Xaa  Met  Xaa  Val  Xaa  Xaa  Cys  Gly  Cys
               85                       90                       95

Xaa
```

(2) INFORMATION FOR SEQ ID NO:4:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label=GENERIC-SEQ-4
            / note= "WHEREIN EACH XAA IS INDEPENDENTLY SELECTED FROM
            A GROUP OF ONE OR MORE SPECIFIED AMINO ACIDS AS DEFINED
            IN THE SPECIFICATION"

(xi) SEQUENCE DESCRIPTION: SEQ ID NO:4:

```
Cys  Xaa  Xaa  Xaa  Xaa  Leu  Tyr  Val  Xaa  Phe  Xaa  Xaa  Xaa  Gly  Trp  Xaa
 1                   5                        10                       15

Xaa  Trp  Xaa  Xaa  Ala  Pro  Xaa  Gly  Xaa  Xaa  Ala  Xaa  Tyr  Cys  Xaa  Gly
               20                  25                       30

Xaa  Cys  Xaa  Xaa  Pro  Xaa  Xaa  Xaa  Xaa  Xaa  Xaa  Xaa  Xaa  Asn  His  Ala
          35                       40                       45

Xaa  Xaa  Xaa  Xaa  Leu  Xaa  Xaa  Xaa  Xaa  Xaa  Xaa  Xaa  Xaa  Xaa  Xaa  Xaa
     50                            55                       60

Xaa  Cys  Cys  Xaa  Pro  Xaa  Xaa  Xaa  Xaa  Xaa  Xaa  Xaa  Xaa  Leu  Xaa  Xaa
 65                       70                       75                       80

Xaa  Xaa  Xaa  Xaa  Xaa  Val  Xaa  Leu  Xaa  Xaa  Xaa  Xaa  Xaa  Met  Xaa  Val
               85                       90                       95
```

```
             Xaa  Xaa  Cys  Gly  Cys  Xaa
                            100
```

( 2 ) INFORMATION FOR SEQ ID NO:5:

( i ) SEQUENCE CHARACTERISTICS:
        ( A ) LENGTH: 139 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..139
        ( D ) OTHER INFORMATION: /note= "HOP-1 (MATURE FORM)"

( x i ) SEQUENCE DESCRIPTION: SEQ ID NO:5:

```
Ser  Thr  Gly  Ser  Lys  Gln  Arg  Ser  Gln  Asn  Arg  Ser  Lys  Thr  Pro  Lys
 1                  5                        10                       15

Asn  Gln  Glu  Ala  Leu  Arg  Met  Ala  Asn  Val  Ala  Glu  Asn  Ser  Ser  Ser
               20                       25                       30

Asp  Gln  Arg  Gln  Ala  Cys  Lys  Lys  His  Glu  Leu  Tyr  Val  Ser  Phe  Arg
          35                       40                       45

Asp  Leu  Gly  Trp  Gln  Asp  Trp  Ile  Ile  Ala  Pro  Glu  Gly  Tyr  Ala  Ala
     50                       55                       60

Tyr  Tyr  Cys  Glu  Gly  Glu  Cys  Ala  Phe  Pro  Leu  Asn  Ser  Tyr  Met  Asn
65                       70                       75                       80

Ala  Thr  Asn  His  Ala  Ile  Val  Gln  Thr  Leu  Val  His  Phe  Ile  Asn  Pro
               85                       90                       95

Glu  Thr  Val  Pro  Lys  Pro  Cys  Cys  Ala  Pro  Thr  Gln  Leu  Asn  Ala  Ile
               100                      105                      110

Ser  Val  Leu  Tyr  Phe  Asp  Asp  Ser  Ser  Asn  Val  Ile  Leu  Lys  Lys  Tyr
               115                      120                      125

Arg  Asn  Met  Val  Val  Arg  Ala  Cys  Gly  Cys  His
          130                      135
```

( 2 ) INFORMATION FOR SEQ ID NO:6:

( i ) SEQUENCE CHARACTERISTICS:
        ( A ) LENGTH: 139 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..139
        ( D ) OTHER INFORMATION: /note= "MOP-1 (MATURE FORM)"

( x i ) SEQUENCE DESCRIPTION: SEQ ID NO:6:

```
Ser  Thr  Gly  Gly  Lys  Gln  Arg  Ser  Gln  Asn  Arg  Ser  Lys  Thr  Pro  Lys
 1                  5                        10                       15

Asn  Gln  Glu  Ala  Leu  Arg  Met  Ala  Ser  Val  Ala  Glu  Asn  Ser  Ser  Ser
               20                       25                       30

Asp  Gln  Arg  Gln  Ala  Cys  Lys  Lys  His  Glu  Leu  Tyr  Val  Ser  Phe  Arg
          35                       40                       45

Asp  Leu  Gly  Trp  Gln  Asp  Trp  Ile  Ile  Ala  Pro  Glu  Gly  Tyr  Ala  Ala
     50                       55                       60

Tyr  Tyr  Cys  Glu  Gly  Glu  Cys  Ala  Phe  Pro  Leu  Asn  Ser  Tyr  Met  Asn
```

|  |  |  | 65 |  |  |  | 70 |  |  |  | 75 |  |  |  | 80 |

Ala Thr Asn His Ala Ile Val Gln Thr Leu Val His Phe Ile Asn Pro
                    85              90              95

Asp Thr Val Pro Lys Pro Cys Cys Ala Pro Thr Gln Leu Asn Ala Ile
                100             105             110

Ser Val Leu Tyr Phe Asp Asp Ser Ser Asn Val Ile Leu Lys Lys Tyr
            115             120             125

Arg Asn Met Val Val Arg Ala Cys Gly Cys His
    130             135

( 2 ) INFORMATION FOR SEQ ID NO:7:

( i ) SEQUENCE CHARACTERISTICS:
        ( A ) LENGTH: 139 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..139
        ( D ) OTHER INFORMATION: /note= "HOP-2 (MATURE FORM)"

( x i ) SEQUENCE DESCRIPTION: SEQ ID NO:7:

Ala Val Arg Pro Leu Arg Arg Arg Gln Pro Lys Lys Ser Asn Glu Leu
1               5               10              15

Pro Gln Ala Asn Arg Leu Pro Gly Ile Phe Asp Asp Val His Gly Ser
            20              25              30

His Gly Arg Gln Val Cys Arg Arg His Glu Leu Tyr Val Ser Phe Gln
        35              40              45

Asp Leu Gly Trp Leu Asp Trp Val Ile Ala Pro Gln Gly Tyr Ser Ala
    50              55              60

Tyr Tyr Cys Glu Gly Glu Cys Ser Phe Pro Leu Asp Ser Cys Met Asn
65              70              75              80

Ala Thr Asn His Ala Ile Leu Gln Ser Leu Val His Leu Met Lys Pro
                85              90              95

Asn Ala Val Pro Lys Ala Cys Cys Ala Pro Thr Lys Leu Ser Ala Thr
                100             105             110

Ser Val Leu Tyr Tyr Asp Ser Ser Asn Asn Val Ile Leu Arg Lys His
            115             120             125

Arg Asn Met Val Val Lys Ala Cys Gly Cys His
    130             135

( 2 ) INFORMATION FOR SEQ ID NO:8:

( i ) SEQUENCE CHARACTERISTICS:
        ( A ) LENGTH: 139 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..139
        ( D ) OTHER INFORMATION: /note= "MOP-2 (MATURE FORM)"

( x i ) SEQUENCE DESCRIPTION: SEQ ID NO:8:

Ala Ala Arg Pro Leu Lys Arg Arg Gln Pro Lys Lys Thr Asn Glu Leu
1               5               10              15

-continued

```
Pro His Pro Asn Lys Leu Pro Gly Ile Phe Asp Asp Gly His Gly Ser
        20              25              30

Arg Gly Arg Glu Val Cys Arg Arg His Glu Leu Tyr Val Ser Phe Arg
        35              40              45

Asp Leu Gly Trp Leu Asp Trp Val Ile Ala Pro Gln Gly Tyr Ser Ala
        50              55              60

Tyr Tyr Cys Glu Gly Glu Cys Ala Phe Pro Leu Asp Ser Cys Met Asn
65                      70              75                      80

Ala Thr Asn His Ala Ile Leu Gln Ser Leu Val His Leu Met Lys Pro
                85              90                      95

Asp Val Val Pro Lys Ala Cys Cys Ala Pro Thr Lys Leu Ser Ala Thr
        100             105                     110

Ser Val Leu Tyr Tyr Asp Ser Ser Asn Asn Val Ile Leu Arg Lys His
        115             120                     125

Arg Asn Met Val Val Lys Ala Cys Gly Cys His
        130             135
```

(2) INFORMATION FOR SEQ ID NO:9:

(i) SEQUENCE CHARACTERISTICS:
    (A) LENGTH: 101 amino acids
    (B) TYPE: amino acid
    (C) STRANDEDNESS: single
    (D) TOPOLOGY: linear (ii) MOLECULE TYPE: protein (ix) FEATURE:
    (A) NAME/KEY: Protein
    (B) LOCATION: 1..101
    (D) OTHER INFORMATION: /note= "CBMP-2A(FX)"

(xi) SEQUENCE DESCRIPTION: SEQ ID NO:9:

```
Cys Lys Arg His Pro Leu Tyr Val Asp Phe Ser Asp Val Gly Trp Asn
1               5               10                      15

Asp Trp Ile Val Ala Pro Pro Gly Tyr His Ala Phe Tyr Cys His Gly
        20              25              30

Glu Cys Pro Phe Pro Leu Ala Asp His Leu Asn Ser Thr Asn His Ala
        35              40              45

Ile Val Gln Thr Leu Val Asn Ser Val Asn Ser Lys Ile Pro Lys Ala
        50              55              60

Cys Cys Val Pro Thr Glu Leu Ser Ala Ile Ser Met Leu Tyr Leu Asp
65              70                      75                      80

Glu Asn Glu Lys Val Val Leu Lys Asn Tyr Gln Asp Met Val Val Glu
                85                      90              95

Gly Cys Gly Cys Arg
                100
```

(2) INFORMATION FOR SEQ ID NO:10:

(i) SEQUENCE CHARACTERISTICS:
    (A) LENGTH: 101 amino acids
    (B) TYPE: amino acid
    (C) STRANDEDNESS: single
    (D) TOPOLOGY: linear (ii) MOLECULE TYPE: protein (ix) FEATURE:
    (A) NAME/KEY: Protein
    (B) LOCATION: 1..101
    (D) OTHER INFORMATION: /note= "CBMP-2B(FX)"

(xi) SEQUENCE DESCRIPTION: SEQ ID NO:10:

```
Cys Arg Arg His Ser Leu Tyr Val Asp Phe Ser Asp Val Gly Trp Asn
 1               5                  10                  15

Asp Trp Ile Val Ala Pro Pro Gly Tyr Gln Ala Phe Tyr Cys His Gly
            20                  25                  30

Asp Cys Pro Phe Pro Leu Ala Asp His Leu Asn Ser Thr Asn His Ala
        35                  40                  45

Ile Val Gln Thr Leu Val Asn Ser Val Asn Ser Ser Ile Pro Lys Ala
        50                  55                  60

Cys Cys Val Pro Thr Glu Leu Ser Ala Ile Ser Met Leu Tyr Leu Asp
 65                  70                  75                  80

Glu Tyr Asp Lys Val Val Leu Lys Asn Tyr Gln Glu Met Val Val Glu
                85                  90                  95

Gly Cys Gly Cys Arg
            100
```

(2) INFORMATION FOR SEQ ID NO:11:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /note= "DPP(FX)"

(xi) SEQUENCE DESCRIPTION: SEQ ID NO:11:

```
Cys Arg Arg His Ser Leu Tyr Val Asp Phe Ser Asp Val Gly Trp Asp
 1               5                  10                  15

Asp Trp Ile Val Ala Pro Leu Gly Tyr Asp Ala Tyr Tyr Cys His Gly
            20                  25                  30

Lys Cys Pro Phe Pro Leu Ala Asp His Phe Asn Ser Thr Asn His Ala
        35                  40                  45

Val Val Gln Thr Leu Val Asn Asn Asn Asn Pro Gly Lys Val Pro Lys
        50                  55                  60

Ala Cys Cys Val Pro Thr Gln Leu Asp Ser Val Ala Met Leu Tyr Leu
 65                  70                  75                  80

Asn Asp Gln Ser Thr Val Val Leu Lys Asn Tyr Gln Glu Met Thr Val
                85                  90                  95

Val Gly Cys Gly Cys Arg
            100
```

(2) INFORMATION FOR SEQ ID NO:12:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /note= "VGL(FX)"

(xi) SEQUENCE DESCRIPTION: SEQ ID NO:12:

```
Cys Lys Lys Arg His Leu Tyr Val Glu Phe Lys Asp Val Gly Trp Gln
```

|   |   |   |   | 1 |   |   |   |   | 5 |   |   |   |   | 10 |   |   |   |   | 15 |
|---|---|---|---|---|---|---|---|---|---|---|---|---|---|---|---|---|---|---|---|

Asn Trp Val Ile Ala Pro Gln Gly Tyr Met Ala Asn Tyr Cys Tyr Gly
               20                  25                30

Glu Cys Pro Tyr Pro Leu Thr Glu Ile Leu Asn Gly Ser Asn His Ala
        35                  40                45

Ile Leu Gln Thr Leu Val His Ser Ile Glu Pro Glu Asp Ile Pro Leu
    50                 55               60

Pro Cys Cys Val Pro Thr Lys Met Ser Pro Ile Ser Met Leu Phe Tyr
65                     70               75              80

Asp Asn Asn Asp Asn Val Val Leu Arg His Tyr Glu Asn Met Ala Val
               85                  90              95

Asp Glu Cys Gly Cys Arg
            100

( 2 ) INFORMATION FOR SEQ ID NO:13:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /note= "VGR-1(FX)"

( x i ) SEQUENCE DESCRIPTION: SEQ ID NO:13:

Cys Lys Lys His Glu Leu Tyr Val Ser Phe Gln Asp Val Gly Trp Gln
1                    5                   10               15

Asp Trp Ile Ile Ala Pro Lys Gly Tyr Ala Ala Asn Tyr Cys Asp Gly
               20                  25                30

Glu Cys Ser Phe Pro Leu Asn Ala His Met Asn Ala Thr Asn His Ala
        35                  40                45

Ile Val Gln Thr Leu Val His Val Met Asn Pro Glu Tyr Val Pro Lys
    50                 55               60

Pro Cys Cys Ala Pro Thr Lys Val Asn Ala Ile Ser Val Leu Tyr Phe
65                     70               75              80

Asp Asp Asn Ser Asn Val Ile Leu Lys Lys Tyr Arg Asn Met Val Val
               85                  90              95

Arg Ala Cys Gly Cys His
            100

( 2 ) INFORMATION FOR SEQ ID NO:14:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..106
        ( D ) OTHER INFORMATION: /note= "GDF-1 (FX)"

( x i ) SEQUENCE DESCRIPTION: SEQ ID NO:14:

Cys Arg Ala Arg Arg Leu Tyr Val Ser Phe Arg Glu Val Gly Trp His
1                    5                   10               15

```
        Arg  Trp  Val  Ile  Ala  Pro  Arg  Gly  Phe  Leu  Ala  Asn  Tyr  Cys  Gln  Gly
                       20                      25                           30

Gln  Cys  Ala  Leu  Pro  Val  Ala  Leu  Ser  Gly  Ser  Gly  Gly  Pro  Pro  Ala
                  35                      40                      45

Leu  Asn  His  Ala  Val  Leu  Arg  Ala  Leu  Met  His  Ala  Ala  Ala  Pro  Gly
             50                      55                      60

Ala  Ala  Asp  Leu  Pro  Cys  Cys  Val  Pro  Ala  Arg  Leu  Ser  Pro  Ile  Ser
        65                      70                      75                           80

Val  Leu  Phe  Phe  Asp  Asn  Ser  Asp  Asn  Val  Val  Leu  Arg  Gln  Tyr  Glu
                            85                      90                           95

Asp  Met  Val  Val  Asp  Glu  Cys  Gly  Cys  Arg
                       100                     105
```

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
        Cys  Xaa  Xaa  Xaa  Xaa
        1                    5
```

( 2 ) INFORMATION FOR SEQ ID NO:16:

( i ) SEQUENCE CHARACTERISTICS:
        ( A ) LENGTH: 1822 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 49..1341
        ( D ) OTHER INFORMATION: /product="HOP-1"

( x i ) SEQUENCE DESCRIPTION: SEQ ID NO:16:

```
GGTGCGGGCC  CGGAGCCCGG  AGCCCGGGTA  GCGCGTAGAG  CCGGCGCG ATG CAC GTG          57
                                                        Met His Val
                                                        1

CGC TCA CTG CGA GCT GCG GCG CCG CAC AGC TTC GTG GCG CTC TGG GCA             105
Arg Ser Leu Arg Ala Ala Ala Pro His Ser Phe Val Ala Leu Trp Ala
    5                   10                  15

CCC CTG TTC CTG CTG CGC TCC GCC CTG GCC GAC TTC AGC CTG GAC AAC             153
Pro Leu Phe Leu Leu Arg Ser Ala Leu Ala Asp Phe Ser Leu Asp Asn
20                  25                  30                  35

GAG GTG CAC TCG AGC TTC ATC CAC CGG GCG CTC CGC AGC CAG GAG CGG             201
Glu Val His Ser Ser Phe Ile His Arg Arg Leu Arg Ser Gln Glu Arg
                40                  45                  50

CGG GAG ATG CAG CGC GAG ATC CTC TCC ATT TTG GGC TTG CCC CAC CGC             249
Arg Glu Met Gln Arg Glu Ile Leu Ser Ile Leu Gly Leu Pro His Arg
                55                  60                  65

CCG CGC CCG CAC CTC CAG GGC AAG CAC AAC TCG GCA CCC ATG TTC ATG             297
Pro Arg Pro His Leu Gln Gly Lys His Asn Ser Ala Pro Met Phe Met
            70                  75                  80

CTG GAC CTG TAC AAC GCC ATG GCG GTG GAG GAG GGC GGC GGG CCC GGC             345
Leu Asp Leu Tyr Asn Ala Met Ala Val Glu Glu Gly Gly Gly Pro Gly
        85                  90                  95
```

```
GGC CAG GGC TTC TCC TAC CCC TAC AAG GCC GTC TTC AGT ACC CAG GGC    393
Gly Gln Gly Phe Ser Tyr Pro Tyr Lys Ala Val Phe Ser Thr Gln Gly
100             105                 110                 115

CCC CCT CTG GCC AGC CTG CAA GAT AGC CAT TTC CTC ACC GAC GCC GAC    441
Pro Pro Leu Ala Ser Leu Gln Asp Ser His Phe Leu Thr Asp Ala Asp
                120                 125                 130

ATG GTC ATG AGC TTC GTC AAC CTC GTG GAA CAT GAC AAG GAA TTC TTC    489
Met Val Met Ser Phe Val Asn Leu Val Glu His Asp Lys Glu Phe Phe
            135                 140                 145

CAC CCA CGC TAC CAC CAT CGA GAG TTC CGG TTT GAT CTT TCC AAG ATC    537
His Pro Arg Tyr His His Arg Glu Phe Arg Phe Asp Leu Ser Lys Ile
        150                 155                 160

CCA GAA GGG GAA GCT GTC ACG GCA GCC GAA TTC CGG ATC TAC AAG GAC    585
Pro Glu Gly Glu Ala Val Thr Ala Ala Glu Phe Arg Ile Tyr Lys Asp
165                 170                 175

TAC ATC CGG GAA CGC TTC GAC AAT GAG ACG TTC CGG ATC AGC GTT TAT    633
Tyr Ile Arg Glu Arg Phe Asp Asn Glu Thr Phe Arg Ile Ser Val Tyr
180                 185                 190                 195

CAG GTG CTC CAG GAG CAC TTG GGC AGG GAA TCG GAT CTC TTC CTG CTC    681
Gln Val Leu Gln Glu His Leu Gly Arg Glu Ser Asp Leu Phe Leu Leu
                200                 205                 210

GAC AGC CGT ACC CTC TGG GCC TCG GAG GAG GGC TGG CTG GTG TTT GAC    729
Asp Ser Arg Thr Leu Trp Ala Ser Glu Glu Gly Trp Leu Val Phe Asp
            215                 220                 225

ATC ACA GCC ACC AGC AAC CAC TGG GTG GTC AAT CCG CGG CAC AAC CTG    777
Ile Thr Ala Thr Ser Asn His Trp Val Val Asn Pro Arg His Asn Leu
        230                 235                 240

GGC CTG CAG CTC TCG GTG GAG ACG CTG GAT GGG CAG AGC ATC AAC CCC    825
Gly Leu Gln Leu Ser Val Glu Thr Leu Asp Gly Gln Ser Ile Asn Pro
245                 250                 255

AAG TTG GCG GGC CTG ATT GGG CGG CAC GGG CCC CAG AAC AAG CAG CCC    873
Lys Leu Ala Gly Leu Ile Gly Arg His Gly Pro Gln Asn Lys Gln Pro
260                 265                 270                 275

TTC ATG GTG GCT TTC TTC AAG GCC ACG GAG GTC CAC TTC CGC AGC ATC    921
Phe Met Val Ala Phe Phe Lys Ala Thr Glu Val His Phe Arg Ser Ile
                280                 285                 290

CGG TCC ACG GGG AGC AAA CAG CGC AGC CAG AAC CGC TCC AAG ACG CCC    969
Arg Ser Thr Gly Ser Lys Gln Arg Ser Gln Asn Arg Ser Lys Thr Pro
            295                 300                 305

AAG AAC CAG GAA GCC CTG CGG ATG GCC AAC GTG GCA GAG AAC AGC AGC   1017
Lys Asn Gln Glu Ala Leu Arg Met Ala Asn Val Ala Glu Asn Ser Ser
        310                 315                 320

AGC GAC CAG AGG CAG GCC TGT AAG AAG CAC GAG CTG TAT GTC AGC TTC   1065
Ser Asp Gln Arg Gln Ala Cys Lys Lys His Glu Leu Tyr Val Ser Phe
        325                 330                 335

CGA GAC CTG GGC TGG CAG GAC TGG ATC ATC GCG CCT GAA GGC TAC GCC   1113
Arg Asp Leu Gly Trp Gln Asp Trp Ile Ile Ala Pro Glu Gly Tyr Ala
340                 345                 350                 355

GCC TAC TAC TGT GAG GGG GAG TGT GCC TTC CCT CTG AAC TCC TAC ATG   1161
Ala Tyr Tyr Cys Glu Gly Glu Cys Ala Phe Pro Leu Asn Ser Tyr Met
                360                 365                 370

AAC GCC ACC AAC CAC GCC ATC GTG CAG ACG CTG GTC CAC TTC ATC AAC   1209
Asn Ala Thr Asn His Ala Ile Val Gln Thr Leu Val His Phe Ile Asn
            375                 380                 385

CCG GAA ACG GTG CCC AAG CCC TGC TGT GCG CCC ACG CAG CTC AAT GCC   1257
Pro Glu Thr Val Pro Lys Pro Cys Cys Ala Pro Thr Gln Leu Asn Ala
        390                 395                 400

ATC TCC GTC CTC TAC TTC GAT GAC AGC TCC AAC GTC ATC CTG AAG AAA   1305
Ile Ser Val Leu Tyr Phe Asp Asp Ser Ser Asn Val Ile Leu Lys Lys
        405                 410                 415
```

```
TAC AGA AAC ATG GTG GTC CGG GCC TGT GGC TGC CAC TAGCTCCTCC        1351
Tyr Arg Asn Met Val Val Arg Ala Cys Gly Cys His
420             425                 430

GAGAATTCAG ACCCTTTGGG GCCAAGTTTT TCTGGATCCT CCATTGCTCG CCTTGGCCAG 1411

GAACCAGCAG ACCAACTGCC TTTTGTGAGA CCTTCCCCTC CCTATCCCCA ACTTTAAAGG 1471

TGTGAGAGTA TTAGGAAACA TGAGCAGCAT ATGGCTTTTG ATCAGTTTTT CAGTGGCAGC 1531

ATCCAATGAA CAAGATCCTA CAAGCTGTGC AGGCAAAACC TAGCAGGAAA AAAAACAAC  1591

GCATAAAGAA AAATGGCCGG GCCAGGTCAT TGGCTGGGAA GTCTCAGCCA TGCACGGACT 1651

CGTTTCCAGA GGTAATTATG AGCGCCTACC AGCCAGGCCA CCCAGCCGTG GGAGGAAGGG 1711

GGCGTGGCAA GGGGTGGGCA CATTGGTGTC TGTGCGAAAG GAAAATTGAC CCGGAAGTTC 1771

CTGTAATAAA TGTCACAATA AAACGAATGA ATGAAAAAAA AAAAAAAAA A           1822
```

( 2 ) INFORMATION FOR SEQ ID NO:17:

( i ) SEQUENCE CHARACTERISTICS:
    ( A ) LENGTH: 431 amino acids
    ( B ) TYPE: amino acid
    ( D ) TOPOLOGY: linear ( i i ) MOLECULE TYPE: protein ( x i ) SEQUENCE DESCRIPTION: SEQ ID NO:17:

```
Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
            20              25                  30

Leu Asp Asn Glu Val His Ser Ser Phe Ile His Arg Arg Leu Arg Ser
        35              40                  45

Gln Glu Arg Arg Glu Met Gln Arg Glu Ile Leu Ser Ile Leu Gly Leu
    50              55                  60

Pro His Arg Pro Arg Pro His Leu Gln Gly Lys His Asn Ser Ala Pro
65              70              75                      80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100             105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255
```

| | | | | | | | | | | | | | | |
|---|---|---|---|---|---|---|---|---|---|---|---|---|---|---|
| Ile | Asn | Pro | Lys 260 | Leu | Ala | Gly | Leu | Ile 265 | Gly | Arg | His | Gly | Pro 270 | Gln | Asn |
| Lys | Gln | Pro 275 | Phe | Met | Val | Ala | Phe 280 | Phe | Lys | Ala | Thr | Glu 285 | Val | His | Phe |
| Arg | Ser | Ile | Arg | Ser | Thr | Gly | Ser | Lys | Gln | Arg | Ser | Gln | Asn | Arg | Ser |
| | 290 | | | | | 295 | | | | | 300 | | | | |
| Lys | Thr | Pro | Lys | Asn | Gln | Glu | Ala | Leu | Arg | Met | Ala | Asn | Val | Ala | Glu |
| 305 | | | | | 310 | | | | | 315 | | | | | 320 |
| Asn | Ser | Ser | Ser | Asp | Gln | Arg | Gln | Ala | Cys | Lys | Lys | His | Glu | Leu | Tyr |
| | | | | 325 | | | | | 330 | | | | | 335 | |
| Val | Ser | Phe | Arg | Asp | Leu | Gly | Trp | Gln | Asp | Trp | Ile | Ile | Ala | Pro | Glu |
| | | | 340 | | | | | 345 | | | | | 350 | | |
| Gly | Tyr | Ala | Ala | Tyr | Tyr | Cys | Glu | Gly | Glu | Cys | Ala | Phe | Pro | Leu | Asn |
| | | | 355 | | | | | 360 | | | | | 365 | | |
| Ser | Tyr | Met | Asn | Ala | Thr | Asn | His | Ala | Ile | Val | Gln | Thr | Leu | Val | His |
| | | 370 | | | | | 375 | | | | | 380 | | | |
| Phe | Ile | Asn | Pro | Glu | Thr | Val | Pro | Lys | Pro | Cys | Cys | Ala | Pro | Thr | Gln |
| 385 | | | | | 390 | | | | | 395 | | | | | 400 |
| Leu | Asn | Ala | Ile | Ser | Val | Leu | Tyr | Phe | Asp | Asp | Ser | Ser | Asn | Val | Ile |
| | | | | 405 | | | | | 410 | | | | | 415 | |
| Leu | Lys | Lys | Tyr | Arg | Asn | Met | Val | Val | Arg | Ala | Cys | Gly | Cys | His | |
| | | | 420 | | | | | 425 | | | | | 430 | | |

( 2 ) INFORMATION FOR SEQ ID NO:18:

( i ) SEQUENCE CHARACTERISTICS:
( A ) LENGTH: 1873 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 104..1393
( D ) OTHER INFORMATION: /product="MOP1 (CDNA)"

( x i ) SEQUENCE DESCRIPTION: SEQ ID NO:18:

```
CTGCAGCAAG TGACCTCGGG TCGTGGACCG CTGCCCTGCC CCCTCCGCTG CCACCTGGGG        60

CGGCGCGGGC CCGGTGCCCC GGATCGCGCG TAGAGCCGGC GCG ATG CAC GTG CGC        115
                                              Met His Val Arg
                                               1

TCG CTG CGC GCT GCG GCG CCA CAC AGC TTC GTG GCG CTC TGG GCG CCT        163
Ser Leu Arg Ala Ala Ala Pro His Ser Phe Val Ala Leu Trp Ala Pro
  5              10                  15                  20

CTG TTC TTG CTG CGC TCC GCC CTG GCC GAT TTC AGC CTG GAC AAC GAG        211
Leu Phe Leu Leu Arg Ser Ala Leu Ala Asp Phe Ser Leu Asp Asn Glu
                25                  30                  35

GTG CAC TCC AGC TTC ATC CAC CGG CGC CTC CGC AGC CAG GAG CGG CGG        259
Val His Ser Ser Phe Ile His Arg Arg Leu Arg Ser Gln Glu Arg Arg
            40                  45                  50

GAG ATG CAG CGG GAG ATC CTG TCC ATC TTA GGG TTG CCC CAT CGC CCG        307
Glu Met Gln Arg Glu Ile Leu Ser Ile Leu Gly Leu Pro His Arg Pro
         55                  60                  65

CGC CCG CAC CTC CAG GGA AAG CAT AAT TCG GCC CCC ATG TTC ATG TTG        355
Arg Pro His Leu Gln Gly Lys His Asn Ser Ala Pro Met Phe Met Leu
     70                  75                  80

GAC CTG TAC AAC GCC ATG GCG GTG GAG GAG AGC GGG CCG GAC GGA CAG        403
```

-continued

| | | | | | | | | | | | | | | | | |
|---|---|---|---|---|---|---|---|---|---|---|---|---|---|---|---|---|
| | Asp | Leu | Tyr | Asn | Ala | Met | Ala | Val | Glu | Glu | Ser | Gly | Pro | Asp | Gly | Gln |
| | 85 | | | | 90 | | | | | 95 | | | | | 100 | |

| GGC | TTC | TCC | TAC | CCC | TAC | AAG | GCC | GTC | TTC | AGT | ACC | CAG | GGC | CCC | CCT | 451 |
|---|---|---|---|---|---|---|---|---|---|---|---|---|---|---|---|---|
| Gly | Phe | Ser | Tyr | Pro | Tyr | Lys | Ala | Val | Phe | Ser | Thr | Gln | Gly | Pro | Pro | |
| | | | | 105 | | | | | 110 | | | | | 115 | | |

| TTA | GCC | AGC | CTG | CAG | GAC | AGC | CAT | TTC | CTC | ACT | GAC | GCC | GAC | ATG | GTC | 499 |
|---|---|---|---|---|---|---|---|---|---|---|---|---|---|---|---|---|
| Leu | Ala | Ser | Leu | Gln | Asp | Ser | His | Phe | Leu | Thr | Asp | Ala | Asp | Met | Val | |
| | | | 120 | | | | | 125 | | | | | 130 | | | |

| ATG | AGC | TTC | GTC | AAC | CTA | GTG | GAA | CAT | GAC | AAA | GAA | TTC | TTC | CAC | CCT | 547 |
|---|---|---|---|---|---|---|---|---|---|---|---|---|---|---|---|---|
| Met | Ser | Phe | Val | Asn | Leu | Val | Glu | His | Asp | Lys | Glu | Phe | Phe | His | Pro | |
| | | | 135 | | | | | 140 | | | | | 145 | | | |

| CGA | TAC | CAC | CAT | CGG | GAG | TTC | CGG | TTT | GAT | CTT | TCC | AAG | ATC | CCC | GAG | 595 |
|---|---|---|---|---|---|---|---|---|---|---|---|---|---|---|---|---|
| Arg | Tyr | His | His | Arg | Glu | Phe | Arg | Phe | Asp | Leu | Ser | Lys | Ile | Pro | Glu | |
| | | 150 | | | | | 155 | | | | | 160 | | | | |

| GGC | GAA | CGG | GTG | ACC | GCA | GCC | GAA | TTC | AGG | ATC | TAT | AAG | GAC | TAC | ATC | 643 |
|---|---|---|---|---|---|---|---|---|---|---|---|---|---|---|---|---|
| Gly | Glu | Arg | Val | Thr | Ala | Ala | Glu | Phe | Arg | Ile | Tyr | Lys | Asp | Tyr | Ile | |
| 165 | | | | | 170 | | | | | 175 | | | | | 180 | |

| CGG | GAG | CGA | TTT | GAC | AAC | GAG | ACC | TTC | CAG | ATC | ACA | GTC | TAT | CAG | GTG | 691 |
|---|---|---|---|---|---|---|---|---|---|---|---|---|---|---|---|---|
| Arg | Glu | Arg | Phe | Asp | Asn | Glu | Thr | Phe | Gln | Ile | Thr | Val | Tyr | Gln | Val | |
| | | | | 185 | | | | | 190 | | | | | 195 | | |

| CTC | CAG | GAG | CAC | TCA | GGC | AGG | GAG | TCG | GAC | CTC | TTC | TTG | CTG | GAC | AGC | 739 |
|---|---|---|---|---|---|---|---|---|---|---|---|---|---|---|---|---|
| Leu | Gln | Glu | His | Ser | Gly | Arg | Glu | Ser | Asp | Leu | Phe | Leu | Leu | Asp | Ser | |
| | | | 200 | | | | | 205 | | | | | 210 | | | |

| CGC | ACC | ATC | TGG | GCT | TCT | GAG | GAG | GGC | TGG | TTG | GTG | TTT | GAT | ATC | ACA | 787 |
|---|---|---|---|---|---|---|---|---|---|---|---|---|---|---|---|---|
| Arg | Thr | Ile | Trp | Ala | Ser | Glu | Glu | Gly | Trp | Leu | Val | Phe | Asp | Ile | Thr | |
| | | 215 | | | | | 220 | | | | | 225 | | | | |

| GCC | ACC | AGC | AAC | CAC | TGG | GTG | GTC | AAC | CCT | CGG | CAC | AAC | CTG | GGC | TTA | 835 |
|---|---|---|---|---|---|---|---|---|---|---|---|---|---|---|---|---|
| Ala | Thr | Ser | Asn | His | Trp | Val | Val | Asn | Pro | Arg | His | Asn | Leu | Gly | Leu | |
| | 230 | | | | | 235 | | | | | 240 | | | | | |

| CAG | CTC | TCT | GTG | GAG | ACC | CTG | GAT | GGG | CAG | AGC | ATC | AAC | CCC | AAG | TTG | 883 |
|---|---|---|---|---|---|---|---|---|---|---|---|---|---|---|---|---|
| Gln | Leu | Ser | Val | Glu | Thr | Leu | Asp | Gly | Gln | Ser | Ile | Asn | Pro | Lys | Leu | |
| 245 | | | | | 250 | | | | | 255 | | | | | 260 | |

| GCA | GGC | CTG | ATT | GGA | CGG | CAT | GGA | CCC | CAG | AAC | AAG | CAA | CCC | TTC | ATG | 931 |
|---|---|---|---|---|---|---|---|---|---|---|---|---|---|---|---|---|
| Ala | Gly | Leu | Ile | Gly | Arg | His | Gly | Pro | Gln | Asn | Lys | Gln | Pro | Phe | Met | |
| | | | | 265 | | | | | 270 | | | | | 275 | | |

| GTG | GCC | TTC | TTC | AAG | GCC | ACG | GAA | GTC | CAT | CTC | CGT | AGT | ATC | CGG | TCC | 979 |
|---|---|---|---|---|---|---|---|---|---|---|---|---|---|---|---|---|
| Val | Ala | Phe | Phe | Lys | Ala | Thr | Glu | Val | His | Leu | Arg | Ser | Ile | Arg | Ser | |
| | | | 280 | | | | | 285 | | | | | 290 | | | |

| ACG | GGG | GGC | AAG | CAG | CGC | AGC | CAG | AAT | CGC | TCC | AAG | ACG | CCA | AAG | AAC | 1027 |
|---|---|---|---|---|---|---|---|---|---|---|---|---|---|---|---|---|
| Thr | Gly | Gly | Lys | Gln | Arg | Ser | Gln | Asn | Arg | Ser | Lys | Thr | Pro | Lys | Asn | |
| | | 295 | | | | | 300 | | | | | 305 | | | | |

| CAA | GAG | GCC | CTG | AGG | ATG | GCC | AGT | GTG | GCA | GAA | AAC | AGC | AGC | AGT | GAC | 1075 |
|---|---|---|---|---|---|---|---|---|---|---|---|---|---|---|---|---|
| Gln | Glu | Ala | Leu | Arg | Met | Ala | Ser | Val | Ala | Glu | Asn | Ser | Ser | Ser | Asp | |
| | 310 | | | | | 315 | | | | | 320 | | | | | |

| CAG | AGG | CAG | GCC | TGC | AAG | AAA | CAT | GAG | CTG | TAC | GTC | AGC | TTC | CGA | GAC | 1123 |
|---|---|---|---|---|---|---|---|---|---|---|---|---|---|---|---|---|
| Gln | Arg | Gln | Ala | Cys | Lys | Lys | His | Glu | Leu | Tyr | Val | Ser | Phe | Arg | Asp | |
| 325 | | | | 330 | | | | | 335 | | | | | 340 | | |

| CTT | GGC | TGG | CAG | GAC | TGG | ATC | ATT | GCA | CCT | GAA | GGC | TAT | GCT | GCC | TAC | 1171 |
|---|---|---|---|---|---|---|---|---|---|---|---|---|---|---|---|---|
| Leu | Gly | Trp | Gln | Asp | Trp | Ile | Ile | Ala | Pro | Glu | Gly | Tyr | Ala | Ala | Tyr | |
| | | | | 345 | | | | | 350 | | | | | 355 | | |

| TAC | TGT | GAG | GGA | GAG | TGC | GCC | TTC | CCT | CTG | AAC | TCC | TAC | ATG | AAC | GCC | 1219 |
|---|---|---|---|---|---|---|---|---|---|---|---|---|---|---|---|---|
| Tyr | Cys | Glu | Gly | Glu | Cys | Ala | Phe | Pro | Leu | Asn | Ser | Tyr | Met | Asn | Ala | |
| | | | 360 | | | | | 365 | | | | | 370 | | | |

| ACC | AAC | CAC | GCC | ATC | GTC | CAG | ACA | CTG | GTT | CAC | TTC | ATC | AAC | CCA | GAC | 1267 |
|---|---|---|---|---|---|---|---|---|---|---|---|---|---|---|---|---|
| Thr | Asn | His | Ala | Ile | Val | Gln | Thr | Leu | Val | His | Phe | Ile | Asn | Pro | Asp | |
| | | 375 | | | | | 380 | | | | | 385 | | | | |

| ACA | GTA | CCC | AAG | CCC | TGC | TGT | GCG | CCC | ACC | CAG | CTC | AAC | GCC | ATC | TCT | 1315 |
|---|---|---|---|---|---|---|---|---|---|---|---|---|---|---|---|---|
| Thr | Val | Pro | Lys | Pro | Cys | Cys | Ala | Pro | Thr | Gln | Leu | Asn | Ala | Ile | Ser | |
| | 390 | | | | | 395 | | | | | 400 | | | | | |

| GTC | CTC | TAC | TTC | GAC | GAC | AGC | TCT | AAT | GTC | ATC | CTG | AAG | AAG | TAC | AGA | 1363 |

-continued

| | | | | | | | | | | | | | | | |
|---|---|---|---|---|---|---|---|---|---|---|---|---|---|---|---|
|Val|Leu|Tyr|Phe|Asp|Asp|Ser|Ser|Asn|Val|Ile|Leu|Lys|Lys|Tyr|Arg|
|405| | | | |410| | | |415| | | | |420| |

| | | | | | | | | | | |
|---|---|---|---|---|---|---|---|---|---|---|
|AAC|ATG|GTG|GTC|CGG|GCC|TGT|GGC|TGC|CAC|TAGCTCTTCC TGAGACCCTG|
|Asn|Met|Val|Val|Arg|Ala|Cys|Gly|Cys|His| |
| | | | |425| | | |430| | |

1413

ACCTTTGCGG GGCCACACCT TTCCAAATCT TCGATGTCTC ACCATCTAAG TCTCTCACTG 1473

CCCACCTTGG CGAGGAGAAC AGACCAACCT CTCCTGAGCC TTCCCTCACC TCCCAACCGG 1533

AAGCATGTAA GGGTTCCAGA AACCTGAGCG TGCAGCAGCT GATGAGCGCC CTTTCCTTCT 1593

GGCACGTGAC GGACAAGATC CTACCAGCTA CCACAGCAAA CGCCTAAGAG CAGGAAAAAT 1653

GTCTGCCAGG AAAGTGTCCA GTGTCCACAT GGCCCCTGGC GCTCTGAGTC TTTGAGGAGT 1713

AATCGCAAGC CTCGTTCAGC TGCAGCAGAA GGAAGGGCTT AGCCAGGGTG GGCGCTGGCG 1773

TCTGTGTTGA AGGGAAACCA AGCAGAAGCC ACTGTAATGA TATGTCACAA TAAAACCCAT 1833

GAATGAAAAA AAAAAAAAAA AAAAAAAAAA AAAAGAATTC 1873

( 2 ) INFORMATION FOR SEQ ID NO:19:

( i ) SEQUENCE CHARACTERISTICS:
  ( A ) LENGTH: 430 amino acids
  ( B ) TYPE: amino acid
  ( D ) TOPOLOGY: linear ( i i ) MOLECULE TYPE: protein ( x i ) SEQUENCE DESCRIPTION: SEQ ID NO:19:

| | | | | | | | | | | | | | | | |
|---|---|---|---|---|---|---|---|---|---|---|---|---|---|---|---|
|Met|His|Val|Arg|Ser|Leu|Arg|Ala|Ala|Pro|His|Ser|Phe|Val|Ala| |
|1| | | |5| | | | |10| | | | |15| |
|Leu|Trp|Ala|Pro|Leu|Phe|Leu|Leu|Arg|Ser|Ala|Leu|Ala|Asp|Phe|Ser|
| | | |20| | | | |25| | | | |30| | |
|Leu|Asp|Asn|Glu|Val|His|Ser|Ser|Phe|Ile|His|Arg|Arg|Leu|Arg|Ser|
| | |35| | | | |40| | | | |45| | | |
|Gln|Glu|Arg|Arg|Glu|Met|Gln|Arg|Glu|Ile|Leu|Ser|Ile|Leu|Gly|Leu|
| |50| | | | |55| | | | |60| | | | |
|Pro|His|Arg|Pro|Arg|Pro|His|Leu|Gln|Gly|Lys|His|Asn|Ser|Ala|Pro|
|65| | | | |70| | | | |75| | | | |80|
|Met|Phe|Met|Leu|Asp|Leu|Tyr|Asn|Ala|Met|Ala|Val|Glu|Glu|Ser|Gly|
| | | | |85| | | | |90| | | | |95| |
|Pro|Asp|Gly|Gln|Gly|Phe|Ser|Tyr|Pro|Tyr|Lys|Ala|Val|Phe|Ser|Thr|
| | | |100| | | | |105| | | | |110| | |
|Gln|Gly|Pro|Pro|Leu|Ala|Ser|Leu|Gln|Asp|Ser|His|Phe|Leu|Thr|Asp|
| | |115| | | | |120| | | | |125| | | |
|Ala|Asp|Met|Val|Met|Ser|Phe|Val|Asn|Leu|Val|Glu|His|Asp|Lys|Glu|
| |130| | | | |135| | | | |140| | | | |
|Phe|Phe|His|Pro|Arg|Tyr|His|His|Arg|Glu|Phe|Arg|Phe|Asp|Leu|Ser|
|145| | | | |150| | | | |155| | | | |160|
|Lys|Ile|Pro|Glu|Gly|Glu|Arg|Val|Thr|Ala|Ala|Glu|Phe|Arg|Ile|Tyr|
| | | | |165| | | | |170| | | | |175| |
|Lys|Asp|Tyr|Ile|Arg|Glu|Arg|Phe|Asp|Asn|Glu|Thr|Phe|Gln|Ile|Thr|
| | | |180| | | | |185| | | | |190| | |
|Val|Tyr|Gln|Val|Leu|Gln|Glu|His|Ser|Gly|Arg|Glu|Ser|Asp|Leu|Phe|
| | |195| | | | |200| | | | |205| | | |
|Leu|Leu|Asp|Ser|Arg|Thr|Ile|Trp|Ala|Ser|Glu|Glu|Gly|Trp|Leu|Val|
| |210| | | | |215| | | | |220| | | | |
|Phe|Asp|Ile|Thr|Ala|Thr|Ser|Asn|His|Trp|Val|Val|Asn|Pro|Arg|His|
|225| | | | |230| | | | |235| | | | |240|

```
Asn  Leu  Gly  Leu  Gln  Leu  Ser  Val  Glu  Thr  Leu  Asp  Gly  Gln  Ser  Ile
               245                 250                 255

Asn  Pro  Lys  Leu  Ala  Gly  Leu  Ile  Gly  Arg  His  Gly  Pro  Gln  Asn  Lys
               260                 265                 270

Gln  Pro  Phe  Met  Val  Ala  Phe  Phe  Lys  Ala  Thr  Glu  Val  His  Leu  Arg
               275                 280                 285

Ser  Ile  Arg  Ser  Thr  Gly  Gly  Lys  Gln  Arg  Ser  Gln  Asn  Arg  Ser  Lys
          290                 295                 300

Thr  Pro  Lys  Asn  Gln  Glu  Ala  Leu  Arg  Met  Ala  Ser  Val  Ala  Glu  Asn
305                      310                 315                      320

Ser  Ser  Ser  Asp  Gln  Arg  Gln  Ala  Cys  Lys  Lys  His  Glu  Leu  Tyr  Val
               325                 330                 335

Ser  Phe  Arg  Asp  Leu  Gly  Trp  Gln  Asp  Trp  Ile  Ile  Ala  Pro  Glu  Gly
               340                 345                 350

Tyr  Ala  Ala  Tyr  Tyr  Cys  Glu  Gly  Glu  Cys  Ala  Phe  Pro  Leu  Asn  Ser
               355                 360                 365

Tyr  Met  Asn  Ala  Thr  Asn  His  Ala  Ile  Val  Gln  Thr  Leu  Val  His  Phe
          370                 375                 380

Ile  Asn  Pro  Asp  Thr  Val  Pro  Lys  Pro  Cys  Cys  Ala  Pro  Thr  Gln  Leu
385                      390                 395                      400

Asn  Ala  Ile  Ser  Val  Leu  Tyr  Phe  Asp  Asp  Ser  Ser  Asn  Val  Ile  Leu
               405                 410                 415

Lys  Lys  Tyr  Arg  Asn  Met  Val  Val  Arg  Ala  Cys  Gly  Cys  His
               420                 425                 430
```

( 2 ) INFORMATION FOR SEQ ID NO:20:

( i ) SEQUENCE CHARACTERISTICS:
        ( A ) LENGTH: 1723 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 490..1695

( x i ) SEQUENCE DESCRIPTION: SEQ ID NO:20:

```
GGCGCCGGCA  GAGCAGGAGT  GGCTGGAGGA  GCTGTGGTTG  GAGCAGGAGG  TGGCACGGCA        60

GGGCTGGAGG  GCTCCCTATG  AGTGGCGGAG  ACGGCCCAGG  AGGCGCTGGA  GCAACAGCTC       120

CCACACCGCA  CCAAGCGGTG  GCTGCAGGAG  CTCGCCCATC  GCCCCTGCGC  TGCTCGGACC       180

GCGGCCACAG  CCGGACTGGC  GGGTACGGCG  GCGACAGAGG  CATTGGCCGA  GAGTCCCAGT       240

CCGCAGAGTA  GCCCCGGCCT  CGAGGCGGTG  GCGTCCCGGT  CCTCTCCGTC  CAGGAGCCAG       300

GACAGGTGTC  GCGCGGCGGG  GCTCCAGGGA  CCGCGCCTGA  GGCCGGCTGC  CGCCCGTCC       360

CGCCCCGCCC  CGCCGCCCGC  CGCCCGCCGA  GCCCAGCCTC  CTTGCCGTCG  GGGCGTCCCC       420

AGGCCCTGGG  TCGGCCGCGG  AGCCGATGCG  CGCCCGCTGA  GCGCCCCAGC  TGAGCGCCCC       480

CGGCCTGCC   ATG  ACC  GCG  CTC  CCC  GGC  CCG  CTC  TGG  CTC  CTG  GGC  CTG   528
            Met  Thr  Ala  Leu  Pro  Gly  Pro  Leu  Trp  Leu  Leu  Gly  Leu
             1                5                  10

GCG  CTA  TGC  GCG  CTG  GGC  GGG  GGC  GGC  CCC  GGC  CTG  CGA  CCC  CCG  CCC       576
Ala  Leu  Cys  Ala  Leu  Gly  Gly  Gly  Gly  Pro  Gly  Leu  Arg  Pro  Pro  Pro
     15                 20                      25

GGC  TGT  CCC  CAG  CGA  CGT  CTG  GGC  GCG  CGC  GAG  CGC  CGG  GAC  GTG  CAG       624
Gly  Cys  Pro  Gln  Arg  Arg  Leu  Gly  Ala  Arg  Glu  Arg  Arg  Asp  Val  Gln
```

|  |  |  |  |  |  |  |  |  |  |  |  |  |  |  |  |
|---|---|---|---|---|---|---|---|---|---|---|---|---|---|---|---|
| | 30 | | | | 35 | | | | 40 | | | | 45 | | |
| CGC | GAG | ATC | CTG | GCG | GTG | CTC | GGG | CTG | CCT | GGG | CGG | CCC | CGG | CCC | CGC | 672 |
| Arg | Glu | Ile | Leu | Ala 50 | Val | Leu | Gly | Leu | Pro 55 | Gly | Arg | Pro | Arg | Pro 60 | Arg | |
| GCG | CCA | CCC | GCC | GCC | TCC | CGG | CTG | CCC | GCG | TCC | GCG | CCG | CTC | TTC | ATG | 720 |
| Ala | Pro | Pro | Ala | Ala 65 | Ser | Arg | Leu | Pro | Ala 70 | Ser | Ala | Pro | Leu | Phe 75 | Met | |
| CTG | GAC | CTG | TAC | CAC | GCC | ATG | GCC | GGC | GAC | GAC | GAG | GAC | GGC | GCG | | 768 |
| Leu | Asp | Leu | Tyr 80 | His | Ala | Met | Ala | Gly 85 | Asp | Asp | Asp | Glu | Asp 90 | Gly | Ala | |
| CCC | GCG | GAG | CGG | CGC | CTG | GGC | CGC | GCC | GAC | CTG | GTC | ATG | AGC | TTC | GTT | 816 |
| Pro | Ala | Glu 95 | Arg | Arg | Leu | Gly | Arg 100 | Ala | Asp | Leu | Val | Met 105 | Ser | Phe | Val | |
| AAC | ATG | GTG | GAG | CGA | GAC | CGT | GCC | CTG | GGC | CAC | CAG | GAG | CCC | CAT | TGG | 864 |
| Asn | Met | Val | Glu | Arg 115 | Asp | Arg | Ala | Leu | Gly 120 | His | Gln | Glu | Pro | His 125 | Trp | |
| | | | | 110 | | | | | | | | | | | | |
| AAG | GAG | TTC | CGC | TTT | GAC | CTG | ACC | CAG | ATC | CCG | GCT | GGG | GAG | GCG | GTC | 912 |
| Lys | Glu | Phe | Arg | Phe 130 | Asp | Leu | Thr | Gln | Ile 135 | Pro | Ala | Gly | Glu | Ala 140 | Val | |
| ACA | GCT | GCG | GAG | TTC | CGG | ATT | TAC | AAG | GTG | CCC | AGC | ATC | CAC | CTG | CTC | 960 |
| Thr | Ala | Ala | Glu 145 | Phe | Arg | Ile | Tyr | Lys 150 | Val | Pro | Ser | Ile | His 155 | Leu | Leu | |
| AAC | AGG | ACC | CTC | CAC | GTC | AGC | ATG | TTC | CAG | GTG | GTC | CAG | GAG | CAG | TCC | 1008 |
| Asn | Arg | Thr 160 | Leu | His | Val | Ser | Met 165 | Phe | Gln | Val | Val | Gln 170 | Glu | Gln | Ser | |
| AAC | AGG | GAG | TCT | GAC | TTG | TTC | TTT | TTG | GAT | CTT | CAG | ACG | CTC | CGA | GCT | 1056 |
| Asn | Arg 175 | Glu | Ser | Asp | Leu | Phe 180 | Phe | Leu | Asp | Leu | Gln 185 | Thr | Leu | Arg | Ala | |
| GGA | GAC | GAG | GGC | TGG | CTG | GTG | CTG | GAT | GTC | ACA | GCA | GCC | AGT | GAC | TGC | 1104 |
| Gly 190 | Asp | Glu | Gly | Trp | Leu 195 | Val | Leu | Asp | Val | Thr 200 | Ala | Ala | Ser | Asp | Cys 205 | |
| TGG | TTG | CTG | AAG | CGT | CAC | AAG | GAC | CTG | GGA | CTC | CGC | CTC | TAT | GTG | GAG | 1152 |
| Trp | Leu | Leu | Lys | Arg 210 | His | Lys | Asp | Leu | Gly 215 | Leu | Arg | Leu | Tyr | Val 220 | Glu | |
| ACT | GAG | GAC | GGG | CAC | AGC | GTG | GAT | CCT | GGC | CTG | GCC | GGC | CTG | CTG | GGT | 1200 |
| Thr | Glu | Asp | Gly 225 | His | Ser | Val | Asp | Pro 230 | Gly | Leu | Ala | Gly | Leu 235 | Leu | Gly | |
| CAA | CGG | GCC | CCA | CGC | TCC | CAA | CAG | CCT | TTC | GTG | GTC | ACT | TTC | TTC | AGG | 1248 |
| Gln | Arg | Ala 240 | Pro | Arg | Ser | Gln | Gln 245 | Pro | Phe | Val | Val | Thr 250 | Phe | Phe | Arg | |
| GCC | AGT | CCG | AGT | CCC | ATC | CGC | ACC | CCT | CGG | GCA | GTG | AGG | CCA | CTG | AGG | 1296 |
| Ala | Ser | Pro 255 | Ser | Pro | Ile | Arg | Thr 260 | Pro | Arg | Ala | Val | Arg 265 | Pro | Leu | Arg | |
| AGG | AGG | CAG | CCG | AAG | AAA | AGC | AAC | GAG | CTG | CCG | CAG | GCC | AAC | CGA | CTC | 1344 |
| Arg 270 | Arg | Gln | Pro | Lys | Lys 275 | Ser | Asn | Glu | Leu | Pro 280 | Gln | Ala | Asn | Arg | Leu 285 | |
| CCA | GGG | ATC | TTT | GAT | GAC | GTC | CAC | GGC | TCC | CAC | GGC | CGG | CAG | GTC | TGC | 1392 |
| Pro | Gly | Ile | Phe | Asp 290 | Asp | Val | His | Gly | Ser 295 | His | Gly | Arg | Gln | Val 300 | Cys | |
| CGT | CGG | CAC | GAG | CTC | TAC | GTC | AGC | TTC | CAG | GAC | CTC | GGC | TGG | CTG | GAC | 1440 |
| Arg | Arg | His | Glu 305 | Leu | Tyr | Val | Ser | Phe 310 | Gln | Asp | Leu | Gly | Trp 315 | Leu | Asp | |
| TGG | GTC | ATC | GCT | CCC | CAA | GGC | TAC | TCG | GCC | TAT | TAC | TGT | GAG | GGG | GAG | 1488 |
| Trp | Val | Ile 320 | Ala | Pro | Gln | Gly | Tyr 325 | Ser | Ala | Tyr | Tyr | Cys 330 | Glu | Gly | Glu | |
| TGC | TCC | TTC | CCA | CTG | GAC | TCC | TGC | ATG | AAT | GCC | ACC | AAC | CAC | GCC | ATC | 1536 |
| Cys | Ser 335 | Phe | Pro | Leu | Asp | Ser 340 | Cys | Met | Asn | Ala | Thr 345 | Asn | His | Ala | Ile | |
| CTG | CAG | TCC | CTG | GTG | CAC | CTG | ATG | AAG | CCA | AAC | GCA | GTC | CCC | AAG | GCG | 1584 |
| Leu | Gln | Ser | Leu | Val | His | Leu | Met | Lys | Pro | Asn | Ala | Val | Pro | Lys | Ala | |

```
                350                      355                      360                      365
TGC  TGT  GCA  CCC  ACC  AAG  CTG  AGC  GCC  ACC  TCT  GTG  CTC  TAC  TAT  GAC          1632
Cys  Cys  Ala  Pro  Thr  Lys  Leu  Ser  Ala  Thr  Ser  Val  Leu  Tyr  Tyr  Asp
               370                      375                      380

AGC  AGC  AAC  AAC  GTC  ATC  CTG  CGC  AAA  CAC  CGC  AAC  ATG  GTG  GTC  AAG          1680
Ser  Ser  Asn  Asn  Val  Ile  Leu  Arg  Lys  His  Arg  Asn  Met  Val  Val  Lys
               385                      390                      395

GCC  TGC  GGC  TGC  CAC  TGAGTCAGCC  CGCCCAGCCC  TACTGCAG                                1723
Ala  Cys  Gly  Cys  His
               400
```

( 2 ) INFORMATION FOR SEQ ID NO:21:

( i ) SEQUENCE CHARACTERISTICS:
        ( A ) LENGTH: 402 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Met  Thr  Ala  Leu  Pro  Gly  Pro  Leu  Trp  Leu  Gly  Leu  Ala  Leu  Cys
 1                   5                   10                      15

Ala  Leu  Gly  Gly  Gly  Gly  Pro  Gly  Leu  Arg  Pro  Pro  Pro  Gly  Cys  Pro
               20                       25                      30

Gln  Arg  Arg  Leu  Gly  Ala  Arg  Glu  Arg  Arg  Asp  Val  Gln  Arg  Glu  Ile
          35                       40                       45

Leu  Ala  Val  Leu  Gly  Leu  Pro  Gly  Arg  Pro  Arg  Pro  Arg  Ala  Pro  Pro
     50                       55                      60

Ala  Ala  Ser  Arg  Leu  Pro  Ala  Ser  Ala  Pro  Leu  Phe  Met  Leu  Asp  Leu
 65                       70                      75                       80

Tyr  His  Ala  Met  Ala  Gly  Asp  Asp  Asp  Glu  Asp  Gly  Ala  Pro  Ala  Glu
                    85                       90                      95

Arg  Arg  Leu  Gly  Arg  Ala  Asp  Leu  Val  Met  Ser  Phe  Val  Asn  Met  Val
               100                      105                     110

Glu  Arg  Asp  Arg  Ala  Leu  Gly  His  Gln  Glu  Pro  His  Trp  Lys  Glu  Phe
          115                      120                     125

Arg  Phe  Asp  Leu  Thr  Gln  Ile  Pro  Ala  Gly  Glu  Ala  Val  Thr  Ala  Ala
     130                      135                     140

Glu  Phe  Arg  Ile  Tyr  Lys  Val  Pro  Ser  Ile  His  Leu  Leu  Asn  Arg  Thr
145                       150                     155                      160

Leu  His  Val  Ser  Met  Phe  Gln  Val  Val  Gln  Glu  Gln  Ser  Asn  Arg  Glu
                    165                      170                     175

Ser  Asp  Leu  Phe  Phe  Leu  Asp  Leu  Gln  Thr  Leu  Arg  Ala  Gly  Asp  Glu
               180                      185                     190

Gly  Trp  Leu  Val  Leu  Asp  Val  Thr  Ala  Ala  Ser  Asp  Cys  Trp  Leu  Leu
          195                      200                     205

Lys  Arg  His  Lys  Asp  Leu  Gly  Leu  Arg  Leu  Tyr  Val  Glu  Thr  Glu  Asp
     210                      215                     220

Gly  His  Ser  Val  Asp  Pro  Gly  Leu  Ala  Gly  Leu  Leu  Gly  Gln  Arg  Ala
225                       230                      235                     240

Pro  Arg  Ser  Gln  Gln  Pro  Phe  Val  Val  Thr  Phe  Phe  Arg  Ala  Ser  Pro
                    245                      250                     255

Ser  Pro  Ile  Arg  Thr  Pro  Arg  Ala  Val  Arg  Pro  Leu  Arg  Arg  Arg  Gln
               260                      265                     270

Pro  Lys  Lys  Ser  Asn  Glu  Leu  Pro  Gln  Ala  Asn  Arg  Leu  Pro  Gly  Ile
          275                      280                     285
```

```
Phe  Asp  Asp  Val  His  Gly  Ser  His  Gly  Arg  Gln  Val  Cys  Arg  Arg  His
     290                      295                 300

Glu  Leu  Tyr  Val  Ser  Phe  Gln  Asp  Leu  Gly  Trp  Leu  Asp  Trp  Val  Ile
305                           310                 315                      320

Ala  Pro  Gln  Gly  Tyr  Ser  Ala  Tyr  Tyr  Cys  Glu  Gly  Glu  Cys  Ser  Phe
                    325                      330                      335

Pro  Leu  Asp  Ser  Cys  Met  Asn  Ala  Thr  Asn  His  Ala  Ile  Leu  Gln  Ser
               340                      345                      350

Leu  Val  His  Leu  Met  Lys  Pro  Asn  Ala  Val  Pro  Lys  Ala  Cys  Cys  Ala
          355                      360                      365

Pro  Thr  Lys  Leu  Ser  Ala  Thr  Ser  Val  Leu  Tyr  Tyr  Asp  Ser  Ser  Asn
     370                      375                      380

Asn  Val  Ile  Leu  Arg  Lys  His  Arg  Asn  Met  Val  Val  Lys  Ala  Cys  Gly
385                      390                      395                      400

Cys  His
```

( 2 ) INFORMATION FOR SEQ ID NO:22:

( i ) SEQUENCE CHARACTERISTICS:
        ( A ) LENGTH: 1926 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 93..1289
        ( D ) OTHER INFORMATION: /product="MOP2 CDNA"

( x i ) SEQUENCE DESCRIPTION: SEQ ID NO:22:

```
GCCAGGCACA  GGTGCGCCGT  CTGGTCCTCC  CCGTCTGGCG  TCAGCCGAGC  CCGACCAGCT      60

ACCAGTGGAT  GCGCGCCGGC  TGAAAGTCCG  AG ATG GCT ATG CGT CCC GGG CCA         113
                                      Met Ala Met Arg Pro Gly Pro
                                        1           5

CTC  TGG  CTA  TTG  GGC  CTT  GCT  CTG  TGC  GCG  CTG  GGA  GGC  GGC  CAC  GGT   161
Leu  Trp  Leu  Leu  Gly  Leu  Ala  Leu  Cys  Ala  Leu  Gly  Gly  Gly  His  Gly
          10                       15                       20

CCG  CGT  CCC  CCG  CAC  ACC  TGT  CCC  CAG  CGT  CGC  CTG  GGA  GCG  CGC  GAG   209
Pro  Arg  Pro  Pro  His  Thr  Cys  Pro  Gln  Arg  Arg  Leu  Gly  Ala  Arg  Glu
     25                       30                       35

CGC  CGC  GAC  ATG  CAG  CGT  GAA  ATC  CTG  GCG  GTG  CTC  GGG  CTA  CCG  GGA   257
Arg  Arg  Asp  Met  Gln  Arg  Glu  Ile  Leu  Ala  Val  Leu  Gly  Leu  Pro  Gly
40                       45                       50                        55

CGG  CCC  CGA  CCC  CGT  GCA  CAA  CCC  GCG  GCT  GCC  CGG  CAG  CCA  GCG  TCC   305
Arg  Pro  Arg  Pro  Arg  Ala  Gln  Pro  Ala  Ala  Ala  Arg  Gln  Pro  Ala  Ser
                         60                       65                       70

GCG  CCC  CTC  TTC  ATG  TTG  GAC  CTA  TAC  CAC  GCC  ATG  ACC  GAT  GAC  GAC   353
Ala  Pro  Leu  Phe  Met  Leu  Asp  Leu  Tyr  His  Ala  Met  Thr  Asp  Asp  Asp
               75                       80                       85

GAC  GGC  GGG  CCA  CCA  CAG  GCT  CAC  TTA  GGC  CGT  GCC  GAC  CTG  GTC  ATG   401
Asp  Gly  Gly  Pro  Pro  Gln  Ala  His  Leu  Gly  Arg  Ala  Asp  Leu  Val  Met
          90                       95                      100

AGC  TTC  GTC  AAC  ATG  GTG  GAA  CGC  GAC  CGT  ACC  CTG  GGC  TAC  CAG  GAG   449
Ser  Phe  Val  Asn  Met  Val  Glu  Arg  Asp  Arg  Thr  Leu  Gly  Tyr  Gln  Glu
     105                     110                      115

CCA  CAC  TGG  AAG  GAA  TTC  CAC  TTT  GAC  CTA  ACC  CAG  ATC  CCT  GCT  GGG   497
Pro  His  Trp  Lys  Glu  Phe  His  Phe  Asp  Leu  Thr  Gln  Ile  Pro  Ala  Gly
120                      125                      130                      135
```

-continued

| | | | | | | | | | | | | | | | | |
|---|---|---|---|---|---|---|---|---|---|---|---|---|---|---|---|---|
| GAG | GCT | GTC | ACA | GCT | GCT | GAG | TTC | CGG | ATC | TAC | AAA | GAA | CCC | AGC | ACC | 545 |
| Glu | Ala | Val | Thr 140 | Ala | Ala | Glu | Phe | Arg | Ile | Tyr 145 | Lys | Glu | Pro | Ser 150 | Thr | |
| CAC | CCG | CTC | AAC | ACA | ACC | CTC | CAC | ATC | AGC | ATG | TTC | GAA | GTG | GTC | CAA | 593 |
| His | Pro | Leu | Asn 155 | Thr | Thr | Leu | His | Ile 160 | Ser | Met | Phe | Glu | Val 165 | Val | Gln | |
| GAG | CAC | TCC | AAC | AGG | GAG | TCT | GAC | TTG | TTC | TTT | TTG | GAT | CTT | CAG | ACG | 641 |
| Glu | His | Ser | Asn 170 | Arg | Glu | Ser | Asp | Leu 175 | Phe | Phe | Leu | Asp | Leu 180 | Gln | Thr | |
| CTC | CGA | TCT | GGG | GAC | GAG | GGC | TGG | CTG | GTG | CTG | GAC | ATC | ACA | GCA | GCC | 689 |
| Leu | Arg | Ser 185 | Gly | Asp | Glu | Gly | Trp | Leu 190 | Val | Leu | Asp | Ile | Thr 195 | Ala | Ala | |
| AGT | GAC | CGA | TGG | CTG | CTG | AAC | CAT | CAC | AAG | GAC | CTG | GGA | CTC | CGC | CTC | 737 |
| Ser 200 | Asp | Arg | Trp | Leu | Leu 205 | Asn | His | His | Lys | Asp 210 | Leu | Gly | Leu | Arg | Leu 215 | |
| TAT | GTG | GAA | ACC | GCG | GAT | GGG | CAC | AGC | ATG | GAT | CCT | GGC | CTG | GCT | GGT | 785 |
| Tyr | Val | Glu | Thr | Ala 220 | Asp | Gly | His | Ser | Met 225 | Asp | Pro | Gly | Leu | Ala 230 | Gly | |
| CTG | CTT | GGA | CGA | CAA | GCA | CCA | CGC | TCC | AGA | CAG | CCT | TTC | ATG | GTA | ACC | 833 |
| Leu | Leu | Gly | Arg 235 | Gln | Ala | Pro | Arg | Ser 240 | Arg | Gln | Pro | Phe | Met 245 | Val | Thr | |
| TTC | TTC | AGG | GCC | AGC | CAG | AGT | CCT | GTG | CGG | GCC | CCT | CGG | GCA | GCG | AGA | 881 |
| Phe | Phe | Arg | Ala | Ser 250 | Gln | Ser | Pro | Val | Arg 255 | Ala | Pro | Arg | Ala | Ala 260 | Arg | |
| CCA | CTG | AAG | AGG | AGG | CAG | CCA | AAG | AAA | ACG | AAC | GAG | CTT | CCG | CAC | CCC | 929 |
| Pro | Leu | Lys 265 | Arg | Arg | Gln | Pro | Lys 270 | Lys | Thr | Asn | Glu | Leu 275 | Pro | His | Pro | |
| AAC | AAA | CTC | CCA | GGG | ATC | TTT | GAT | GAT | GGC | CAC | GGT | TCC | CGC | GGC | AGA | 977 |
| Asn 280 | Lys | Leu | Pro | Gly | Ile 285 | Phe | Asp | Asp | Gly | His 290 | Gly | Ser | Arg | Gly | Arg 295 | |
| GAG | GTT | TGC | CGC | AGG | CAT | GAG | CTC | TAC | GTC | AGC | TTC | CGT | GAC | CTT | GGC | 1025 |
| Glu | Val | Cys | Arg | Arg 300 | His | Glu | Leu | Tyr | Val 305 | Ser | Phe | Arg | Asp | Leu 310 | Gly | |
| TGG | CTG | GAC | TGG | GTC | ATC | GCC | CCC | CAG | GGC | TAC | TCT | GCC | TAT | TAC | TGT | 1073 |
| Trp | Leu | Asp | Trp 315 | Val | Ile | Ala | Pro | Gln 320 | Gly | Tyr | Ser | Ala | Tyr 325 | Tyr | Cys | |
| GAG | GGG | GAG | TGT | GCT | TTC | CCA | CTG | GAC | TCC | TGT | ATG | AAC | GCC | ACC | AAC | 1121 |
| Glu | Gly | Glu | Cys 330 | Ala | Phe | Pro | Leu | Asp 335 | Ser | Cys | Met | Asn | Ala 340 | Thr | Asn | |
| CAT | GCC | ATC | TTG | CAG | TCT | CTG | GTG | CAC | CTG | ATG | AAG | CCA | GAT | GTT | GTC | 1169 |
| His | Ala | Ile | Leu | Gln 345 | Ser | Leu | Val | His | Leu 350 | Met | Lys | Pro | Asp | Val 355 | Val | |
| CCC | AAG | GCA | TGC | TGT | GCA | CCC | ACC | AAA | CTG | AGT | GCC | ACC | TCT | GTG | CTG | 1217 |
| Pro 360 | Lys | Ala | Cys | Cys | Ala 365 | Pro | Thr | Lys | Leu | Ser 370 | Ala | Thr | Ser | Val | Leu 375 | |
| TAC | TAT | GAC | AGC | AGC | AAC | AAT | GTC | ATC | CTG | CGT | AAA | CAC | CGT | AAC | ATG | 1265 |
| Tyr | Tyr | Asp | Ser | Ser 380 | Asn | Asn | Val | Ile | Leu 385 | Arg | Lys | His | Arg | Asn 390 | Met | |
| GTG | GTC | AAG | GCC | TGT | GGC | TGC | CAC | TGAGGCCCCG | | | CCCAGCATCC | | TGCTTCTACT | | | 1319 |
| Val | Val | Lys | Ala | Cys 395 | Gly | Cys | His | | | | | | | | | |

ACCTTACCAT CTGGCCGGGC CCCTCTCCAG AGGCAGAAAC CCTTCTATGT TATCATAGCT   1379

CAGACAGGGG CAATGGGAGG CCCTTCACTT CCCCTGGCCA CTTCCTGCTA AAATTCTGGT   1439

CTTTCCAGT TCCTCTGTCC TTCATGGGGT TTCGGGGCTA TCACCCCGCC CTCTCCATCC   1499

TCCTACCCCA AGCATAGACT GAATGCACAC AGCATCCAG AGCTATGCTA ACTGAGAGGT   1559

CTGGGGTCAG CACTGAAGGC CCACATGAGG AAGACTGATC CTTGGCCATC CTCAGCCCAC   1619

AATGGCAAAT TCTGGATGGT CTAAGAAGGC CCTGGAATTC TAAACTAGAT GATCTGGGCT   1679

-continued

```
CTCTGCACCA TTCATTGTGG CAGTTGGGAC ATTTTTAGGT ATAACAGACA CATACACTTA    1739

GATCAATGCA TCGCTGTACT CCTTGAAATC AGAGCTAGCT TGTTAGAAAA AGAATCAGAG    1799

CCAGGTATAG CGGTGCATGT CATTAATCCC AGCGCTAAAG AGACAGAGAC AGGAGAATCT    1859

CTGTGAGTTC AAGGCCACAT AGAAAGAGCC TGTCTCGGGA GCAGGAAAAA AAAAAAAAAC    1919

GGAATTC                                                              1926
```

( 2 ) INFORMATION FOR SEQ ID NO:23:

( i ) SEQUENCE CHARACTERISTICS:
        ( A ) LENGTH: 399 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

```
Met Ala Met Arg Pro Gly Pro Leu Trp Leu Gly Leu Ala Leu Cys
 1           5                  10                  15

Ala Leu Gly Gly Gly His Gly Pro Arg Pro Pro His Thr Cys Pro Gln
            20                  25                  30

Arg Arg Leu Gly Ala Arg Glu Arg Arg Asp Met Gln Arg Glu Ile Leu
        35                  40                  45

Ala Val Leu Gly Leu Pro Gly Arg Pro Arg Pro Arg Ala Gln Pro Ala
    50                  55                  60

Ala Ala Arg Gln Pro Ala Ser Ala Pro Leu Phe Met Leu Asp Leu Tyr
65                  70                  75                  80

His Ala Met Thr Asp Asp Asp Asp Gly Gly Pro Pro Gln Ala His Leu
                85                  90                  95

Gly Arg Ala Asp Leu Val Met Ser Phe Val Asn Met Val Glu Arg Asp
            100                 105                 110

Arg Thr Leu Gly Tyr Gln Glu Pro His Trp Lys Glu Phe His Phe Asp
        115                 120                 125

Leu Thr Gln Ile Pro Ala Gly Glu Ala Val Thr Ala Ala Glu Phe Arg
    130                 135                 140

Ile Tyr Lys Glu Pro Ser Thr His Pro Leu Asn Thr Thr Leu His Ile
145                 150                 155                 160

Ser Met Phe Glu Val Val Gln Glu His Ser Asn Arg Glu Ser Asp Leu
                165                 170                 175

Phe Phe Leu Asp Leu Gln Thr Leu Arg Ser Gly Asp Glu Gly Trp Leu
            180                 185                 190

Val Leu Asp Ile Thr Ala Ala Ser Asp Arg Trp Leu Leu Asn His His
        195                 200                 205

Lys Asp Leu Gly Leu Arg Leu Tyr Val Glu Thr Ala Asp Gly His Ser
    210                 215                 220

Met Asp Pro Gly Leu Ala Gly Leu Leu Gly Arg Gln Ala Pro Arg Ser
225                 230                 235                 240

Arg Gln Pro Phe Met Val Thr Phe Phe Arg Ala Ser Gln Ser Pro Val
                245                 250                 255

Arg Ala Pro Arg Ala Ala Arg Pro Leu Lys Arg Arg Gln Pro Lys Lys
            260                 265                 270

Thr Asn Glu Leu Pro His Pro Asn Lys Leu Pro Gly Ile Phe Asp Asp
        275                 280                 285

Gly His Gly Ser Arg Gly Arg Glu Val Cys Arg Arg His Glu Leu Tyr
    290                 295                 300

Val Ser Phe Arg Asp Leu Gly Trp Leu Asp Trp Val Ile Ala Pro Gln
```

| | | | | | 305 | | | | | 310 | | | | | 315 | | | | | 320 |
|---|---|---|---|---|---|---|---|---|---|---|---|---|---|---|---|---|---|---|---|---|
| Gly | Tyr | Ser | Ala | Tyr | | Tyr | Cys | Glu | Gly | | Glu | Cys | Ala | Phe | | Pro | Leu | Asp | | |
| | | | | 325 | | | | | | 330 | | | | | | 335 | | | | |

| Ser | Cys | Met | Asn | Ala | Thr | Asn | His | Ala | Ile | Leu | Gln | Ser | Leu | Val | His |
|---|---|---|---|---|---|---|---|---|---|---|---|---|---|---|---|
| | | | 340 | | | | 345 | | | | | 350 | | | |

| Leu | Met | Lys | Pro | Asp | Val | Val | Pro | Lys | Ala | Cys | Cys | Ala | Pro | Thr | Lys |
|---|---|---|---|---|---|---|---|---|---|---|---|---|---|---|---|
| | | 355 | | | | | 360 | | | | | 365 | | | |

| Leu | Ser | Ala | Thr | Ser | Val | Leu | Tyr | Tyr | Asp | Ser | Ser | Asn | Asn | Val | Ile |
|---|---|---|---|---|---|---|---|---|---|---|---|---|---|---|---|
| | 370 | | | | | 375 | | | | | 380 | | | | |

Leu Arg Lys His Arg Asn Met Val Val Lys Ala Cys Gly Cys His
385                    390                    395

( 2 ) INFORMATION FOR SEQ ID NO:24:

( i ) SEQUENCE CHARACTERISTICS:
        ( A ) LENGTH: 1368 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1365

( x i ) SEQUENCE DESCRIPTION: SEQ ID NO:24:

| ATG | TCG | GGA | CTG | CGA | AAC | ACC | TCG | GAG | GCC | GTT | GCA | GTG | CTC | GCC | TCC | 48 |
|---|---|---|---|---|---|---|---|---|---|---|---|---|---|---|---|---|
| Met | Ser | Gly | Leu | Arg | Asn | Thr | Ser | Glu | Ala | Val | Ala | Val | Leu | Ala | Ser | |
| 1 | | | | 5 | | | | | 10 | | | | | 15 | | |

| CTG | GGA | CTC | GGA | ATG | GTT | CTG | CTC | ATG | TTC | GTG | GCG | ACC | ACG | CCG | CCG | 96 |
|---|---|---|---|---|---|---|---|---|---|---|---|---|---|---|---|---|
| Leu | Gly | Leu | Gly | Met | Val | Leu | Leu | Met | Phe | Val | Ala | Thr | Thr | Pro | Pro | |
| | | | 20 | | | | | 25 | | | | | 30 | | | |

| GCC | GTT | GAG | GCC | ACC | CAG | TCG | GGG | ATT | TAC | ATA | GAC | AAC | GGC | AAG | GAC | 144 |
|---|---|---|---|---|---|---|---|---|---|---|---|---|---|---|---|---|
| Ala | Val | Glu | Ala | Thr | Gln | Ser | Gly | Ile | Tyr | Ile | Asp | Asn | Gly | Lys | Asp | |
| | | 35 | | | | | 40 | | | | | 45 | | | | |

| CAG | ACG | ATC | ATG | CAC | AGA | GTG | CTG | AGC | GAG | GAC | GAC | AAG | CTG | GAC | GTC | 192 |
|---|---|---|---|---|---|---|---|---|---|---|---|---|---|---|---|---|
| Gln | Thr | Ile | Met | His | Arg | Val | Leu | Ser | Glu | Asp | Asp | Lys | Leu | Asp | Val | |
| 50 | | | | | 55 | | | | | 60 | | | | | | |

| TCG | TAC | GAG | ATC | CTC | GAG | TTC | CTG | GGC | ATC | GCC | GAA | CGG | CCG | ACG | CAC | 240 |
|---|---|---|---|---|---|---|---|---|---|---|---|---|---|---|---|---|
| Ser | Tyr | Glu | Ile | Leu | Glu | Phe | Leu | Gly | Ile | Ala | Glu | Arg | Pro | Thr | His | |
| 65 | | | | | 70 | | | | | 75 | | | | | 80 | |

| CTG | AGC | AGC | CAC | CAG | TTG | TCG | CTG | AGG | AAG | TCG | GCT | CCC | AAG | TTC | CTG | 288 |
|---|---|---|---|---|---|---|---|---|---|---|---|---|---|---|---|---|
| Leu | Ser | Ser | His | Gln | Leu | Ser | Leu | Arg | Lys | Ser | Ala | Pro | Lys | Phe | Leu | |
| | | | | 85 | | | | | 90 | | | | | 95 | | |

| CTG | GAC | GTC | TAC | CAC | CGC | ATC | ACG | GCG | GAG | GAG | GGT | CTC | AGC | GAT | CAG | 336 |
|---|---|---|---|---|---|---|---|---|---|---|---|---|---|---|---|---|
| Leu | Asp | Val | Tyr | His | Arg | Ile | Thr | Ala | Glu | Glu | Gly | Leu | Ser | Asp | Gln | |
| | | | 100 | | | | | 105 | | | | | 110 | | | |

| GAT | GAG | GAC | GAC | GAC | TAC | GAA | CGC | GGC | CAT | CGG | TCC | AGG | AGG | AGC | GCC | 384 |
|---|---|---|---|---|---|---|---|---|---|---|---|---|---|---|---|---|
| Asp | Glu | Asp | Asp | Asp | Tyr | Glu | Arg | Gly | His | Arg | Ser | Arg | Arg | Ser | Ala | |
| | | 115 | | | | | 120 | | | | | 125 | | | | |

| GAC | CTC | GAG | GAG | GAT | GAG | GGC | GAG | CAG | CAG | AAG | AAC | TTC | ATC | ACC | GAC | 432 |
|---|---|---|---|---|---|---|---|---|---|---|---|---|---|---|---|---|
| Asp | Leu | Glu | Glu | Asp | Glu | Gly | Glu | Gln | Gln | Lys | Asn | Phe | Ile | Thr | Asp | |
| | 130 | | | | | 135 | | | | | 140 | | | | | |

| CTG | GAC | AAG | CGG | GCC | ATC | GAC | GAG | AGC | GAC | ATC | ATC | ATG | ACC | TTC | CTG | 480 |
|---|---|---|---|---|---|---|---|---|---|---|---|---|---|---|---|---|
| Leu | Asp | Lys | Arg | Ala | Ile | Asp | Glu | Ser | Asp | Ile | Ile | Met | Thr | Phe | Leu | |
| 145 | | | | | 150 | | | | | 155 | | | | | 160 | |

| AAC | AAG | CGC | CAC | CAC | AAT | GTG | GAC | GAA | CTG | CGT | CAC | GAG | CAC | GGC | CGT | 528 |
|---|---|---|---|---|---|---|---|---|---|---|---|---|---|---|---|---|
| Asn | Lys | Arg | His | His | Asn | Val | Asp | Glu | Leu | Arg | His | Glu | His | Gly | Arg | |
| | | | | 165 | | | | | 170 | | | | | 175 | | |

| CGC | CTG | TGG | TTC | GAC | GTC | TCC | AAC | GTG | CCC | AAC | GAC | AAC | TAC | CTG | GTG | 576 |
|---|---|---|---|---|---|---|---|---|---|---|---|---|---|---|---|---|
| Arg | Leu | Trp | Phe | Asp | Val | Ser | Asn | Val | Pro | Asn | Asp | Asn | Tyr | Leu | Val | |

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
|     |     |     | 180 |     |     |     |     | 185 |     |     |     |     | 190 |     |     |     |
| ATG | GCC | GAG | CTG | CGC | ATC | TAT | CAG | AAC | GCC | AAC | GAG | GGC | AAG | TGG | CTG | 624 |
| Met | Ala | Glu | Leu | Arg | Ile | Tyr | Gln | Asn | Ala | Asn | Glu | Gly | Lys | Trp | Leu |     |
|     |     | 195 |     |     |     |     | 200 |     |     |     |     | 205 |     |     |     |     |
| ACC | GCC | AAC | AGG | GAG | TTC | ACC | ATC | ACG | GTA | TAC | GCC | ATT | GGC | ACC | GGC | 672 |
| Thr | Ala | Asn | Arg | Glu | Phe | Thr | Ile | Thr | Val | Tyr | Ala | Ile | Gly | Thr | Gly |     |
|     | 210 |     |     |     |     | 215 |     |     |     |     | 220 |     |     |     |     |     |
| ACG | CTG | GGC | CAG | CAC | ACC | ATG | GAG | CCG | CTG | TCC | TCG | GTG | AAC | ACC | ACC | 720 |
| Thr | Leu | Gly | Gln | His | Thr | Met | Glu | Pro | Leu | Ser | Ser | Val | Asn | Thr | Thr |     |
| 225 |     |     |     |     | 230 |     |     |     |     | 235 |     |     |     |     | 240 |     |
| GGG | GAC | TAC | GTG | GGC | TGG | TTG | GAG | CTC | AAC | GTG | ACC | GAG | GGC | CTG | CAC | 768 |
| Gly | Asp | Tyr | Val | Gly | Trp | Leu | Glu | Leu | Asn | Val | Thr | Glu | Gly | Leu | His |     |
|     |     |     |     | 245 |     |     |     |     | 250 |     |     |     |     | 255 |     |     |
| GAG | TGG | CTG | GTC | AAG | TCG | AAG | GAC | AAT | CAT | GGC | ATC | TAC | ATT | GGA | GCA | 816 |
| Glu | Trp | Leu | Val | Lys | Ser | Lys | Asp | Asn | His | Gly | Ile | Tyr | Ile | Gly | Ala |     |
|     |     |     | 260 |     |     |     |     | 265 |     |     |     |     | 270 |     |     |     |
| CAC | GCT | GTC | AAC | CGA | CCC | GAC | CGC | GAG | GTG | AAG | CTG | GAC | GAC | ATT | GGA | 864 |
| His | Ala | Val | Asn | Arg | Pro | Asp | Arg | Glu | Val | Lys | Leu | Asp | Asp | Ile | Gly |     |
|     |     |     | 275 |     |     |     |     | 280 |     |     |     |     | 285 |     |     |     |
| CTG | ATC | CAC | CGC | AAG | GTG | GAC | GAC | GAG | TTC | CAG | CCC | TTC | ATG | ATC | GGC | 912 |
| Leu | Ile | His | Arg | Lys | Val | Asp | Asp | Glu | Phe | Gln | Pro | Phe | Met | Ile | Gly |     |
|     | 290 |     |     |     |     | 295 |     |     |     |     | 300 |     |     |     |     |     |
| TTC | TTC | CGC | GGA | CCG | GAG | CTG | ATC | AAG | GCG | ACG | GCC | CAC | AGC | AGC | CAC | 960 |
| Phe | Phe | Arg | Gly | Pro | Glu | Leu | Ile | Lys | Ala | Thr | Ala | His | Ser | Ser | His |     |
| 305 |     |     |     |     | 310 |     |     |     |     | 315 |     |     |     |     | 320 |     |
| CAC | AGG | AGC | AAG | CGA | AGC | GCC | AGC | CAT | CCA | CGC | AAG | CGC | AAG | AAG | TCG | 1008 |
| His | Arg | Ser | Lys | Arg | Ser | Ala | Ser | His | Pro | Arg | Lys | Arg | Lys | Lys | Ser |     |
|     |     |     |     | 325 |     |     |     |     | 330 |     |     |     |     | 335 |     |     |
| GTG | TCG | CCC | AAC | AAC | GTG | CCG | CTG | CTG | GAA | CCG | ATG | GAG | AGC | ACG | CGC | 1056 |
| Val | Ser | Pro | Asn | Asn | Val | Pro | Leu | Leu | Glu | Pro | Met | Glu | Ser | Thr | Arg |     |
|     |     |     | 340 |     |     |     |     | 345 |     |     |     |     | 350 |     |     |     |
| AGC | TGC | CAG | ATG | CAG | ACC | CTG | TAC | ATA | GAC | TTC | AAG | GAT | CTG | GGC | TGG | 1104 |
| Ser | Cys | Gln | Met | Gln | Thr | Leu | Tyr | Ile | Asp | Phe | Lys | Asp | Leu | Gly | Trp |     |
|     |     | 355 |     |     |     |     | 360 |     |     |     |     | 365 |     |     |     |     |
| CAT | GAC | TGG | ATC | ATC | GCA | CCA | GAG | GGC | TAT | GGC | GCC | TTC | TAC | TGC | AGC | 1152 |
| His | Asp | Trp | Ile | Ile | Ala | Pro | Glu | Gly | Tyr | Gly | Ala | Phe | Tyr | Cys | Ser |     |
|     | 370 |     |     |     |     | 375 |     |     |     |     | 380 |     |     |     |     |     |
| GGC | GAG | TGC | AAT | TTC | CCG | CTC | AAT | GCG | CAC | ATG | AAC | GCC | ACG | AAC | CAT | 1200 |
| Gly | Glu | Cys | Asn | Phe | Pro | Leu | Asn | Ala | His | Met | Asn | Ala | Thr | Asn | His |     |
| 385 |     |     |     |     | 390 |     |     |     |     | 395 |     |     |     |     | 400 |     |
| GCG | ATC | GTC | CAG | ACC | CTG | GTC | CAC | CTG | CTG | GAG | CCC | AAG | AAG | GTG | CCC | 1248 |
| Ala | Ile | Val | Gln | Thr | Leu | Val | His | Leu | Leu | Glu | Pro | Lys | Lys | Val | Pro |     |
|     |     |     |     | 405 |     |     |     |     | 410 |     |     |     |     | 415 |     |     |
| AAG | CCC | TGC | TGC | GCT | CCG | ACC | AGG | CTG | GGA | GCA | CTA | CCC | GTT | CTG | TAC | 1296 |
| Lys | Pro | Cys | Cys | Ala | Pro | Thr | Arg | Leu | Gly | Ala | Leu | Pro | Val | Leu | Tyr |     |
|     |     |     | 420 |     |     |     |     | 425 |     |     |     |     | 430 |     |     |     |
| CAC | CTG | AAC | GAC | GAG | AAT | GTG | AAC | CTG | AAA | AAG | TAT | AGA | AAC | ATG | ATT | 1344 |
| His | Leu | Asn | Asp | Glu | Asn | Val | Asn | Leu | Lys | Lys | Tyr | Arg | Asn | Met | Ile |     |
|     |     |     | 435 |     |     |     |     | 440 |     |     |     |     | 445 |     |     |     |
| GTG | AAA | TCC | TGC | GGG | TGC | CAT | TGA |     |     |     |     |     |     |     |     | 1368 |
| Val | Lys | Ser | Cys | Gly | Cys | His |     |     |     |     |     |     |     |     |     |     |
|     | 450 |     |     |     |     | 455 |     |     |     |     |     |     |     |     |     |     |

( 2 ) INFORMATION FOR SEQ ID NO:25:

( i ) SEQUENCE CHARACTERISTICS:
        ( A ) LENGTH: 455 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| Met | Ser | Gly | Leu | Arg | Asn | Thr | Ser | Glu | Ala | Val | Ala | Val | Leu | Ala | Ser |
| 1 | | | | 5 | | | | | 10 | | | | | 15 | |

| Leu | Gly | Leu | Gly | Met | Val | Leu | Leu | Met | Phe | Val | Ala | Thr | Thr | Pro | Pro |
| | | | 20 | | | | | 25 | | | | | 30 | | |

| Ala | Val | Glu | Ala | Thr | Gln | Ser | Gly | Ile | Tyr | Ile | Asp | Asn | Gly | Lys | Asp |
| | | 35 | | | | | 40 | | | | | 45 | | | |

| Gln | Thr | Ile | Met | His | Arg | Val | Leu | Ser | Glu | Asp | Asp | Lys | Leu | Asp | Val |
| | 50 | | | | | 55 | | | | | 60 | | | | |

| Ser | Tyr | Glu | Ile | Leu | Glu | Phe | Leu | Gly | Ile | Ala | Glu | Arg | Pro | Thr | His |
| 65 | | | | | 70 | | | | | 75 | | | | | 80 |

| Leu | Ser | Ser | His | Gln | Leu | Ser | Leu | Arg | Lys | Ser | Ala | Pro | Lys | Phe | Leu |
| | | | | 85 | | | | | 90 | | | | | 95 | |

| Leu | Asp | Val | Tyr | His | Arg | Ile | Thr | Ala | Glu | Glu | Gly | Leu | Ser | Asp | Gln |
| | | | | 100 | | | | | 105 | | | | | 110 | |

| Asp | Glu | Asp | Asp | Asp | Tyr | Glu | Arg | Gly | His | Arg | Ser | Arg | Arg | Ser | Ala |
| | | 115 | | | | | 120 | | | | | 125 | | | |

| Asp | Leu | Glu | Glu | Asp | Glu | Gly | Glu | Gln | Gln | Lys | Asn | Phe | Ile | Thr | Asp |
| | 130 | | | | | 135 | | | | | 140 | | | | |

| Leu | Asp | Lys | Arg | Ala | Ile | Asp | Glu | Ser | Asp | Ile | Ile | Met | Thr | Phe | Leu |
| 145 | | | | | 150 | | | | | 155 | | | | | 160 |

| Asn | Lys | Arg | His | His | Asn | Val | Asp | Glu | Leu | Arg | His | Glu | His | Gly | Arg |
| | | | | 165 | | | | | 170 | | | | | 175 | |

| Arg | Leu | Trp | Phe | Asp | Val | Ser | Asn | Val | Pro | Asn | Asp | Asn | Tyr | Leu | Val |
| | | | 180 | | | | | 185 | | | | | 190 | | |

| Met | Ala | Glu | Leu | Arg | Ile | Tyr | Gln | Asn | Ala | Asn | Glu | Gly | Lys | Trp | Leu |
| | | 195 | | | | | 200 | | | | | 205 | | | |

| Thr | Ala | Asn | Arg | Glu | Phe | Thr | Ile | Thr | Val | Tyr | Ala | Ile | Gly | Thr | Gly |
| | 210 | | | | | 215 | | | | | 220 | | | | |

| Thr | Leu | Gly | Gln | His | Thr | Met | Glu | Pro | Leu | Ser | Ser | Val | Asn | Thr | Thr |
| 225 | | | | | 230 | | | | | 235 | | | | | 240 |

| Gly | Asp | Tyr | Val | Gly | Trp | Leu | Glu | Leu | Asn | Val | Thr | Glu | Gly | Leu | His |
| | | | | 245 | | | | | 250 | | | | | 255 | |

| Glu | Trp | Leu | Val | Lys | Ser | Lys | Asp | Asn | His | Gly | Ile | Tyr | Ile | Gly | Ala |
| | | | 260 | | | | | 265 | | | | | 270 | | |

| His | Ala | Val | Asn | Arg | Pro | Asp | Arg | Glu | Val | Lys | Leu | Asp | Asp | Ile | Gly |
| | | 275 | | | | | 280 | | | | | 285 | | | |

| Leu | Ile | His | Arg | Lys | Val | Asp | Asp | Glu | Phe | Gln | Pro | Phe | Met | Ile | Gly |
| | 290 | | | | | 295 | | | | | 300 | | | | |

| Phe | Phe | Arg | Gly | Pro | Glu | Leu | Ile | Lys | Ala | Thr | Ala | His | Ser | Ser | His |
| 305 | | | | | 310 | | | | | 315 | | | | | 320 |

| His | Arg | Ser | Lys | Arg | Ser | Ala | Ser | His | Pro | Arg | Lys | Arg | Lys | Lys | Ser |
| | | | | 325 | | | | | 330 | | | | | 335 | |

| Val | Ser | Pro | Asn | Asn | Val | Pro | Leu | Leu | Glu | Pro | Met | Glu | Ser | Thr | Arg |
| | | | 340 | | | | | 345 | | | | | 350 | | |

| Ser | Cys | Gln | Met | Gln | Thr | Leu | Tyr | Ile | Asp | Phe | Lys | Asp | Leu | Gly | Trp |
| | | 355 | | | | | 360 | | | | | 365 | | | |

| His | Asp | Trp | Ile | Ile | Ala | Pro | Glu | Gly | Tyr | Gly | Ala | Phe | Tyr | Cys | Ser |
| | 370 | | | | | 375 | | | | | 380 | | | | |

| Gly | Glu | Cys | Asn | Phe | Pro | Leu | Asn | Ala | His | Met | Asn | Ala | Thr | Asn | His |
| 385 | | | | | 390 | | | | | 395 | | | | | 400 |

| Ala | Ile | Val | Gln | Thr | Leu | Val | His | Leu | Leu | Glu | Pro | Lys | Lys | Val | Pro |
| | | | | 405 | | | | | 410 | | | | | 415 | |

```
Lys Pro Cys Cys Ala Pro Thr Arg Leu Gly Ala Leu Pro Val Leu Tyr
            420                 425                 430

His Leu Asn Asp Glu Asn Val Asn Leu Lys Lys Tyr Arg Asn Met Ile
        435                 440                 445

Val Lys Ser Cys Gly Cys His
    450             455
```

( 2 ) INFORMATION FOR SEQ ID NO:26:

( i ) SEQUENCE CHARACTERISTICS:
        ( A ) LENGTH: 104 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..104
        ( D ) OTHER INFORMATION: /label=BMP3

( x i ) SEQUENCE DESCRIPTION: SEQ ID NO:26:

```
Cys Ala Arg Arg Tyr Leu Lys Val Asp Phe Ala Asp Ile Gly Trp Ser
1               5                   10                  15

Glu Trp Ile Ile Ser Pro Lys Ser Phe Asp Ala Tyr Tyr Cys Ser Gly
            20              25                  30

Ala Cys Gln Phe Pro Met Pro Lys Ser Leu Lys Pro Ser Asn His Ala
        35                  40                  45

Thr Ile Gln Ser Ile Val Ala Arg Ala Val Gly Val Val Pro Gly Ile
    50                  55                  60

Pro Glu Pro Cys Cys Val Pro Glu Lys Met Ser Ser Leu Ser Ile Leu
65                  70                  75                  80

Phe Phe Asp Glu Asn Lys Asn Val Val Leu Lys Val Tyr Pro Asn Met
                85                  90                  95

Thr Val Glu Ser Cys Ala Cys Arg
            100
```

( 2 ) INFORMATION FOR SEQ ID NO:27:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=BMP5

( x i ) SEQUENCE DESCRIPTION: SEQ ID NO:27:

```
Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Phe Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Leu Met Phe Pro Asp His Val Pro Lys
    50                  55                  60

Pro Cys Cys Ala Pro Thr Lys Leu Asn Ala Ile Ser Val Leu Tyr Phe
65                  70                  75                  80
```

```
              Asp  Asp  Ser  Ser  Asn  Val  Ile  Leu  Lys  Lys  Tyr  Arg  Asn  Met  Val  Val
                             85                      90                      95

Arg  Ser  Cys  Gly  Cys  His
                            100
```

( 2 ) INFORMATION FOR SEQ ID NO:28:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=BMP6

( x i ) SEQUENCE DESCRIPTION: SEQ ID NO:28:

```
              Cys  Arg  Lys  His  Glu  Leu  Tyr  Val  Ser  Phe  Gln  Asp  Leu  Gly  Trp  Gln
              1                    5                      10                     15

Asp  Trp  Ile  Ile  Ala  Pro  Lys  Gly  Tyr  Ala  Ala  Asn  Tyr  Cys  Asp  Gly
                             20                      25                      30

Glu  Cys  Ser  Phe  Pro  Leu  Asn  Ala  His  Met  Asn  Ala  Thr  Asn  His  Ala
                            35                      40                      45

Ile  Val  Gln  Thr  Leu  Val  His  Leu  Met  Asn  Pro  Glu  Tyr  Val  Pro  Lys
                            50                      55                      60

Pro  Cys  Cys  Ala  Pro  Thr  Lys  Leu  Asn  Ala  Ile  Ser  Val  Leu  Tyr  Phe
              65                            70                      75                     80

Asp  Asp  Asn  Ser  Asn  Val  Ile  Leu  Lys  Lys  Tyr  Arg  Trp  Met  Val  Val
                             85                      90                      95

Arg  Ala  Cys  Gly  Cys  His
                            100
```

( 2 ) INFORMATION FOR SEQ ID NO:29:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=OPX
            / note= "WHEREIN XAA AT EACH POS'N IS INDEPENDENTLY
            SELECTED FROM THE RESIDUES OCCURING AT THE CORRESPONDING
            POS'N IN THE C-TERMINAL SEQUENCE OF MOUSE OR HUMAN OP1
            OR OP2 (SEQ. ID NOS. 5,6,7&8 OR 16,18, 20&22"

( x i ) SEQUENCE DESCRIPTION: SEQ ID NO:29:

```
              Cys  Xaa  Xaa  His  Glu  Leu  Tyr  Val  Xaa  Phe  Xaa  Asp  Leu  Gly  Trp  Xaa
              1                    5                      10                     15

Asp  Trp  Xaa  Ile  Ala  Pro  Xaa  Gly  Tyr  Xaa  Ala  Tyr  Tyr  Cys  Glu  Gly
                             20                      25                      30

Glu  Cys  Xaa  Phe  Pro  Leu  Xaa  Ser  Xaa  Met  Asn  Ala  Thr  Asn  His  Ala
                            35                      40                      45

Ile  Xaa  Gln  Xaa  Leu  Val  His  Xaa  Xaa  Xaa  Pro  Xaa  Xaa  Val  Pro  Lys
                            50                      55                      60
```

5,650,276

-continued

```
Xaa  Cys  Cys  Ala  Pro  Thr  Xaa  Leu  Xaa  Ala  Xaa  Ser  Val  Leu  Tyr  Xaa
65                       70                  75                            80

Asp  Xaa  Ser  Xaa  Asn  Val  Xaa  Leu  Xaa  Lys  Xaa  Arg  Asn  Met  Val  Val
                    85                       90                       95

Xaa  Ala  Cys  Gly  Cys  His
                    100
```

(2) INFORMATION FOR SEQ ID NO:30:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label=GENERIC-SEQ-5
        / note= "WHEREIN EACH XAA IS INDEPENDENTLY SELECTED FROM
        A GROUP OF ONE OR MORE SPECIFIED AMINO ACIDS AS DEFINED
        IN THE SPECIFICATION"

(xi) SEQUENCE DESCRIPTION: SEQ ID NO:30:

```
Leu  Xaa  Xaa  Xaa  Phe  Xaa  Xaa  Xaa  Gly  Trp  Xaa  Xaa  Trp  Xaa  Xaa  Xaa
1                    5                        10                            15

Pro  Xaa  Xaa  Xaa  Xaa  Ala  Xaa  Tyr  Cys  Xaa  Gly  Xaa  Cys  Xaa  Xaa  Pro
                    20                   25                            30

Xaa  Xaa  Xaa  Xaa  Xaa  Xaa  Xaa  Xaa  Asn  His  Ala  Xaa  Xaa  Xaa  Xaa  Xaa
               35                        40                       45

Xaa  Xaa  Xaa  Xaa  Xaa  Xaa  Xaa  Xaa  Xaa  Xaa  Xaa  Cys  Cys  Xaa  Pro
          50                             55                       60

Xaa  Xaa  Xaa  Xaa  Xaa  Xaa  Xaa  Leu  Xaa  Xaa  Xaa  Xaa  Xaa  Xaa  Xaa  Xaa
65                       70                       75                         80

Val  Xaa  Leu  Xaa  Xaa  Xaa  Xaa  Xaa  Met  Xaa  Val  Xaa  Xaa  Cys  Xaa  Cys
                    85                        90                       95

Xaa
```

(2) INFORMATION FOR SEQ ID NO:31:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label=GENERIC-SEQ-6
        / note= "WHEREIN EACH XAA IS INDEPENDENTLY SELECTED FROM
        A GROUP OF ONE OR MORE SPECIFIED AMINO ACIDS AS DEFINED
        IN THE SPECIFICATION"

(xi) SEQUENCE DESCRIPTION: SEQ ID NO:31:

```
Cys  Xaa  Xaa  Xaa  Xaa  Leu  Xaa  Xaa  Xaa  Phe  Xaa  Xaa  Xaa  Gly  Trp  Xaa
1                    5                        10                            15

Xaa  Trp  Xaa  Xaa  Xaa  Pro  Xaa  Xaa  Xaa  Xaa  Ala  Xaa  Tyr  Cys  Xaa  Gly
                    20                        25                       30

Xaa  Cys  Xaa  Xaa  Pro  Xaa  Xaa  Xaa  Xaa  Xaa  Xaa  Xaa  Xaa  Asn  His  Ala
          35                             40                       45
```

```
        Xaa Xaa Xaa Xaa Xaa Xaa Xaa Xaa Xaa Xaa Xaa Xaa Xaa Xaa Xaa Xaa
            50                  55                  60

Xaa Cys Cys Xaa Pro Xaa Xaa Xaa Xaa Xaa Xaa Xaa Xaa Leu Xaa Xaa
            65              70                  75                  80

Xaa Xaa Xaa Xaa Xaa Val Xaa Leu Xaa Xaa Xaa Xaa Xaa Met Xaa Val
                        85              90                  95

Xaa Xaa Cys Xaa Cys Xaa
                    100
```

( 2 ) INFORMATION FOR SEQ ID NO:32:

( i ) SEQUENCE CHARACTERISTICS:
        ( A ) LENGTH: 1247 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 84..1199
        ( D ) OTHER INFORMATION: /product="GDF-1"

( x i ) SEQUENCE DESCRIPTION: SEQ ID NO:32:

```
GGGGACACCG  GCCCCGCCCT  CAGCCCACTG  GTCCCGGGCC  GCCGCGGACC  CTGCGCACTC         60

TCTGGTCATC  GCCTGGGAGG  AAG ATG CCA CCG CCG CAG CAA GGT CCC TGC              110
                           Met Pro Pro Pro Gln Gln Gly Pro Cys
                            1               5

GGC CAC CAC CTC CTC CTC CTC CTG GCC CTG CTG CTG CCC TCG CTG CCC              158
Gly His His Leu Leu Leu Leu Leu Ala Leu Leu Leu Pro Ser Leu Pro
 10              15                  20                  25

CTG ACC CGC GCC CCC GTG CCC CCA GGC CCA GCC GCC GCC CTG CTC CAG              206
Leu Thr Arg Ala Pro Val Pro Pro Gly Pro Ala Ala Ala Leu Leu Gln
                 30                  35                  40

GCT CTA GGA CTG CGC GAT GAG CCC CAG GGT GCC CCC AGG CTC CGG CCG              254
Ala Leu Gly Leu Arg Asp Glu Pro Gln Gly Ala Pro Arg Leu Arg Pro
             45                  50                  55

GTT CCC CCG GTC ATG TGG CGC CTG TTT CGA CGC CGG GAC CCC CAG GAG              302
Val Pro Pro Val Met Trp Arg Leu Phe Arg Arg Arg Asp Pro Gln Glu
         60                  65                  70

ACC AGG TCT GGC TCG CGG CGG ACG TCC CCA GGG GTC ACC CTG CAA CCG              350
Thr Arg Ser Gly Ser Arg Arg Thr Ser Pro Gly Val Thr Leu Gln Pro
     75                  80                  85

TGC CAC GTG GAG GAG CTG GGG GTC GCC GGA AAC ATC GTG CGC CAC ATC              398
Cys His Val Glu Glu Leu Gly Val Ala Gly Asn Ile Val Arg His Ile
 90                  95                  100                 105

CCG GAC CGC GGT GCG CCC ACC CGG GCC TCG GAG CCT GTC TCG GCC GCG              446
Pro Asp Arg Gly Ala Pro Thr Arg Ala Ser Glu Pro Val Ser Ala Ala
                 110                 115                 120

GGG CAT TGC CCT GAG TGG ACA GTC GTC TTC GAC CTG TCG GCT GTG GAA              494
Gly His Cys Pro Glu Trp Thr Val Val Phe Asp Leu Ser Ala Val Glu
             125                 130                 135

CCC GCT GAG CGC CCG AGC CGG GCC CGC CTG GAG CTG CGT TTC GCG GCG              542
Pro Ala Glu Arg Pro Ser Arg Ala Arg Leu Glu Leu Arg Phe Ala Ala
         140                 145                 150

GCG GCG GCG GCA GCC CCG GAG GGC GGC TGG GAG CTG AGC GTG GCG CAA              590
Ala Ala Ala Ala Ala Pro Glu Gly Gly Trp Glu Leu Ser Val Ala Gln
     155                 160                 165

GCG GGC CAG GGC GCG GGC GCG GAC CCC GGG CCG GTG CTG CTC CGC CAG              638
Ala Gly Gln Gly Ala Gly Ala Asp Pro Gly Pro Val Leu Leu Arg Gln
 170                 175                 180                 185
```

| | | | | | | | | | | | | | | | | |
|---|---|---|---|---|---|---|---|---|---|---|---|---|---|---|---|---|
| TTG | GTG | CCC | GCC | CTG | GGG | CCG | CCA | GTG | CGC | GCG | GAG | CTG | CTG | GGC | GCC | 686 |
| Leu | Val | Pro | Ala | Leu | Gly | Pro | Pro | Val | Arg | Ala | Glu | Leu | Leu | Gly | Ala | |
| | | | | 190 | | | | 195 | | | | | | 200 | | |
| GCT | TGG | GCT | CGC | AAC | GCC | TCA | TGG | CCG | CGC | AGC | CTC | CGC | CTG | GCG | CTG | 734 |
| Ala | Trp | Ala | Arg | Asn | Ala | Ser | Trp | Pro | Arg | Ser | Leu | Arg | Leu | Ala | Leu | |
| | | | 205 | | | | | 210 | | | | | 215 | | | |
| GCG | CTA | CGC | CCC | CGG | GCC | CCT | GCC | GCC | TGC | GCG | CGC | CTG | GCC | GAG | GCC | 782 |
| Ala | Leu | Arg | Pro | Arg | Ala | Pro | Ala | Ala | Cys | Ala | Arg | Leu | Ala | Glu | Ala | |
| | | 220 | | | | | 225 | | | | | 230 | | | | |
| TCG | CTG | CTG | CTG | GTG | ACC | CTC | GAC | CCG | CGC | CTG | TGC | CAC | CCC | CTG | GCC | 830 |
| Ser | Leu | Leu | Leu | Val | Thr | Leu | Asp | Pro | Arg | Leu | Cys | His | Pro | Leu | Ala | |
| | 235 | | | | | 240 | | | | 245 | | | | | | |
| CGG | CCG | CGG | CGC | GAC | GCC | GAA | CCC | GTG | TTG | GGC | GGC | GGC | CCC | GGG | GGC | 878 |
| Arg | Pro | Arg | Arg | Asp | Ala | Glu | Pro | Val | Leu | Gly | Gly | Gly | Pro | Gly | Gly | |
| 250 | | | | | 255 | | | | | 260 | | | | | 265 | |
| GCT | TGT | CGC | GCG | CGG | CGG | CTG | TAC | GTG | AGC | TTC | CGC | GAG | GTG | GGC | TGG | 926 |
| Ala | Cys | Arg | Ala | Arg | Arg | Leu | Tyr | Val | Ser | Phe | Arg | Glu | Val | Gly | Trp | |
| | | | | 270 | | | | | 275 | | | | | 280 | | |
| CAC | CGC | TGG | GTC | ATC | GCG | CCG | CGC | GGC | TTC | CTG | GCC | AAC | TAC | TGC | CAG | 974 |
| His | Arg | Trp | Val | Ile | Ala | Pro | Arg | Gly | Phe | Leu | Ala | Asn | Tyr | Cys | Gln | |
| | | | 285 | | | | | 290 | | | | | 295 | | | |
| GGT | CAG | TGC | GCG | CTG | CCC | GTC | GCG | CTG | TCG | GGG | TCC | GGG | GGG | CCG | CCG | 1022 |
| Gly | Gln | Cys | Ala | Leu | Pro | Val | Ala | Leu | Ser | Gly | Ser | Gly | Gly | Pro | Pro | |
| | | 300 | | | | | 305 | | | | | 310 | | | | |
| GCG | CTC | AAC | CAC | GCT | GTG | CTG | CGC | GCG | CTC | ATG | CAC | GCG | GCC | GCC | CCG | 1070 |
| Ala | Leu | Asn | His | Ala | Val | Leu | Arg | Ala | Leu | Met | His | Ala | Ala | Ala | Pro | |
| | 315 | | | | | 320 | | | | 325 | | | | | | |
| GGA | GCC | GCC | GAC | CTG | CCC | TGC | TGC | GTG | CCC | GCG | CGC | CTG | TCG | CCC | ATC | 1118 |
| Gly | Ala | Ala | Asp | Leu | Pro | Cys | Cys | Val | Pro | Ala | Arg | Leu | Ser | Pro | Ile | |
| 330 | | | | | 335 | | | | | 340 | | | | | 345 | |
| TCC | GTG | CTC | TTC | TTT | GAC | AAC | AGC | GAC | AAC | GTG | GTG | CTG | CGG | CAG | TAT | 1166 |
| Ser | Val | Leu | Phe | Phe | Asp | Asn | Ser | Asp | Asn | Val | Val | Leu | Arg | Gln | Tyr | |
| | | | | 350 | | | | | 355 | | | | | 360 | | |
| GAG | GAC | ATG | GTG | GTG | GAC | GAG | TGC | GGC | TGC | CGC | TAACCCGGGG | | CGGGCAGGGA | | | 1219 |
| Glu | Asp | Met | Val | Val | Asp | Glu | Cys | Gly | Cys | Arg | | | | | | |
| | | | 365 | | | | | 370 | | | | | | | | |
| CCCGGGCCCA | | ACAATAAATG | | CCGCGTGG | | | | | | | | | | | | 1247 |

( 2 ) INFORMATION FOR SEQ ID NO:33:

( i ) SEQUENCE CHARACTERISTICS:
        ( A ) LENGTH: 372 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

| | | | | | | | | | | | | | | | |
|---|---|---|---|---|---|---|---|---|---|---|---|---|---|---|---|
| Met | Pro | Pro | Pro | Gln | Gln | Gly | Pro | Cys | Gly | His | His | Leu | Leu | Leu | Leu |
| 1 | | | | 5 | | | | 10 | | | | | 15 | | |
| Leu | Ala | Leu | Leu | Leu | Pro | Ser | Leu | Pro | Leu | Thr | Arg | Ala | Pro | Val | Pro |
| | | | 20 | | | | | 25 | | | | 30 | | | |
| Pro | Gly | Pro | Ala | Ala | Ala | Leu | Leu | Gln | Ala | Leu | Gly | Leu | Arg | Asp | Glu |
| | | | 35 | | | | 40 | | | | 45 | | | | |
| Pro | Gln | Gly | Ala | Pro | Arg | Leu | Arg | Pro | Val | Pro | Pro | Val | Met | Trp | Arg |
| | 50 | | | | 55 | | | | | 60 | | | | | |
| Leu | Phe | Arg | Arg | Arg | Asp | Pro | Gln | Glu | Thr | Arg | Ser | Gly | Ser | Arg | Arg |
| 65 | | | | | 70 | | | | 75 | | | | | 80 | |
| Thr | Ser | Pro | Gly | Val | Thr | Leu | Gln | Pro | Cys | His | Val | Glu | Glu | Leu | Gly |
| | | | | 85 | | | | 90 | | | | | 95 | | |

```
Val  Ala  Gly  Asn  Ile  Val  Arg  His  Ile  Pro  Asp  Arg  Gly  Ala  Pro  Thr
               100                 105                      110

Arg  Ala  Ser  Glu  Pro  Val  Ser  Ala  Ala  Gly  His  Cys  Pro  Glu  Trp  Thr
               115                 120                      125

Val  Val  Phe  Asp  Leu  Ser  Ala  Val  Glu  Pro  Ala  Glu  Arg  Pro  Ser  Arg
     130                      135                 140

Ala  Arg  Leu  Glu  Leu  Arg  Phe  Ala  Ala  Ala  Ala  Ala  Ala  Ala  Pro  Glu
145                      150                 155                           160

Gly  Gly  Trp  Glu  Leu  Ser  Val  Ala  Gln  Ala  Gly  Gln  Gly  Ala  Gly  Ala
                    165                      170                      175

Asp  Pro  Gly  Pro  Val  Leu  Leu  Arg  Gln  Leu  Val  Pro  Ala  Leu  Gly  Pro
               180                 185                      190

Pro  Val  Arg  Ala  Glu  Leu  Leu  Gly  Ala  Ala  Trp  Ala  Arg  Asn  Ala  Ser
          195                      200                      205

Trp  Pro  Arg  Ser  Leu  Arg  Leu  Ala  Leu  Ala  Leu  Arg  Pro  Arg  Ala  Pro
     210                      215                 220

Ala  Ala  Cys  Ala  Arg  Leu  Ala  Glu  Ala  Ser  Leu  Leu  Leu  Val  Thr  Leu
225                      230                 235                           240

Asp  Pro  Arg  Leu  Cys  His  Pro  Leu  Ala  Arg  Pro  Arg  Arg  Asp  Ala  Glu
               245                      250                 255

Pro  Val  Leu  Gly  Gly  Gly  Pro  Gly  Gly  Ala  Cys  Arg  Ala  Arg  Arg  Leu
               260                 265                      270

Tyr  Val  Ser  Phe  Arg  Glu  Val  Gly  Trp  His  Arg  Trp  Val  Ile  Ala  Pro
          275                      280                 285

Arg  Gly  Phe  Leu  Ala  Asn  Tyr  Cys  Gln  Gly  Gln  Cys  Ala  Leu  Pro  Val
     290                      295                 300

Ala  Leu  Ser  Gly  Ser  Gly  Gly  Pro  Pro  Ala  Leu  Asn  His  Ala  Val  Leu
305                      310                 315                           320

Arg  Ala  Leu  Met  His  Ala  Ala  Ala  Pro  Gly  Ala  Ala  Asp  Leu  Pro  Cys
               325                      330                 335

Cys  Val  Pro  Ala  Arg  Leu  Ser  Pro  Ile  Ser  Val  Leu  Phe  Phe  Asp  Asn
               340                 345                      350

Ser  Asp  Asn  Val  Val  Leu  Arg  Gln  Tyr  Glu  Asp  Met  Val  Val  Asp  Glu
          355                      360                 365

Cys  Gly  Cys  Arg
          370
```

MORPHOGENIC PROTEIN SCREENING METHOD

This is a continuation of application Ser. No. 07/938,021 filed on Aug. 28, 1992, abandoned, which is a continuation-in-part of U.S. Ser. No. 752,861, and U.S. Ser. No. 752,764, both filed Aug. 30, 1991, both of which are continuations-in-part of U.S. Ser. No. 667,274, filed Mar. 11, 1991, the disclosures of each of which are incorporated herein by reference.

The invention relates to a method of screening drugs for the ability to modulate the level in mammals of proteins which can induce tissue morphogenesis and to methods of determining which animal tissue(s) and/or cell types within a tissue express a particular morphogenic protein.

BACKGROUND OF THE INVENTION

Cell differentiation is the central characteristic of morphogenesis which initiates in the embryo, and continues to various degrees throughout the life of an organism in adult tissue repair and regeneration mechanisms. Members of the TGF-β superfamily include subfamilies of highly-related genes that now are suspected to play important roles in cell differentiation and morphogenesis during development and/or during adult life. For example, the Drosophila decapentaplegic gene product (DPP) has been implicated in formation of the dorsal-ventral axis in fruit flies; activins induce mesoderm and anterior structure formation in mammals; Müllerian inhibiting substance (MIS) may be required for male sex development in mammals; growth/differentiation factor-1 (GDF-1) has been implicated in nerve development and maintenance; other morphogenic proteins (BMP-2, -3, -4 and OP-1) induce bone formation.

The development and study of a bone induction model system has identified the developmental cascade of bone differentiation as consisting of chemotaxis of mesenchymal cells, proliferation of these progenitor cells, differentiation of cartilage, ossification and hypertrophy of this cartilaginous tissue, vascular invasion, bone formation, remodeling, and finally, marrow differentiation (Reddi (1981) *Collagen Rel. Res.* 1:209–206). This bone model system, which is studied in adult mammals, recapitulates the cascade of bone differentiation events that occur in formation of bone in the developing fetus. In other studies, the epithelium of the urinary bladder has been shown to induce new bone formation. Huggins (1931, Arch. Surg. 22:377–408) showed that new bone formation could be induced by surgical transplantation of urinary bladder epithelium onto the parietal fascia. Urist (1965, *Science* 150:893–899) demonstrated that implantation of demineralized bone segments resulted in endochondral bone formation. The latter study and observation suggested the existence of an osteogenic protein and that bovine diaphyseal bone was a source of enriched preparations of osteogenic protein (Sampath et al., *J. Biol. Chem.* 265:13198–13205, 1990; Urist, ibid; Reddi et al., *Proc. Nat. Aca. Sci.* 69:1601–1605, 1972; Sampath et al., *Proc. Natl. Acad. Sci.* 80:6591–6595, 1983). Proteins capable of inducing endochondral bone formation in mammals when implanted in association with a matrix now have been identified in a number of different mammalian species, as have the genes encoding these proteins, (see, for example, U.S. Pat. No. 4,968,590; U.S. Ser. No. 315,342 filed Feb. 23, 1989; and U.S. Ser. No. 599,543, filed Oct. 18, 1990). Human OP-1 DNA has been cloned from various cDNA and genomic libraries using a consensus probe (Ozkaynak et al., *EMBO J.* 9:2085–2093, 1990). Purified human recombinant OP-1, expressed in mammalian cells, has been shown to induce new bone formation in vivo. Like other members of the TGF-β superfamily, OP-1 is produced as a precursor, glycosylated, processed and secreted as a mature dimer. Mature OP-1 is cleaved at a maturation site following a sequence with the pattern of RXXR (Panganiban et al., *Mol. Cell. Biol.* 10:2669–2677, 1990).

The degree of morphogenesis in adult tissue varies among different tissues and depends on, among other factors, the degree of cell turnover in a given tissue. On this basis, tissues can be divided into three broad categories: 1) tissues with static cell populations such as nerve and skeletal muscle where there is little or no cell division and most of the cells formed during development persist throughout adult life and, therefore, possess little or no ability for normal regeneration after injury; 2) tissues containing conditionally renewing populations such as liver where there is generally little cell division but, in response to an appropriate stimulus or injury, cells can divide to produce daughters of the same differentiated cell type; and 3) tissues with permanently renewing populations including blood, bone, testes, and stratified squamous epithelia which are characterized by rapid and continuous cell turnover in the adult. Here, the terminally differentiated cells have a short life span and are replaced through proliferation of a distinct subpopulation of cells, known as stem or progenitor cells.

It is an object of this invention to provide a method of screening compounds which, when administered to a given tissue from a given organism, cause an alteration in the level of morphogenic protein ("morphogen") produced by the tissue. Such compounds, when administered systemically, will result in altered systemic or local levels of morphogenic activity. This morphogenic activity includes the ability to induce proliferation and sequential differentiation of progenitor cells, and the ability to support and maintain the differentiated phenotype or sequence of phenotypes through the progression of events that results in the formation of normal adult tissue (including organ regeneration). Thus, broadly, the invention provides a key to development of additional modalities of therapies involving modulation of morphogenic protein production in animals or adult mammals, e.g., humans, and consequent correction of conditions involving pathologic alteration of the balance of tissue cell turnover. Another object of the invention is to provide methodologies for identifying or selecting a combination of compound(s) which may increase a progenitor cell population in a mammal, stimulate progenitor cells to differentiate in vivo or in vitro, maintain the differentiated phenotype or sequence of phenotypes of a tissue, induce tissue-specific growth in vivo, or replace diseased or damaged tissues or organs in vivo. Another object of the invention is to determine the tissue(s) or organ(s) of origin of a given morphogen. Another object of the invention is to determine the specific cell type(s) within the tissue(s) or organ(s) of origin, or cell line(s) derived from the tissue(s), or organ(s) of origin, that is responsible for the synthesis and production of a given morphogen. These and other objects and features of the invention will be apparent from the description, drawing, and claims which follow.

SUMMARY OF THE INVENTION

The invention features a method of screening candidate compounds for the ability to modulate the effective local or systemic concentration or level of morphogenic protein in an organism. The method is practiced by incubating one or more candidate compound(s) with cells from a test tissue type of an organism known to produce a given morphogen for a time sufficient to allow the compound(s) to affect the production, i.e., expression and/or secretion, of morphogen by the cells; and then assaying cells and the medium conditioned by the cells for a change in a parameter indicative of the level of production of the morphogenic protein. The procedure may be used to identify compounds showing promise as drugs for human use capable of increasing or decreasing morphogen production in vivo, thereby to correct or alleviate a diseased condition.

In a related aspect, the invention features a method of screening tissue(s) of an organism to assess whether or at what level cells of the tissue(s) produce a particular morphogen, thereby to determine a tissue(s) of origin of the morphogen. This permits selection of the tissue cell type to be used in the screening. As used herein, "tissue" refers to a group of cells which are naturally found associated, including an organ.

As an example of tissue(s) or organ(s) which produce high levels of morphogen relative to the level produced by other types of tissues, it has been discovered that OP-1, first found in bone tissue is produced at relatively high levels in cells derived from renal, e.g., kidney or bladder, or adrenal tissue; that GDF-1 is produced at relatively high levels in cells derived from nerve, e.g., brain tissue; that DPP is produced at relatively high levels in cells derived from one of the following drosophila tissues: dorsal ectoderm, epithelial imaginal disc, visceral mesoderm, or gut endoderm; that Vgr-1 is produced at relatively high levels in cells derived from mouse lung tissue; and that Vgl is produced at relatively high levels in cells derived from xenopus fetal endoderm tissue. In addition, BMP3 and CBMP2B transcripts have been identified in abundance in lung tissue. As used herein, "derived" means the cells are the cultured tissue itself, or are a cell line whose parent cells are the tissue itself.

Preferred methods for determining the level of or a change in the level of a morphogen in a cultured cell include using an antibody specific for the morphogen, e.g., in an immunoassay such as an ELISA or radioimmunoassay; and determining the level of nucleic acid, most particularly mRNA, encoding the morphogen using a nucleic acid probe that hybridizes under stringent conditions with the morphogen RNA, such as in an RNA dot blot analysis. Where a change in the presence and/or concentration of morphogen is being determined, it will be necessary to measure and compare the levels of morphogen in the presence and absence of the candidate compound. The nucleic acid probe may be a nucleotide sequence encoding the morphogen or a fragment large enough to hybridize specifically only to RNA encoding a specific morphogen under stringent conditions. As used herein, "stringent conditions" are defined as conditions in which non-specific hybrids will be eluted but at which specific hybrids will be maintained, i.e., incubation at 0.1X SSC (15 mM NaCl, 5 mM Na citrate) at 50° C. for 15 minutes.

Examples of morphogens whose levels may be determined according to the invention include OP-1, OP-2, GDF-1, Vgr-1, DPP, 60A, CBMP2A, CBMP2B, BMP 2, 3, 4, 5, 6, or Vgl. Thus, if an immunoassay is used to indicate the presence and/or concentration of a morphogen, an antibody specific for one of these morphogens only, and which will not detect the presence of other morphogens, will be used. Similarly, if nucleic acid hybridization is used to indicate the level of RNA encoding the morphogen, a nucleotide probe specific for one of these morphogens only will be used under hybridization conditions such that the probe should not be capable of hybridizing with RNA encoding a different morphogen. A morphogen includes an active C-terminal core region, which includes at least six cysteine residues, and a region N-terminal to the C-terminal region that is relatively non-homologous to the equivalent N-terminal regions of other morphogens. In addition, the 3' noncoding region of the mRNA is unique to each morphogen. Thus, a nucleic acid probe encoding all or a portion of the sequences N-terminal to the C-terminal core region of a morphogen, or encoding all or a portion of the sequences C-terminal to or 3' to the core region of a morphogen may be used as a probe which detects mRNA encoding that morphogen only.

"Morphogenic proteins" or "morphogens", as used herein, include naturally-occurring osteogenic proteins capable of inducing the full developmental cascade of bone formation, as well as polypeptide chains not normally associated with bone or bone formation, but sharing substantial sequence homology with osteogenic proteins. Such proteins, as well as DNA sequences encoding them, have been isolated and characterized for a number of different species. See, for example, U.S. Pat. No. 4,968,590 and U.S. Pat. No. 5,011,691, U.S. application Ser. No. 1989; 422,699, filed Oct.17, 1989, and 600,024 and 599,543, both filed Oct. 18, 1990; Sampath et al., (1990) *J. Biol. Chem.* 265:13198–13205; Ozkaynak et al. (1990) *EMBO J.* 9:2085–2093; and Lee, *Proc. Nat. Aca. Sci.* 88:42504254 (1991), all of which are hereby incorporated by reference. Many of these proteins subsequently were discovered to have utility beyond bone morphogenesis. See, e.g., U.S. Ser. No. 667,274 filed Mar. 11, 1991. The mature forms of morphogens share substantial amino acid sequence homology, especially in the C-terminal core regions of the proteins. In particular, most of the proteins share a seven-cysteine skeleton in this region, in addition to other apparently required amino acids. Table II, infra, shows the amino acid sequence homologies for nine morphogens over the carboxy terminal 102 amino acids.

Among the morphogens useful in this invention are proteins originally identified as osteogenic proteins, such as the OP-1, OP-2 and CBMP2 proteins, as well as amino acid sequence-related proteins such as DPP (from Drosophila), Vgl (from Xenopus), Vgr-1 (from mouse, see U.S. Pat. No. 5,011,691 to Oppermann et al.), GDF-1 (from mouse, see Lee (1991) PNAS 88:4250–4254), all of which are presented in Table II and Seq. ID Nos.5-14), and the recently identified 60A protein (from Drosophila, Seq. ID No. 24, see Wharton et al. (1991) PNAS 88:9214-9218.) The members of this family, which include members of the TGF-β superfamily of proteins, share substantial amino acid sequence homology in their C-terminal regions. The proteins are translated as a precursor, having an N-terminal signal peptide sequence, typically less than about 30 residues, followed by a "pro" domain that is cleaved to yield the mature sequence. The signal peptide is cleaved rapidly upon translation, at a cleavage site that can be predicted in a given sequence using the method of Von Heijne ((1986) *Nucleic Acids Research* 14:4683–4691.) Table I, below, describes the various morphogens identified to date, including their nomenclature as used herein, their Seq. ID references, and publication sources for the amino acid sequences for the full length proteins not included in the Seq. Listing. The disclosure of these publications is incorporated herein by reference.

TABLE I

"OP-1" refers generically to the group of morphogenically active proteins expressed from part or all of a DNA sequence encoding OP-1 protein, including allelic and species variants thereof, e.g., human OP-1 ("hOP-1", Seq. ID No. 5, mature protein amino acid sequence), or mouse OP-1 ("mOP-1", Seq. ID No. 6, mature protein amino acid sequence.) The conserved seven cysteine skeleton is defined by residues 38 to 139 of Seq. ID Nos. 5 and 6. The cDNA sequences and the amino acids encoding the full length proteins are provided in Seq. Id Nos. 16 and 17 (hOP1) and Seq. ID Nos. 18 and 19 (mOP1.) The mature proteins are defined by residues 293-431 (hOP1) and 292-430 (mOP1). The "pro" regions of the proteins, cleaved to yield the mature, morphogenically active proteins are defined essentially by residues 30-292 (hOP1) and residues 30-291 (mOP1).

"OP-2" refers generically to the group of active proteins expressed from part or all of a DNA sequence encoding OP-2 protein, including allelic and species variants thereof, e.g., human OP-2 ("hOP-2", Seq. ID No. 7, mature protein amino acid sequence) or mouse OP-2 ("mOP-2", Seq. ID No. 8, mature protein amino acid sequence). The conserved seven cysteine skeleton is defined by residues 38 to 139 of Seq. ID Nos. 7 and 8. The cDNA sequences and the amino acids encoding the full length proteins are provided in Seq. ID Nos. 20 and 21 (hOP2) and Seq. ID Nos. 22 and 23 (mOP2.) The mature proteins are defined essentially by residues 264-402 (hOP2) and 261-399 (mOP2). The "pro" regions of the proteins, cleaved to yield the mature, morphogenically active proteins likely are defined essentially by residues 18-263 (hOP2) and residues 18-260 (mOP2). (Another cleavage site also occurs 21 residues upstream for both OP-2 proteins.)

"CBMP2" refers generically to the morphogenically active proteins expressed from a part or all of a DNA sequence encoding the CBMP2 proteins, including allelic and species variants thereof, e.g., human CBMP2A ("CBMP2A(fx)", Seq ID No. 9) or human CBMP2B DNA ("CBMP2B(fx)", Seq. ID No. 10). The amino acid sequence for the full length proteins, referred to in the literature as BMP2A and BMP2B, or BMP2 and BMP4, appear in Wozney, et al. (1988) *Science* 242:1528-1534. The pro domain for BMP2 (BMP2A) likely includes residues 25-248 or 25-282; the mature protein, residues 249-396 or 283-396. The pro domain for BMP4 (BMP2B) likely includes residues 25-256 or 25-292; the mature protein, residues 257-408 or 293-408.

"DPP(fx)" refers to protein sequences encoded by the Drosophila DPP gene and defining the conserved seven cysteine skeleton (Seq. ID No. 11). The amino acid sequence for the full length protein appears in Padgett, et al (1987) *Nature* 325: 81-84. The pro domain likely extends from the signal peptide cleavage site to residue 456; the mature protein likely is defined by residues 457-588.

"Vgl(fx)" refers to protein sequences encoded by the Xenopus Vgl gene and defining the conserved seven cysteine skeleton (Seq. ID No. 12). The amino acid sequence for the full length protein appears in Weeks (1987) *Cell* 51: 861-867. The pro domain likely extends from the signal peptide cleavage site to residue 246; the mature protein likely is defined by residues 247-360.

"Vgr- 1 ( fx )" refers to protein sequences encoded by the murine Vgr-1 gene and defining the conserved seven cysteine skeleton (Seq. ID No. 13). The amino acid sequence for the full length protein appears in Lyons, et al, (1989) *PNAS* 86: 4554-4558. The pro domain likely extends from the signal peptide cleavage site to residue 299; the mature protein likely is defined by residues 300-438.

"GDF-1(fx)" refers to protein sequences encoded by the human GDF-1 gene and defining the conserved seven cysteine skeleton (Seq. ID No. 14). The cDNA and encoded amino sequence for the full length protein is provided in Seq. ID. No. 32. The pro domain likely extends from the signal peptide cleavage site to residue 214; the mature protein likely is defined by residues 215-372.

"60A" refers generically to the morphogenically active proteins expressed from part or all of a DNA sequence (from the Drosophila 60A gene) encoding the 60A proteins (see Seq. ID No. 24 wherein the cDNA and encoded amino acid sequence for the full length protein is provided). "60A(fx)" refers to the protein sequences defining the conserved seven cysteine skeleton (residues 354 to 455 of Seq. ID No. 24.) The pro domain likely extends from the signal peptide cleavage site to residue 324; the mature protein likely is defined by residues 325-455.

"BMP3(fx)" refers to protein sequences encoded by the human BMP3 gene and defining the conserved seven cysteine skeleton (Seq. ID No. 26). The amino acid sequence for the full length protein appears in Wozney et al. (1988) *Science* 242: 1528-1534. The pro domain likely extends from the signal peptide cleavage site to residue 290; the mature protein likely is defined by residues 291-472.

"BMP5(fx)" refers to protein sequences encoded by the human BMP5 gene and defining the conserved seven cysteine skeleton (Seq. ID No. 27). The amino acid sequence for the full length protein appears in Celeste, et al. (1991) *PNAS* 87: 9843-9847. The pro domain likely extends from the signal peptide cleavage site to residue 316; the mature protein likely is defined by residues 317-454.

"BMP6(fx)" refers to protein sequences encoded by the human BMP6 gene and defining the conserved seven cysteine skeleton (Seq. ID No. 28). The amino acid sequence for the full length protein appear sin Celeste, et al. (1990) *PNAS* 87: 9843–5847. The pro domain likely includes extends from the signal peptide cleavage site to residue 374; the mature sequence likely includes residues 375-513.

The OP-2 proteins have an additional cysteine residue in this region (e.g., see residue 41 of Seq. ID Nos. 7 and 8), in addition to the conserved cysteine skeleton in common with the other proteins in this family. The GDF-1 protein has a four amino acid insert within the conserved skeleton (residues 44-47 of Seq. ID No. 14) but this insert likely does not interfere with the relationship of the cysteines in the folded structure. In addition, the CBMP2 proteins are missing one amino acid residue within the cysteine skeleton.

The morphogens are inactive when reduced, but are active as oxidized homodimers and when oxidized in combination with other morphogens of this invention. Thus, as defined herein, a morphogen is a dimeric protein comprising a pair of polypeptide chains, wherein each polypeptide chain comprises at least the C-terminal six cysteine skeleton defined by residues 43-139 of Seq. ID No. 5, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- and inter-chain disulfide bonds such that the protein is capable of acting as a morphogen as defined herein. Specifically, the morphogens generally are capable of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. In addition, it is also anticipated that these morphogens are capable of inducing redifferentiation of committed cells under appropriate environmental conditions.

Morphogens useful in this invention comprise one of two species of generic amino acid sequences: Generic Sequence 1 (Seq. ID No. 1) or Generic Sequence 2 (Seq. ID No. 2); where each Xaa indicates one of the 20 naturally-occurring L-isomer, α-amino acids or a derivative thereof. Generic Sequence 1 comprises the conserved six cysteine skeleton and Generic Sequence 2 comprises the conserved six cysteine skeleton plus the additional cysteine identified in OP-2 (see residue 36, Seq. ID No. 2). In another preferred aspect, these sequences further comprise the following additional sequence at their N-terminus:

```
Cys Xaa Xaa Xaa Xaa   (Seq. ID No. 15)
 1            5
```

Preferred amino acid sequences within the foregoing generic sequences include: Generic Sequence 3 (Seq. ID No. 3), Generic Sequence 4 (Seq. ID No. 4), Generic Sequence 5 (Seq. ID No. 30) and Generic Sequence 6 (Seq. ID No. 31), listed below. These Generic Sequences accommodate the homologies shared among the various preferred members of this morphogen family identified in Table II, as well as the amino acid sequence variation among them. Specifically, Generic Sequences 3 and 4 are composite amino acid sequences of the following proteins presented in Table II and identified in Seq. ID Nos. 5-14: human OP-1 (hOP-1, Seq. ID Nos. 5 and 16-17), mouse OP-1 (mOP-1, Seq. ID Nos. 6 and 18-19), human and mouse OP-2 (Seq. ID Nos. 7, 8, and 20-22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14.) The generic sequences include both the amino acid identity shared by the sequences in Table II, as well as alternative residues for the variable positions within the sequence. Note that these generic sequences allow for an additional cysteine at position 41 or 46 in Generic Sequences 3 or 4, respectively, providing an appropriate cysteine skeleton where inter- or intramolecular disulfide bonds can form, and contain certain critical amino acids which influence the tertiary structure of the proteins.

```
             Generic Sequence 3
  Leu Tyr Val Xaa Phe
   1            5
  Xaa Xaa Xaa Gly Trp Xaa Xaa Trp Xaa
                  10
  Xaa Ala Pro Xaa Gly Xaa Xaa Ala
   15               20
```

```
             Generic Sequence 3
                -continued
  Xaa Tyr Cys Xaa Gly Xaa Cys Xaa
          25                30
  Xaa Pro Xaa Xaa Xaa Xaa Xaa
                  35
  Xaa Xaa Xaa Asn His Ala Xaa Xaa
              40              45
  Xaa Xaa Leu Xaa Xaa Xaa Xaa Xaa
                  50
  Xaa Xaa Xaa Xaa Xaa Xaa Xaa Cys
       55                  60
  Cys Xaa Pro Xaa Xaa Xaa Xaa Xaa
                  65
  Xaa Xaa Xaa Leu Xaa Xaa Xaa
   70                   75
  Xaa Xaa Xaa Xaa Val Xaa Leu Xaa
                  80
  Xaa Xaa Xaa Xaa Met Xaa Val Xaa
   85               90
  Xaa Cys Gly Cys Xaa    (Seq. ID No. 3)
           95
``` wherein each Xaa is independently selected from a group of one or more specified amino acids defined as follows: "Res." means "residue" and Xaa at res.4=(Ser, Asp or Glu); Xaa at res.6=(Arg, Gln, Ser or Lys); Xaa at res.7=(Asp or Glu); Xaa at res.8=(Leu or Val); Xaa at res.11=(Gln, Leu, Asp, His or Asn); Xaa at res.12= (Asp, Arg or Asn); Xaa at res.14=(Ile or Val); Xaa at res.15=(Ile or Val); Xaa at res.18=(Glu, Gln, Leu, Lys, Pro or Arg); Xaa at res.20=(Tyr or Phe); Xaa at res.21= (Ala, Set, Asp, Met, His, Leu or Gln); Xaa at res.23= (Tyr, Asn or Phe); Xaa at res.26=(Glu, His, Tyr, Asp or Gln); Xaa at res.28=(Glu, Lys, Asp or Gln); Xaa at res.30=(Ala, Ser, Pro or Gln); Xaa at res.31=(Phe, Leu or Tyr); Xaa at res.33=(Leu or Val); Xaa at res.34= (Asn, Asp, Ala or Thr); Xaa at res.35=(Set, Asp, Glu, Leu or Ala); Xaa at res.36=(Tyr, Cys, His, Ser or Ile); Xaa at res.37=(Met, Phe, Gly or Leu); Xaa at res.38= (Asn or Ser); Xaa at res.39=(Ala, Ser or Gly); Xaa at res.40=(Thr, Leu or Ser); Xaa at res.44=(Ile or Val); Xaa at res.45=(Val or Leu); Xaa at res.46=(Gln or Arg); Xaa at res.47=(Thr, Ala or Set); Xaa at res.49=(Val or Met); Xaa at res.50=(His or Asn); Xaa at res.51=(Phe, Leu, Ash, Ser, Ala or Val); Xaa at res.52=(Ile, Met, Asn, Ala or Val); Xaa at res.53=(Asn, Lys, Ala or Glu); Xaa at res.54=(Pro or Ser); Xaa at res.55=(Glu, Asp, Asn, or Gly); Xaa at res.56=(Thr, Ala, Val, Lys, Asp, Tyr, Ser or Ala); Xaa at res.57=(Val, Ala or Ile); Xaa at res.58=(Pro or Asp); Xaa at res.59=(Lys or Leu); Xaa at res.60=(Pro or Ala); Xaa at res.63=(Ala or Val); Xaa at res.65=(Thr or Ala); Xaa at res.66=(Gln, Lys, Arg or Glu); Xaa at res.67=(Leu, Met or Val); Xaa at res.68=(Asn, Ser or Asp); Xaa at res.69=(Ala, Pro or Ser); Xaa at res.70= (Ile, Thr or Val); Xaa at res.71=(Ser or Ala); Xaa at res.72=(Val or Met); Xaa at res.74=(Tyr or Phe); Xaa at res.75=(Phe, Tyr or Leu); Xaa at res.76=(Asp or Asn); Xaa at res.77=(Asp, Glu, Asn or Ser); Xaa at res.78= (Ser, Gln, Asn or Tyr); Xaa at res.79=(Ser, Asn, Asp or Glu); Xaa at res.80=(Asn, Thr or Lys); Xaa at res.82= (Ile or Val); Xaa at res.84=(Lys or Arg); Xaa at res.85= (Lys, Asn, Gln or His); Xaa at res.86=(Tyr or His); Xaa at res.87=(Arg, Gln or Glu); Xaa at res.88=(Asn, Glu or Asp); Xaa at res.90=(Val, Thr or Ala); Xaa at res.92=(Arg, Lys, Val, Asp or Glu); Xaa at res.93=(Ala, Gly or Glu); and Xaa at res.97=(His or Arg);

Generic Sequence 4

Cys Xaa Xaa Xaa Xaa Leu Tyr Val Xaa Phe
1              5                    10

Xaa Xaa Xaa Gly Trp Xaa Xaa Trp Xaa
              15

Xaa Ala Pro Xaa Gly Xaa Xaa Ala
20                25

Xaa Tyr Cys Xaa Gly Xaa Cys Xaa
        30                  35

Xaa Pro Xaa Xaa Xaa Xaa Xaa
              40

Xaa Xaa Xaa Asn His Ala Xaa Xaa
        45                  50

Xaa Xaa Leu Xaa Xaa Xaa Xaa Xaa
              55

Xaa Xaa Xaa Xaa Xaa Xaa Xaa Cys
    60                      65

Cys Xaa Pro Xaa Xaa Xaa Xaa Xaa
            70

Xaa Xaa Xaa Leu Xaa Xaa Xaa
75              80

Xaa Xaa Xaa Xaa Val Xaa Leu Xaa
            85

Xaa Xaa Xaa Xaa Met Xaa Val Xaa
90                  95

Xaa Cys Gly Cys Xaa  (Seq. ID No. 4)
        100 wherein each Xaa is independently selected from a group of one or more specified amino acids as defined by the following: "Res." means "residue" and Xaa at res.2=(Lys or Arg); Xaa at res.3=(Lys or Arg); Xaa at res.4=(His or Arg); Xaa at res.5=(Glu, Ser, His, Gly, Arg or Pro); Xaa at res.9=(Ser, Asp or Glu); Xaa at res.11=(Arg, Gln, Ser or Lys); Xaa at res.12=(Asp or Glu); Xaa at res.13=(Leu or Val); Xaa at res.16=(Gln, Leu, Asp, His or Asn); Xaa at res.17 =(Asp, Arg, or Asn); Xaa at res.19=(Ile or Val); Xaa at res.20=(Ile or Val); Xaa at res.23=(Glu, Gln, Leu, Lys, Pro or Arg); Xaa at res.25=(Tyr or Phe); Xaa at res.26=(Ala, Ser, Asp, Met, His, Leu, or Gln); Xaa at res.28=(Tyr, Asn or Phe); Xaa at res.31=(Glu, His, Tyr, Asp or Gln); Xaa at res.33=Glu, Lys, Asp or Gln); Xaa at res.35=(Ala, Set or Pro); Xaa at res.36=(Phe, Leu or Tyr); Xaa at res.38=(Leu or Val); Xaa at res.39=(Asn, Asp, Ala or Thr); Xaa at res.40=(Ser, Asp, Glu, Leu or Ala); Xaa at res.41=(Tyr, Cys, His, Ser or Ile); Xaa at res.42=(Met, Phe, Gly or Leu); Xaa at res.44=(Ala, Ser or Gly); Xaa at res.45=(Thr, Leu or Ser); Xaa at res.49=(Ile or Val); Xaa at res.50=(Val or Leu); Xaa at res.51=(Gln or Arg); Xaa at res.52 =(Thr, Ala or Ser); Xaa at res.54=(Val or Met); Xaa at res.55=(His or Asn); Xaa at res.56=(Phe, Leu, Asn, Ser, Ala or Val); Xaa at res.57=(Ile, Met, Asn, Ala or Val); Xaa at res.58=(Asn, Lys, Ala or Glu); Xaa at res.59=(Pro or Set); Xaa at res.60=(Glu, Asp, or Gly); Xaa at res.61=(Thr, Ala, Val, Lys, Asp, Tyr, Set or Ala); Xaa at res.62=(Val, Ala or Ile); Xaa at res.63=(Pro or Asp); Xaa at res.64=(Lys or Leu); Xaa at res.65=(Pro or Ala); Xaa at res.68=(Ala or Val); Xaa at res.70=(Thr or Ala); Xaa at res.71=(Gln, Lys, Arg or Glu); Xaa at res.72=(Leu, Met or Val); Xaa at res.73=(Asn, Ser or Asp); Xaa at res.74=(Ala, Pro or Ser); Xaa at res.75=(Ile, Thr or Val); Xaa at res.76=(Ser or Ala); Xaa at res.77=(Val or Met); Xaa at res.79=(Tyr or Phe); Xaa at res.80=(Phe, Tyr or Leu); Xaa at res.81=(Asp or Asn); Xaa at res.82=(Asp, Glu, Asn or Ser); Xaa at res.83=(Ser, Gln, Asn or Tyr); Xaa at res.84=(Ser, Asn, Asp or Glu); Xaa at res.85=(Asn, Thr or Lys); Xaa at res.87=(Ile or Val); Xaa at res.89=(Lys or Arg); Xaa at res.90=(Lys, Ash, Gln or His); Xaa at res.91=(Tyr or His); Xaa at res.92=(Arg, Gln or Glu); Xaa at res.93=(Asn, Glu or Asp); Xaa at res.95=(Val, Thr or Ala); Xaa at res.97=(Arg, Lys, Val, Asp or Glu); Xaa at res.98=(Ala, Gly or Glu); and Xaa at res.102=(His or Arg).

Similarly, Generic Sequence 5 (Seq. ID No. 30) and Generic Sequence 6 (Seq. ID No. 31) accommodate the homologies shared among all the morphogen protein family members identified in Table II. Specifically, Generic Sequences 5 and 6 are composite amino acid sequences of human OP-1 (hOP-1, Seq. ID Nos. 5 and 16-17), mouse OP-1 (mOP-1, Seq. ID Nos. 6 and 18-19), human and mouse OP-2 (Seq. ID Nos. 7, 8, and 20-22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14), human BMP3 (Seq. ID No. 26), human BMP5 (Seq. ID No. 27), human BMP6 (Seq. ID No. 28) and 60(A) (from Drosophila, Seq. ID Nos. 24-25). The generic sequences include both the amino acid identity shared by these sequences in the C-terminal domain, defined by the six and seven cysteine skeletons (Generic Sequences 5 and 6, respectively), as well as alternative residues for the variable positions within the sequence. As for Generic Sequences 3 and 4, Generic Sequences 5 and 6 allow for an additional cysteine at position 41 (Generic Sequence 5) or position 46 (Generic Sequence 6), providing an appropriate cysteine skeleton where inter- or intramolecular disulfide bonds can form, and containing certain critical amino acids which influence the tertiary structure of the proteins.

Generic Sequence 5

Leu Xaa Xaa Xaa Phe
1               5

Xaa Xaa Xaa Gly Trp Xaa Xaa Trp Xaa
              10

Xaa Xaa Pro Xaa Xaa Xaa Xaa Ala
15                  20

Xaa Tyr Cys Xaa Gly Xaa Cys Xaa
        25                  30

Xaa Pro Xaa Xaa Xaa Xaa Xaa
              35

Xaa Xaa Xaa Asn His Ala Xaa Xaa
        40                  45

Xaa Xaa Xaa Xaa Xaa Xaa Xaa
              50

Xaa Xaa Xaa Xaa Xaa Xaa Xaa Cys
    55                      60

Cys Xaa Pro Xaa Xaa Xaa Xaa Xaa
            65

Xaa Xaa Xaa Leu Xaa Xaa Xaa
70              75

Xaa Xaa Xaa Xaa Val Xaa Leu Xaa
            80

Generic Sequence 5

Xaa Xaa Xaa Xaa Met Xaa Val Xaa
85                  90

Xaa Cys Xaa Cys Xaa   (Seq. ID No. 30)
        95 wherein each Xaa is independently selected from a group of one or more specified amino acids defined as follows: "Res." means "residue" and Xaa at res.2=(Tyr or Lys); Xaa at res.3=(Val or Ile); Xaa at res.4=(Ser, Asp or Glu); Xaa at res.6=(Arg, Gln, Ser, Lys or Ala); Xaa at res.7=(Asp, Glu or Lys); Xaa at res.8=(Leu, Val or Ile); Xaa at res.11=(Gln, Leu, Asp, His, Asn or Ser); Xaa at res.12=(Asp, Arg, Asn or Glu); Xaa at res.14=(Ile or Val); Xaa at res.15 =(Ile or Val); Xaa at res.16 (Ala or Set); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln or Set); Xaa at res.28=(Glu, Lys, Asp, Gln or Ala); Xaa at res.30=(Ala, Set, Pro, Gln or Asn); Xaa at res.31=(Phe, Leu or Tyr); Xaa at res.33=(Leu, Val or Met); Xaa at res.34=(Ash, Asp, Ala, Thr or Pro); Xaa at res.35= (Ser, Asp, Glu, Leu, Ala or Lys); Xaa at res.36=(Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40=(Thr, Leu or Set); Xaa at res.44=(Ile, Val or Thr); Xaa at res.45=(Val, Leu or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Ash, Ser, Ala or Val); Xaa at res.52=(Ile, Met, Asn, Ala, Val or Leu); Xaa at res.53= (Asn, Lys, Ala, Glu, Gly or Phe); Xaa at res.54=(Pro, Set or Val); Xaa at res.55=(Glu, Asp, Asn, Gly, Val or Lys); Xaa at res.56=(Thr, Ala, Val, Lys, Asp, Tyr, Ser, Ala, Pro or His); Xaa at res.57=(Val, Ala or Ile); Xaa at res.58=(Pro or Asp); Xaa at res.59=(Lys, Leu or Glu); Xaa at res.60=(Pro or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Ash, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Met or Ile); Xaa at res.74=(Tyr or Phe); Xaa at res.75(Phe, Tyr, Leu or His); Xaa at res-76=(Asp, Asn or Leu); Xaa at res.77=(Asp, Glu, Ash or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His or Val); Xaa at res.86=(Tyr or His); Xaa at res.87=(Arg, Gln, Glu or Pro); Xaa at res.88=(Asn, Glu or Asp); Xaa at res.90=(Val, Thr, Ala or Ile); Xaa at res.92=(Arg, Lys, Val, Asp or Glu); Xaa at res.93=(Ala, Gly, Glu or Ser); Xaa at res.95=(Gly or Ala) and Xaa at res.97=(His or Arg).

Generic Sequence 6

Cys Xaa Xaa Xaa Xaa Leu Xaa Xaa Xaa Phe
1               5                    10

Xaa Xaa Xaa Gly Trp Xaa Xaa Trp Xaa
                15

Xaa Xaa Pro Xaa Xaa Xaa Xaa Ala
20              25

Xaa Tyr Cys Xaa Gly Xaa Cys Xaa
        30              35

Xaa Pro Xaa Xaa Xaa Xaa Xaa
              40

Xaa Xaa Xaa Asn His Ala Xaa Xaa
            45              50

Xaa Xaa Xaa Xaa Xaa Xaa Xaa
                55

Xaa Xaa Xaa Xaa Xaa Xaa Cys
        60              65

Cys Xaa Pro Xaa Xaa Xaa Xaa Xaa
            70

Xaa Xaa Xaa Leu Xaa Xaa Xaa
75                  80

Xaa Xaa Xaa Xaa Val Xaa Leu Xaa
                85

Xaa Xaa Xaa Xaa Met Xaa Val Xaa
90                  95

Xaa Cys Xaa Cys Xaa   (Seq. ID No. 31)
        100 wherein each Xaa is independently selected from a group of one or more specified amino acids as defined by the following: "Res." means "residue" and Xaa at res.2=(Lys, Arg, Ala or Gln); Xaa at res.3=(Lys, Arg or Met); Xaa at res.4=(His, Arg or Gln); Xaa at res.5=(Glu, Ser, His, Gly, Arg, Pro, Thr, or Tyr); Xaa at res.7=(Tyr or Lys); Xaa at res.8=(Val or Ile); Xaa at res.9=(Ser, Asp or Glu); Xaa at res.11=(Arg, Gln, Ser, Lys or Ala); Xaa at res.12=(Asp, Glu, or Lys); Xaa at res.13=(Leu, Val or Ile); Xaa at res.16=(Gln, Leu, Asp, His, Asn or Ser); Xaa at res.17 =(Asp, Arg, Asn or Glu); Xaa at res.19=(Ile or Val); Xaa at res.20=(Ile or Val); Xaa at res.21=(Ala or Ser); Xaa at res.23=(Glu, Gln, Leu, Lys, Pro or Arg); Xaa at res.24=(Gly or Ser); Xaa at res.25=(Tyr or Phe); Xaa at res.26=(Ala, Ser, Asp, Met, His, Gln, Leu, or Gly); Xaa at res.28=(Tyr, Asn or Phe); Xaa at res.31=(Glu, His, Tyr, Asp, Gln or Ser); Xaa at res.33=(Glu, Lys, Asp, Gln or Ala); Xaa at res.35=(Ala, Ser, Pro, Gln or Asn); Xaa at res.36=(Phe, Leu or Tyr); Xaa at res.38=(Leu, Val or Met); Xaa at res.39=(Asn, Asp, Ala, Thr or Pro); Xaa at res.40= (Ser, Asp, Glu, Leu, Ala or Lys); Xaa at res.41=(Tyr, Cys, His, Set or Ile); Xaa at res.42=(Met, Phe, Gly or Leu); Xaa at res.43=(Asn, Ser or Lys); Xaa at res.44=(Ala, Ser, Gly or Pro); Xaa at res.45=(Thr, Leu or Ser); Xaa at res.49=(Ile, Val or Thr); Xaa at res.50=(Val, Leu or Ile); Xaa at res.51=(Gln or Arg); Xaa at res.52=(Thr, Ala or Ser); Xaa at res.53=(Leu or Ile); Xaa at res.54=(Val or Met); Xaa at res.55=(His, Asn or Arg); Xaa at res.56=(Phe, Leu, Asn, Ser, Ala or Val); Xaa at res.57=(Ile, Met, Asn, Ala, Val or Leu); Xaa at res.58= (Asn, Lys, Ala, Glu, Gly or Phe); Xaa at res.59=(Pro, Ser or Val); Xaa at res.60=(Glu, Asp, Gly, Val or Lys); Xaa at res.61=(Thr, Ala, Val, Lys, Asp, Tyr, Ser, Ala, Pro or His); Xaa at res.62=(Val, Ala or Ile); Xaa at res.63=(Pro or Asp); Xaa at res.64=(Lys, Leu or Glu); Xaa at res.65=(Pro or Ala); Xaa at res.68=(Ala or Val); Xaa at res.70=(Thr, Ala or Glu); Xaa at res.71=(Gln, Lys, Arg or Glu); Xaa at res.72=(Leu, Met or Val); Xaa at res.73=(Ash, Set, Asp or Gly); Xaa at res.74=(Ala, Pro or Ser); Xaa at res.75=(Ile, Thr, Val or Leu); Xaa at res.76=(Ser, Ala or Pro); Xaa at res.77=(Val, Met or Ile); Xaa at res.79=(Tyr or Phe); Xaa at res.80=(Phe, Tyr, Leu or His); Xaa at res.81=(Asp, Asn or Leu); Xaa at res.82=(Asp, Glu, Asn or Ser); Xaa at res.83=(Ser, Gln, Asn, Tyr or Asp); Xaa at res.84=(Ser, Ash, Asp, Glu or Lys); Xaa at res.85=(Asn, Thr or Lys); Xaa at res.87=(Ile, Val or Asn); Xaa at res.89=(Lys or Arg); Xaa at res.90=(Lys, Asn, Gln, His or Val); Xaa at res.91=(Tyr or His); Xaa at res.92=(Arg, Gln, Glu or Pro); Xaa at res.93=(Asn, Glu or Asp); Xaa at res.95=(Val, Thr, Ala or Ile); Xaa at res.97=(Arg, Lys, Val, Asp or Glu); Xaa at res.98=(Ala, Gly, Glu or Ser); Xaa at res.100=(Gly or Ala); and Xaa at res.102=(His or Arg).

Particularly useful sequences for use as morphogens in this invention include the C-terminal domains, e.g., the C-terminal 96-102 amino acid residues of Vgl, Vgr-1, DPP, OP-1, OP-2, CBMP-2A, CBMP-2B, GDF-1 (see Table II, below, and Seq. ID Nos. 5-14), as well as proteins comprising the C-terminal domains of 60A, BMP3, BMP5 and BMP6 (see Seq. ID Nos. 24-28), all of which include at least the conserved six or seven cysteine skeleton. In addition, biosynthetic constructs designed from the generic sequences, such as COP-1, 3-5, 7, 16, disclosed in U.S. Pat. No. 5,011,691, also are useful. Other sequences include the inhibins/activin proteins (see, for example, U.S. Pat. Nos. 4,968,590 and 5,011,691). Accordingly, other useful sequences are those sharing at least 70% amino acid sequence homology or "similarity", and preferably 80% homology or similarity with any of the sequences above. These are anticipated to include allelic and species variants and mutants, and biosynthetic muteins, as well as novel members of this morphogenic family of proteins. Particularly envisioned in the family of related proteins are those proteins exhibiting morphogenic activity and wherein the amino acid changes from the preferred sequences include conservative changes, e.g., those as defined by Dayoff et al., *Atlas of Protein Sequence and Structure*; vol. 5, Suppl. 3, pp. 345-362, (M. O. Dayoff, ed., *Nat'l BioMed. Research Fdn.*, Washington, D.C. 1979). As used herein, potentially useful sequences are aligned with a known morphogen sequence using the method of Needleman et al. ((1970) *J. Mol. Biol.* 48:443–453) and identities calculated by the Align program (DNAstar, Inc.). "Homology" or "similarity" as used herein includes allowed conservative changes as defined by Dayoff et al.

Morphogen sequences which are detectable according to the methods of the invention include but are not limited to those having greater than 60% identity, preferably greater than 65% identity, with the amino acid sequence defining the conserved six cysteine skeleton of hOP1 (e.g., residues 43-139 of Seq. ID No. 5). These most preferred sequences include both allelic and species variants of the OP-1 and OP-2 proteins, including the Drosophila 60A protein. Accordingly, morphogens which are detectable according to the invention include active proteins comprising species of polypeptide chains having the generic amino acid sequence herein referred to as "OPX", which accommodates the homologies between the various identified species of OP1 and OP2 (Seq. ID No. 29).

The morphogens detectable in the methods of this invention include proteins comprising any of the polypeptide chains described above, whether isolated from naturally-occurring sources, or produced by recombinant DNA or other synthetic techniques, and includes allelic and species variants of these proteins, naturally-occurring or biosynthetic mutants thereof, chimetic variants containing a domain(s) or region(s) of one family member functionally arranged with another domain(s) or regions(s) of a second family member, as well as various truncated and fusion constructs. Deletion or insertion or addition mutants also are envisioned to be active, including those which may alter the conserved C-terminal cysteine skeleton, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The morphogenic proteins can be expressed from intact or truncated cDNA or from synthetic DNAs in procaryotic or eucaryotic host cells, and purified, cleaved, refolded, and dimerized to form morphogenically active compositions. Currently preferred host cells include E. coli or mammalian cells, such as CHO, COS or BSC cells. A detailed description of the morphogens detectable according to the methods of this invention is disclosed in copending U.S. patent application Ser. Nos. 752,764, filed Aug. 30, 1991, and 667,274, filed Mar. 11, 1991, the disclosure of which are incorporated herein by reference.

The screening method of the invention provides a simple method of determining a change in the level of morphogenic protein as a result of exposure of cultured cells to one or more compound(s). The level of a morphogenic protein in a given cell culture, or a change in that level resulting from exposure to one or more compound(s) indicates that direct application of the compound modulates the level of the morphogen expressed by the cultured cells. If, for example, a compound upregulated the production of OP-1 by a kidney cell line, it would then be desirable to test systemic administration of this compound in an animal model to determine if it upregulated the production of OP-1 in vivo. If this compound did upregulate the endogenous circulating levels of OP-1, it would be consistent with administration of the compound systemically for the purpose of correcting bone metabolism diseases such as osteoporosis. The level of morphogen in the body may be a result of a wide range of physical conditions, e.g., tissue degeneration such as occurs in diseases including arthritis, emphysema, osteoporosis, kidney diseases, lung diseases, cardiomyopathy, and cirrhosis of the liver. The level of morphogens in the body may also occur as a result of the normal process of aging. A compound selected by the screening method of the invention as, for example, one which increases the level of morphogen in a tissue, may be consistent with the administration of the compound systemically or locally to a tissue for the purpose of preventing some form of tissue degeneration or for restoring the degenerated tissue to its normal healthy level.

Other advantages of the invention include determining the tissue or tissues of origin of a given morphogen in order to administer a compound aimed at modulating the systemic level of morphogen for treatment of a disease or condition in which the level of morphogen production has become altered.

DETAILED DESCRIPTION

Figure 1:
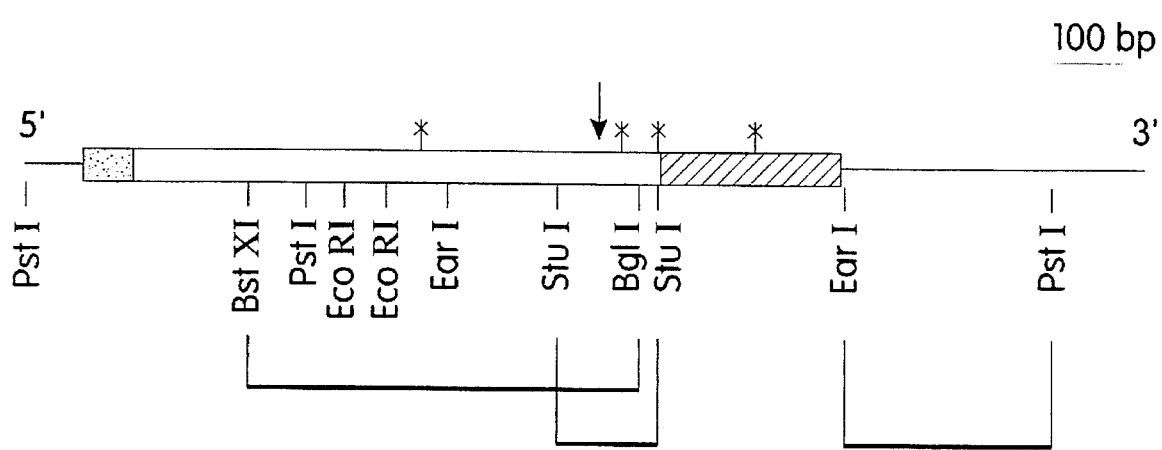
FIG. 1 shows the fragments of OP-1, used as probes in Northern hybridizations useful in the processes of the invention.

The invention is based on the discovery of a family of structurally related morphogenic proteins (BMPs), also called osteogenic proteins (OPs), and more particularly that various of these proteins play an important role, not only in embryogenesis, but also in tissue and organ maintenance and repair in juvenile and adult mammals. Morphogenic proteins which have been identified include BMP 2, 3, 4, 5, 6, OP-1 and OP-2 (murine and human), Vgr-1, Vgl, DPP, GDF-1, CMBP-2A, CMBP-2B, 60A, and the inhibin/activin class of proteins. Other recombinant proteins include COP1, COP3, COP4, COP5, COP7, and COP16. While, as explained herein, the morphogen have significant homologies and similarities in structure, it is hypothesized that variants within the morphogenic protein genes may have specific roles in specific tissue involving, for example, stimulation of progenitor cell multiplication, tissue specific or tissue preferred phenotype maintenance, and/or stimulation or modulation of the rate of differentiation, growth or replication of tissue cells characterized by high turnover. The effect on the long-term physiology, maintenance and repair of particular tissues by particular species of the morphogens is currently unknown in any significant detail. However, methods useful in determining which particular tissues express which particular morphogen(s), and for finding changes which stimulate or depress morphogen expression in vivo, would enable discovery and development of strategies for therapeutic treatment of a large number of diseased states, and provide drugs designed to implement the strategy.

This invention provides such methods and, more specifically, two generic processes for obtaining data which ultimately will permit determination of structure/activity relationships of specific naturally occurring mammalian morphogens and drugs capable of modulating their production. For example, using the assay of the invention, it has been determined that OP-1, first found in bone and demonstrated to be osteoinductive, is synthesized primarily in kidney, bladder, and adrenal tissue. This surprising discovery, coupled with the observation that patients with kidney disease often express loss of bone mass, suggests that the bone loss in these patients may be due to pathologic depression of OP-1 synthesis in kidney, and suggests that administration of OP-1 systemically or stimulation of OP-1 expression and secretion by the kidney may arrest bone loss, or effect remineralization through increased bone formation (i.e., osteogenesis).

There are two fundamental aspects of the invention. One aspect involves an assay to determine tissues and cell types capable of synthesis and secretion of the morphogens; the other involves the use of the identified cell types configured in a screening system to find substances useful therapeutically to modulate, i.e., stimulate or depress, morphogen expression and/or secretion.

The assay to determine the tissue of origin of a given morphogen involves screening a plurality (i.e., two or more) different tissues by determining a parameter indicative of production of a morphogen in the tissue, and comparing the parameters. The tissue(s) of origin will, of course, be the tissue that produces that morphogen.

The other assay of the invention involves screening candidate compounds for their ability to modulate the effective systemic or local concentration of a morphogen by incubating the compound with a cell culture that produces the morphogen, and assaying the culture for a parameter indicative of a change in the production level of the morphogen. Useful candidate compounds then may be tested for in vivo efficacy in a suitable animal model. These compounds then may be used in vivo to modulate effective morphogen concentrating in the disease treatment.

1. Morphogen Tissue Distribution

Morphogens are broadly distributed in developing and adult tissue. For example, DPP and 60A are expressed in both embryonic and developing Drosophila tissue. Vgl has been identified in Xenopus embryonic tissue. Vgr-1 transcripts have been identified in a variety of murine tissues, including embryonic and developing brain, lung, liver, kidney and calvaria (dermal bone) tissue. In addition, both CBMP2B and CBMP3 have been identified in lung tissue. Recently, Vgr-1 transcripts also have been identified in adult murine lung, kidney, heart, and brain tissue, with particularly high levels in the lung (see infra). GDF-1 has been identified in human adult cerebellum and in fetal brain tissue. In addition, recent Northern blot analyses indicate that OP-1 is encoded by multiple transcripts in different tissues. This potential alternative splicing is consistent with the hypothesis that the longer transcripts may encoded additional proteins (e.g., bicistronic mRNA) and each form may be tissue or developmentally related.

OP-1 and the CBMP2 proteins, both first identified as bone morphogens, have been identified in mouse and human placenta, hippocampus, calvaria and osteosarcoma tissue as determined by identification of OP-1 and CMBP2-specific sequences in cDNA libraries constructed from these tissues (see U.S. Ser. No. 422,699, incorporated herein by reference). Additionally, the OP-1 protein is present in a variety of embryonic and developing tissues including kidney, liver, heart and brain as determined by Western blot analysis and immunolocalization (see infra). OP-1-specific transcripts also have been identified in both embryonic and developing tissues, most abundantly in developing kidney, bladder, adrenal and (see infra). OP-1 also has been identified as a mesoderm inducing factor present during embryogenesis. Moreover, OP-1 has been shown to be associated with satellite cells in the muscle and associated with potential pluripotential stem cells in bone marrow following damage to adult murine endochondral bone, indicating its morphogenic role in tissue repair and regeneration. In addition, a novel protein GDF-1 comprising a 7 cysteine skeleton, has been identified in neural tissue (Lee, 1991, Proc. Nat. Aca. Sci. 88: 4250-4254).

Knowledge of the tissue distribution of a given morphogen may be useful in choosing a cell type for screening according to the invention, or for targeting that cell type or tissue type for treatment. The proteins (or their mRNA transcripts) are readily identified in different tissues using standard methodologies and minor modifications thereof in tissues where expression may be low. For example, protein distribution may be determined using standard Western blot analysis or immunocytochemical techniques, and antibodies specific to the morphogen or morphogens of interest. Similarly, the distribution of morphogen transcripts may be determined using standard Northern hybridization protocols and a transcript-specific probe and hybridization conditions.

2. Useful Morphogens

As defined herein a protein is morphogenic if it is capable of inducing the developmental cascade of cellular and molecular events that culminate in the formation of new, organ-specific tissue and comprises at least the conserved C-terminal six cysteine skeleton or its functional equivalent (see supra). Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. Details of how the morphogens detectable according to the methods of this invention first were identified, as well as a description on how to make, use and test them for morphogenic activity are disclosed in U.S. Ser. No. 667,274, filed Mar. 11, 1991 and U.S. Ser. No. 752,764, filed Aug. 30, 1991, the disclosures of which are hereby incorporated by reference.

A candidate morphogen or morphogen composition can be evaluated for in vivo morphogenic utility generally according to the procedures set forth in U.S. Ser. No. 07/752,764. The proteins and compositions may be injected or surgically implanted in a mammal, following any of a number of procedures well known in the art. For example, surgical implant bioassays may be performed essentially following the procedure of Sampath et al. (1983) PNAS 8-0:6591–6595.

Histological sectioning and staining is preferred to determine the extent of morphogenesis in vivo, particularly in tissue repair procedures. Excised implants are fixed in Bouins Solution, embedded in paraffin, and cut into 6–8 μm sections. Staining with toluidine blue or hemotoxylin/eosin demonstrates clearly the ultimate development of the new tissue. Twelve day implants are usually sufficient to determine whether the implants contain newly induced tissue.

Successful implants exhibit a controlled progression through the stages of induced tissue development allowing one to identify and follow the tissue-specific events that occur. For example, in endochondral bone formation the stages include:

(1) leukocytes on day one;

(2) mesenchymal cell migration and proliferation on days two and three;

(3) chondrocyte appearance on days five and six;

(4) cartilage matrix formation on day seven;

(5) cartilage calcification on day eight;

(6) vascular invasion, appearance of osteoblasts, and formation of new bone on days nine and ten;

(7) appearance of osteoblastic and bone remodeling and dissolution of the implanted matrix on days twelve to eighteen; and (8) hematopoietic bone marrow differentiation in the ossicle on day twenty-one.

In addition to histological evaluation, biological markers may be used as a marker for tissue morphogenesis. Useful markers include tissue-specific enzymes whose activity may be assayed (e.g., spectrophotometrically) after homogenization of the implant. These assays may be useful for quantitation and for obtaining an estimate of tissue formation quickly after the implants are removed from the animal. For example, alkaline phosphatase activity may be used as a marker for osteogenesis.

Incorporation of systemically provided morphogens may be followed using tagged morphogens (e.g., radioactively labelled) and determining their localization in new tissue, and/or by monitoring their disappearance from the circulatory system using a standard pulse-chase labeling protocol.

The morphogen also may be provided with a tissue-specific molecular tag, whose uptake may be monitored and correlated with the concentration of morphogen provided. As an example, ovary removal in female rats results in reduced bone alkaline phosphatase activity, rendering the rats predisposed to osteoporosis. If the female rats now are provided with a morphogen, e.g., OP-1, a reduction in the systemic concentration of calcium ($CA^{2+}$) is seen, which correlates with the presence of the provided morphogen and can be shown to correspond to increased alkaline phosphatase activity.

Particularly useful proteins include those which comprise the naturally derived sequences disclosed in Table II. Other useful sequences include biosynthetic constructs such as those disclosed in U.S. Pat. No. 5,011,691, the disclosure of which is incorporated herein by reference (e.g., COP-1, COP-3, COP-4, COP-5, COP-7, and COP-16).

Accordingly, the morphogens detectable according to the methods and compositions of this invention also may be described by morphogenically active proteins having amino acid sequences sharing 70% or, preferably, 80% homology (similarity) with any of the sequences described above, where "homology" is as defined herein above.

The morphogens detectable according to the method of this invention also can be described by any of the 6 generic sequences described herein (Generic Sequences 1, 2, 3, 4, 5 and 6). Generic sequences 1 and 2 also may include, at their N-terminus, the sequence Cys Xaa Xaa Xaa Xaa  (Seq. ID No. 15)
 1            5

Table II, set forth below, compares the amino acid sequences of the active regions of native proteins that have been identified as morphogens, including human OP-1 (hOP-1, Seq. ID Nos. 5 and 16-17), mouse OP-1 (mOP-1, Seq. ID Nos. 6 and 18-19), human and mouse OP-2 (Seq. ID Nos. 7, 8, and 20-23), CBMP2A (Seq. ID No. 9), CBMP2B (Seq. ID No. 10), BMP3 (Seq. ID No. 26), DPP (from Drosophila, Seq. ID No. 11), Vgl, (from Xenopus, Seq. ID No. 12), Vgr-1 (from mouse, Seq. ID No. 13), GDF-1 (from mouse, Seq. ID Nos. 14, 32 and 33), 60A protein (from Drosophila, Seq. ID Nos. 24 and 25), BMP5 (Seq. ID No. 27) and BMP6 (Seq. ID No. 28). The sequences are aligned essentially following the method of Needleman et al. (1970) J. Mol. Biol., 48:443-453, calculated using the Align Program (DNAstar, Inc.) In the table, three dots indicates that the amino acid in that position is the same as the amino acid in hOP-1. Three dashes indicates that no amino acid is present in that position, and are included for purposes of illustrating homologies. For example, amino acid residue 60 of CBMP-2A and CBMP-2B is "missing". Of course, both these amino acid sequences in this region comprise Asn-Ser (residues 58, 59), with CBMP-2A then comprising Lys and Ile, whereas CBMP-2B comprises Ser and Ile.

TABLE II

| | | | | | | | | |
|---|---|---|---|---|---|---|---|---|
| hOP-1 | Cys | Lys | Lys | His | Glu | Leu | Tyr | Val |
| mOP-1 | — | — | — | — | — | — | — | — |
| hOP-2 | — | Arg | Arg | — | — | — | — | — |
| mOP-2 | — | Arg | Arg | — | — | — | — | — |
| DPP | — | Arg | Arg | — | Ser | — | — | — |
| Vgl | — | — | Lys | Arg | His | — | — | — |
| Vgr-1 | — | — | — | — | Gly | — | — | — |
| CBMP-2A | — | — | Arg | — | Pro | — | — | — |
| CBMP-2B | — | Arg | Arg | — | Ser | — | — | — |

TABLE II-continued

| | | | | | | | | |
|---|---|---|---|---|---|---|---|---|
| BMP3 | — | Ala | Arg | Arg | Tyr | — | Lys | — |
| GDF-1 | — | Arg | Ala | Arg | Arg | — | — | — |
| 60A | — | Gln | Met | Glu | Thr | — | — | — |
| BMP5 | — | — | — | — | — | — | — | — |
| BMP6 | — | Arg | — | — | — | — | — | — |
| | 1 | | | | 5 | | | |

| | | | | | | | | |
|---|---|---|---|---|---|---|---|---|
| hOP-1 | Ser | Phe | Arg | Asp | Leu | Gly | Trp | Gln | Asp |
| mOP-1 | — | — | — | — | — | — | — | — | — |
| hOP-2 | — | — | Gln | — | — | — | — | Leu | — |
| mOP-2 | Ser | — | — | — | — | — | — | Leu | — |
| DPP | Asp | — | Ser | — | Val | — | — | Asp | — |
| Vgl | Glu | — | Lys | — | Val | — | — | — | Asn |
| Vgr-1 | — | — | Gln | — | Val | — | — | — | — |
| CBMP-2A | Asp | — | Ser | — | Val | — | — | Asn | — |
| CBMP-2B | Asp | — | Ser | — | Val | — | — | Asn | — |
| BMP3 | Asp | — | Ala | — | Ile | — | — | Ser | Glu |
| GDF-1 | — | — | — | Glu | Val | — | — | His | Arg |
| 60A | Asp | — | Lys | — | — | — | — | His | — |
| BMP5 | — | — | — | — | — | — | — | — | — |
| BMP6 | — | — | Gln | — | — | — | — | — | — |
| | | 10 | | | | 15 | | | |

| | | | | | | | | |
|---|---|---|---|---|---|---|---|---|
| hOP-1 | Trp | Ile | Ile | Ala | Pro | Glu | Gly | Tyr | Ala |
| mOP-1 | — | — | — | — | — | — | — | — | — |
| hOP-2 | — | Val | — | — | — | Gln | — | — | Ser |
| mOP-2 | — | Val | — | — | — | Gln | — | — | Ser |
| DPP | — | — | Val | — | — | Leu | — | — | Asp |
| Vgl | — | Val | — | — | — | Gln | — | — | Met |
| Vgr-1 | — | — | — | — | — | Lys | — | — | — |
| CBMP-2A | — | — | Val | — | — | Pro | — | — | His |
| CBMP-2B | — | — | Val | — | — | Pro | — | — | Gln |
| BMP3 | — | — | — | Ser | — | Lys | Ser | Phe | Asp |
| GDF-1 | — | Val | — | — | — | Arg | — | Phe | Leu |
| 60A | — | — | — | — | — | — | — | — | Gly |
| BMP5 | — | — | — | — | — | — | — | — | — |
| BMP6 | — | — | — | — | — | Lys | — | — | — |
| | | | 20 | | | | | 25 | |

| | | | | | | | | |
|---|---|---|---|---|---|---|---|---|
| hOP-1 | Ala | Tyr | Tyr | Cys | Glu | Gly | Glu | Cys | Ala |
| mOP-1 | — | — | — | — | — | — | — | — | — |
| hOP-2 | — | — | — | — | — | — | — | — | Ser |
| mOP-2 | — | — | — | — | — | — | — | — | — |
| DPP | — | — | — | — | His | — | Lys | — | Pro |
| Vgl | — | Asn | — | — | Tyr | — | — | — | Pro |
| Vgr-1 | — | Asn | — | — | Asp | — | — | — | Ser |
| CBMP-2A | — | Phe | — | — | His | — | Glu | — | Pro |
| CBMP-2B | — | Phe | — | — | His | — | Asp | — | Pro |
| BMP3 | — | — | — | — | Ser | — | Ala | — | Gln |
| GDF-1 | — | Asn | — | — | Gln | — | Gln | — | — |
| 60A | — | Phe | — | — | Ser | — | — | — | Asn |
| BMP5 | — | Phe | — | — | Asp | — | — | — | Ser |
| BMP6 | — | Asn | — | — | Asp | — | — | — | Ser |
| | | | | | 30 | | | | 35 |

| | | | | | | | | |
|---|---|---|---|---|---|---|---|---|
| hOP-1 | Phe | Pro | Leu | Asn | Ser | Tyr | Met | Asn | Ala |
| mOP-1 | — | — | — | — | — | — | — | — | — |
| hOP-2 | — | — | — | Asp | — | Cys | — | — | — |
| mOP-2 | — | — | — | Asp | — | Cys | — | — | — |
| DPP | — | — | — | Ala | Asp | His | Phe | — | Ser |
| Vgl | Tyr | — | — | Thr | Glu | Ile | Leu | — | Gly |
| Vgr-1 | — | — | — | — | Ala | His | — | — | — |
| CBMP-2A | — | — | — | Ala | Asp | His | Leu | — | Ser |
| CBMP-2B | — | — | — | Ala | Asp | His | Leu | — | Ser |
| GDF-1 | Leu | — | Val | Ala | Leu | Ser | Gly | Ser** | — |
| BMP3 | — | — | Met | Pro | Lys | Ser | Leu | Lys | Pro |
| 60A | — | — | — | — | Ala | His | — | — | — |
| BMP5 | — | — | — | — | Ala | His | Met | — | — |
| BMP6 | — | — | — | — | Ala | His | Met | — | — |
| | | | | | 40 | | | | |

| | | | | | | | | |
|---|---|---|---|---|---|---|---|---|
| hOP-1 | Thr | Asn | His | Ala | Ile | Val | Gln | Thr | Leu |
| mOP-1 | — | — | — | — | — | — | — | — | — |
| hOP-2 | — | — | — | — | — | Leu | — | Ser | — |
| mOP-2 | — | — | — | — | — | Leu | — | Ser | — |
| DPP | — | — | — | — | Val | — | — | — | — |
| Vgl | Ser | — | — | — | — | Leu | — | — | — |
| Vgr-1 | — | — | — | — | — | — | — | — | — |
| CBMP-2A | — | — | — | — | — | — | — | — | — |

TABLE II-continued

| | | | | | | | | | |
|---|---|---|---|---|---|---|---|---|---|
| CBMP-2B | — | — | — | — | — | — | — | — | — |
| BMP3 | Ser | — | — | — | Thr | Ile | — | Ser | Ile |
| GDF-1 | Leu | — | — | — | Val | Leu | Arg | Ala | — |
| 60A | — | — | — | — | — | — | — | — | — |
| BMP5 | — | — | — | — | — | — | — | — | — |
| BMP6 | — | — | — | — | — | — | — | — | — |
| | 45 | | | | | 50 | | | |

| | | | | | | | | | |
|---|---|---|---|---|---|---|---|---|---|
| hOP-1 | Val | His | Phe | Ile | Asn | Pro | Glu | Thr | Val |
| mOP-1 | — | — | — | — | — | — | Asp | — | — |
| hOP-2 | — | His | Leu | Met | Lys | — | Asn | Ala | — |
| mOP-2 | — | His | Leu | Met | Lys | — | Asp | Val | — |
| DPP | — | Asn | Asn | Asn | — | — | Gly | Lys | — |
| Vgl | — | — | Ser | — | Glu | — | Asp | Asp | Ile |
| Vgr-1 | — | — | Val | Met | — | — | — | Tyr | — |
| CBMP-2A | — | Asn | Ser | Val | — | Ser | — | Lys | Ile |
| CBMP-2B | — | Asn | Ser | Val | — | Ser | — | Ser | Ile |
| BMP3 | — | Arg | Ala** | Gly | Val | Val | Pro | Gly | Ile |
| GDF-1 | Met | — | Ala | Ala | Ala | — | Gly | Ala | Ala |
| 60A | — | — | Leu | Leu | Glu | — | Lys | Lys | — |
| BMP5 | — | — | Leu | Met | Phe | — | Asp | His | — |
| BMP6 | — | — | Leu | Met | — | — | — | Tyr | — |
| | | | 55 | | | | 60 | | |

| | | | | | | | | | |
|---|---|---|---|---|---|---|---|---|---|
| hOP-1 | Pro | Lys | Pro | Cys | Cys | Ala | Pro | Thr | Gln |
| mOP-1 | — | — | — | — | — | — | — | — | — |
| hOP-2 | — | — | Ala | — | — | — | — | — | Lys |
| mOP-2 | — | — | Ala | — | — | — | — | — | Lys |
| DPP | — | — | Ala | — | — | Val | — | — | — |
| Vgl | — | Leu | — | — | — | Val | — | — | Lys |
| Vgr-1 | — | — | — | — | — | — | — | — | Lys |
| CBMP-2A | — | — | Ala | — | — | Val | — | — | Glu |
| CBMP-2B | — | — | Ala | — | — | Val | — | — | Glu |
| BMP3 | — | Glu | — | — | — | Val | — | Glu | Lys |
| GDF-1 | Asp | Leu | — | — | — | Val | — | Ala | Arg |
| 60A | — | — | — | — | — | — | — | — | Arg |
| BMP5 | — | — | — | — | — | — | — | — | Lys |
| BMP6 | — | — | — | — | — | — | — | — | Lys |
| | | | 65 | | | | 70 | | |

| | | | | | | | | | |
|---|---|---|---|---|---|---|---|---|---|
| hOP-1 | Leu | Asn | Ala | Ile | Ser | Val | Leu | Tyr | Phe |
| mOP-1 | — | — | — | — | — | — | — | — | — |
| hOP-2 | — | Ser | — | Thr | — | — | — | — | Tyr |
| mOP-2 | — | Ser | — | Thr | — | — | — | — | Tyr |
| Vgl | Met | Ser | Pro | — | — | Met | — | Phe | Tyr |
| Vgr-1 | Val | — | — | — | — | — | — | — | — |
| DPP | — | Asp | Ser | Val | Ala | Met | — | — | Leu |
| CBMP-2A | — | Ser | — | — | — | Met | — | — | Leu |
| CBMP-2B | — | Ser | — | — | — | Met | — | — | Leu |
| BMP3 | Met | Ser | Ser | Leu | — | Ile | — | Phe | Tyr |
| GDF-1 | — | Ser | Pro | — | — | — | — | Phe | — |
| 60A | — | Gly | — | Leu | Pro | — | — | — | His |
| BMP5 | — | — | — | — | — | — | — | — | — |
| BMP6 | — | — | — | — | — | — | — | — | — |
| | | | 75 | | | | | | 80 |

| | | | | | | | | | |
|---|---|---|---|---|---|---|---|---|---|
| hOP-1 | Asp | Asp | Ser | Ser | Asn | Val | Ile | Leu | Lys |
| mOP-1 | — | — | — | — | — | — | — | — | — |
| hOP-2 | — | Ser | — | Asn | — | — | — | — | Arg |
| mOP-2 | — | Ser | — | Asn | — | — | — | — | Arg |
| DPP | Asn | — | Gln | — | Thr | — | Val | — | — |
| Vgl | — | Asn | Asn | Asp | — | — | Val | — | Arg |
| Vgr-1 | — | — | Asn | — | — | — | — | — | — |
| CBMP-2A | — | Glu | Asn | Glu | Lys | — | Val | — | — |
| CBMP-2B | — | Glu | Tyr | Asp | Lys | — | Val | — | — |
| BMP3 | — | Glu | Asn | Lys | — | — | Val | — | — |
| GDF-1 | — | Asn | — | Asp | — | — | Val | — | Arg |
| 60A | Leu | Asn | Asp | Glu | — | — | Asn | — | — |
| BMP5 | — | — | — | — | — | — | — | — | — |
| BMP6 | — | — | Asn | — | — | — | — | — | — |
| | | | | | 85 | | | | |

| | | | | | | | | |
|---|---|---|---|---|---|---|---|---|
| hOP-1 | Lys | Tyr | Arg | Asn | Met | Val | Val | Arg |
| mOP-1 | — | — | — | — | — | — | — | — |
| hOP-2 | — | His | — | — | — | — | — | Lys |
| mOP-2 | — | His | — | — | — | — | — | Lys |
| DPP | Asn | — | Gln | Glu | — | Thr | — | Val |
| Vgl | His | — | — | Glu | — | — | Ala | — | Asp |
| Vgr-1 | — | — | — | — | — | — | — | — |

TABLE II-continued

| | | | | | | | | |
|---|---|---|---|---|---|---|---|---|
| CBMP-2A | Asn | — | Gln | Asp | — | — | — | Glu |
| CBMP-2B | Asn | — | Gln | Glu | — | — | — | Glu |
| BMP3 | Val | — | Pro | — | — | Thr | — | Glu |
| GDF-1 | Gln | — | Glu | Asp | — | — | — | Asp |
| 60A | — | — | — | — | — | Ile | — | Lys |
| BMP5 | — | — | — | — | — | — | — | — |
| BMP6 | — | — | — | Trp | — | — | — | — |
| | 90 | | | | | 95 | | |

| | | | | | |
|---|---|---|---|---|---|
| hOP-1 | Ala | Cys | Gly | Cys | His |
| mOP-1 | — | — | — | — | — |
| hOP-2 | — | — | — | — | — |
| mOP-2 | — | — | — | — | — |
| DPP | Gly | — | — | — | Arg |
| Vgl | Glu | — | — | — | Arg |
| Vgr-1 | — | — | — | — | — |
| CBMP-2A | Gly | — | — | — | Arg |
| CBMP-2B | Gly | — | — | — | Arg |
| BMP3 | Ser | — | Ala | — | Arg |
| GDF-1 | Glu | — | — | — | Arg |
| 60A | Ser | — | — | — | — |
| BMP5 | Ser | — | — | — | — |
| BMP6 | — | — | — | — | — |
| | | | 100 | | |

**Between residues 56 and 57 of BMP3 is a Val residue; between residues 43 and 44 of GDF-1 lies the amino acid sequence Gly—Gly—Pro—Pro.

As is apparent from the foregoing amino acid sequence comparisons, significant amino acid changes can be made within the generic sequences while retaining the morphogenic activity. For example, while the GDF-1 protein sequence depicted in Table II shares only about 50% amino acid identity with the hOP1 sequence described therein, the GDF-1 sequence shares greater than 70% amino acid sequence homology (or "similarity") with the hOP1 sequence, where "homology" or "similarity" includes allowed conservative amino acid changes within the sequence as defined by Dayoff, et al., *Atlas of Protein Sequence and Structure* vol.5, supp.3, pp.345-362, (M. O. Dayoff, ed., Nat'l BioMed. Res. Fd'n, Washington D.C. 1979.)

The currently most preferred protein sequences detectable as morphogens in this invention include those having greater than 60% identity, preferably greater than 65% identity, with the amino acid sequence defining the conserved six cysteine skeleton of hOP1 (e.g., residues 43-139 of Seq. ID No. 5). These most preferred sequences include both allelic and species variants of the OP-1 and OP-2 proteins, including the Drosophila 60A protein. Accordingly, in still another preferred aspect, the invention includes detection of morphogens comprising species of polypeptide chains having the generic amino acid sequence referred to herein as "OPX", which defines the seven cysteine skeleton and accommodates the identities between the various identified mouse and human OP1 and OP2 proteins. OPX is presented in Seq. ID No. 29. As described therein, each Xaa at a given position independently is selected from the residues occurring at the corresponding position in the C-terminal sequence of mouse or human OP1 or OP2 (see Seq. ID Nos. 5-8 and/or Seq. ID Nos. 16-23).

3. Tissue-Specific Expression of OP-1

Once a morphogen is identified in a tissue, its level may be determined either at the protein or nucleic acid level. By comparing the levels of production of a given morphogen among different tissues, it is possible to determine the tissue(s) of origin of that morphogen. The level of production of the morphogen OP-1 in different tissues is one example of a morphogen having a tissue of origin, i.e., the kidney, which contains a cell type that can also be used as the cell type which is used to screen, according to the invention, different compounds for their potential effects on morphogen (OP-1) production.

The level of OP-1 varies among different tissue types. In order to screen compounds for their effect on the production of OP-1 by a given cell type, it may be desirable to determine which tissues produce levels of OP-1 which are sufficiently high to show a potential decrease and sufficiently low to show a potential increase in production. Different tissues may be screened at the RNA level as follows.

Any probe capable of hybridizing specifically to a transcript, and distinguishing the transcript of interest from other, related transcripts may be used. Because the morphogens to be detected in the methods of this invention share such high sequence homology in their C-terminal domain, the tissue distribution of a specific morphogen transcript may best be determined using a probe specific for the "pro" region of the immature protein and/or the N-terminal heterogeneous region of the mature protein. Another useful probe sequence is the 3'non-coding region immediately following the stop codon. These portions of the sequence vary substantially among the morphogens of this invention, and accordingly, are specific for each protein. For example, a particularly useful Vgr-1-specific probe sequence is the PvuII-SacI fragment, a 265 bp fragment encoding both a portion of the pro region and the N-terminus of the mature sequence. Similarly, particularly useful mOP-1-specific probe sequences are the BstXI-BglI fragment, a 0.68kb sequence that covers approximately two-thirds of the mOP1 pro region; a StuI-StuI fragment, a 0.2 kb sequence immediately upstream of the 7-cysteine domain, and an EarI-PstI fragment, a 0.3 kb fragment containing the 3'untranslated sequence. Similar approaches may be used, for example, with hOP-1 (SEQ. ID NO.16) or human or mouse OP-2 (SEQ. ID NOS.20 and 22).

Using morphogen-specific oligonucleotides probes, morphogen transcripts can be identified in mammalian tissues, using standard methodologies well known to those having ordinary skill in the art. Briefly, total RNA from mouse embryos and organs from post-natal animals is prepared using the acid guanidine thiocyanate-phenol-chloroform method (Chomczynski et al., Anal. Biochem. 162:156-159, 1987). The RNA may be dissolved in TES buffer (10 mM Tris-HCl mM EDTA, 0.1% SDS, pH 7.5) and treated with Proteinase K (approx. 1.5 mg per g tissue sample) at 45° C. for 1 hr. Poly(A)$^+$ RNA selection on oligo(dT)-cellulose (Type 7, Pharmacia LKB Biotechnology Inc., Piscataway, N.J.) may be done in a batch procedure by mixing 0.1 g oligo(dT)-cellulose with 11 ml RNA solution (from 1 g tissue) in TES buffer and 0.5 M NaCl). Thereafter the oligo(dT) cellulose is washed in binding buffer (0.5 M NaCl, 10 mM Tris-HCl, mM EDTA, pH 7.5) and poly(A)$^+$RNA is eluted with water. Poly(A)$^+$ RNA (5 or 15 μg/lane) is fractionated on 1 or 1.2% agarose-formaldehyde gels (Selden, in Current Protocols in Molecular Biology, Ausubel et al. eds., pp. 1-4, 8, 9, Greene Publishing and Wiley-Interscience, N.Y., 1991). 1 μl of 400 μg/ml ethidium bromide is added to each sample prior to heat denaturation (Rosen et al., Focus 12:23-24, 1990). Following electrophoresis, the gels are photographed and the RNA is blotted overnight onto Nytran nitrocellulose membranes (Schleicher & Schuell Inc., Keene, N.H.) with 10 x SSC. The membranes are baked at 80° C. for 30–60 min. and irradiated with UV light (1 mW/cm$^2$ for 25 sec.). The Northern hybridization conditions may be as previously described (Ozkaynak et al., EMBO J. 9:2085–2093, 1990). For re-use, the filters may be deprobed in 1 mM Tris-HCl, 1 mM EDTA, 0.1% SDS, pH 7.5, at 90°–95° C. and exposed to film to assure complete removal of previous hybridization signals.

One probe which may be used to screen for transcripts encoding a morphogen includes a portion of or the complete OP-1 cDNA, which may be used to detect the presence of OP-1 mRNA or mRNAs of related morphogens. The sequence of the murine cDNA gene is set forth in SEQ ID NO:14.

OP-1 mRNA expression was analyzed in 17 day mouse embryos and 3 day post-natal mice by sequentially hybridizing filters with various probes. Probes from regions other than the highly conserved 7-cysteine domain were selected because this region is highly variable among members of the TGF-β superfamily. FIG. 1 shows the fragments of OP-1, used as probes in the Northern hybridizations. The solid box indicates the putative signal peptide and the hatched box corresponds to the TGF-β-like domain that contains the seven cysteine residues. Asterisks indicate the potential N-glycosylation sites. The arrow marks the location of the cleavage site for OP-1 maturation. Three solid bars below the diagram indicate the OP-1 specific fragments used in making $^{32}$P-labeled probes (0.68 kb BstXI - BglI fragment, 0.20 kb StuI - StuI fragment and 0.34 kb EarI- PstI non-coding fragment).

Figure 2:
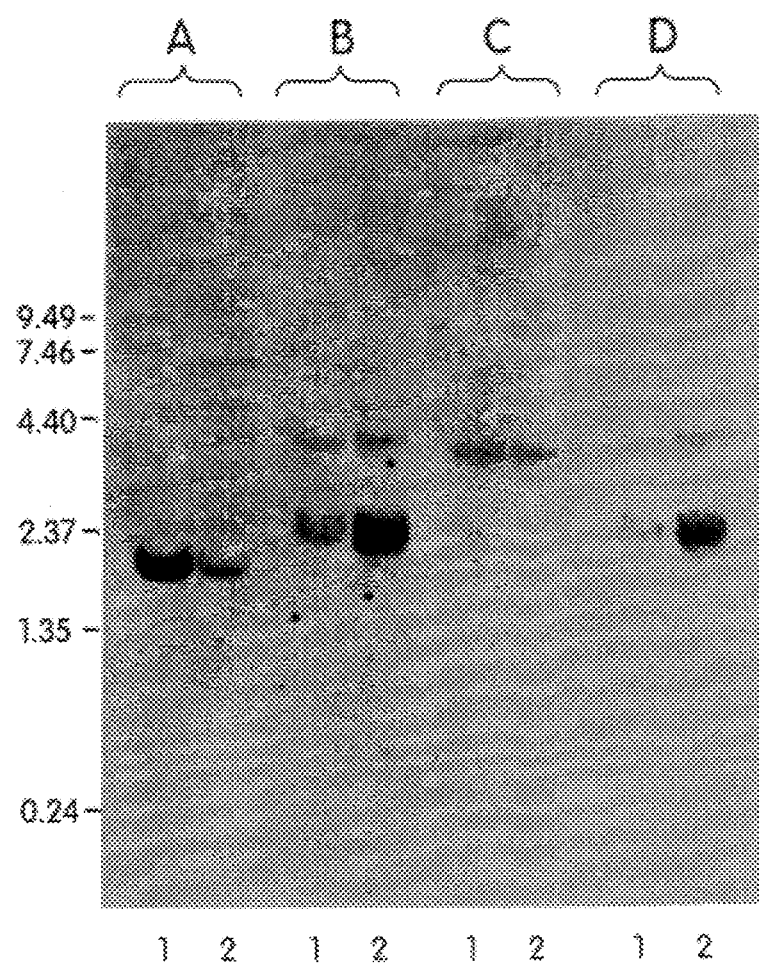
FIG. 2 shows results of Northern blot analysis of RNA using different OP-1-specific probes.
Figure 3:
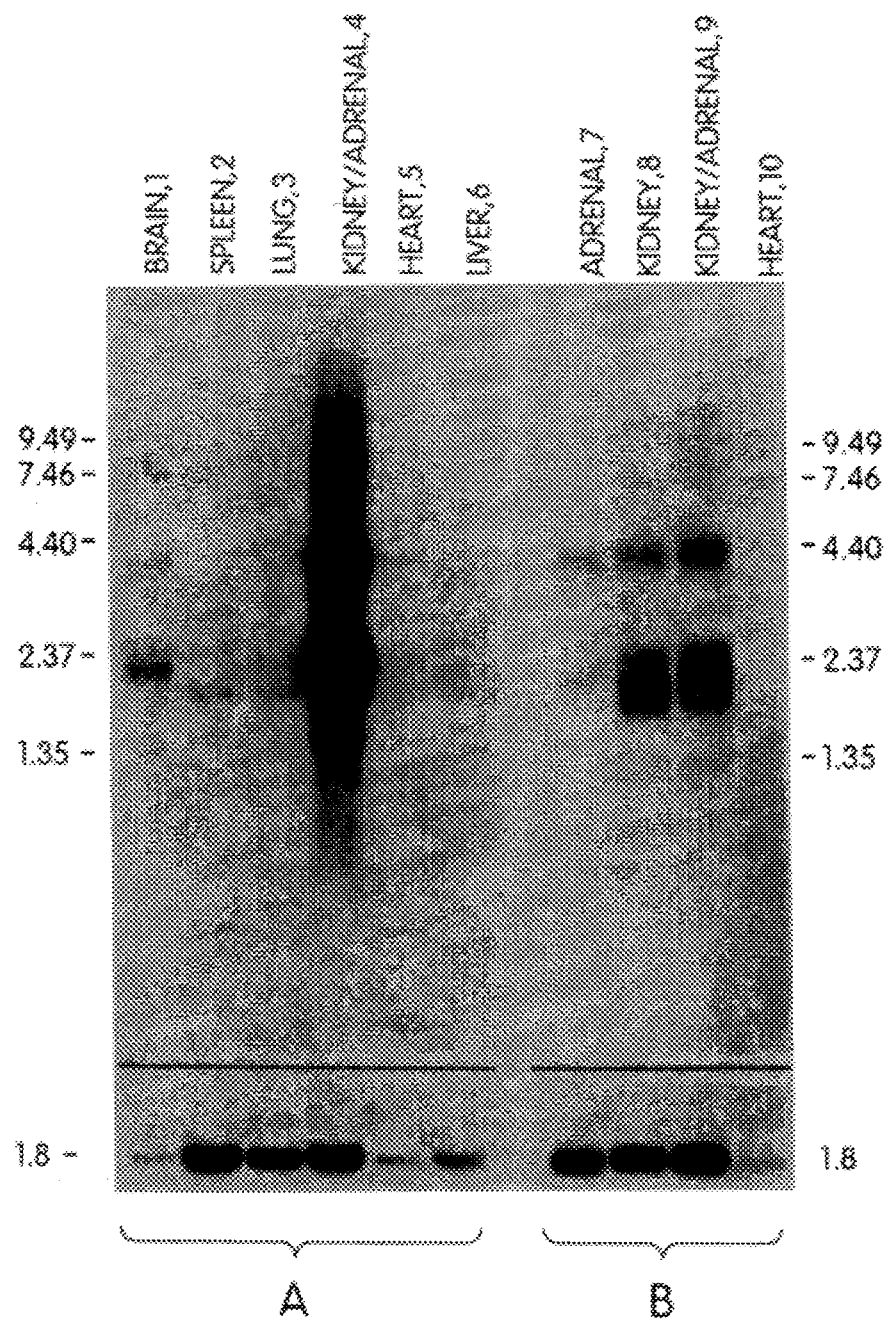
FIG. 3 shows results of Northern blot analysis of RNA from different cells types probed with an OP-1 probe.

Hybridization with a probe that covers approximately two thirds of the pro region (the 0.68 kb BstXI-BglI fragment), reveals a 4 kb message and 3 messages at 1.8 kb, 2.2 kb and 2.4 kb (FIG. 2B and D, and FIG. 3). In the Northern hybridization of FIG. 2, equal amounts (15 μg) of poly(A)$^+$ RNA were loaded into each lane, electrophoresed on a 1% agarose-formaldehyde gel, blotted and hybridized. A 0.24–9.49 kb RNA ladder (Bethesda Research Labs, Inc.) was used as size standard. The same filter was used for sequential hybridizations with labeled probes specific for OP-1 (Panels B and D), Vgr-1 (Panel C), and EF-Tu (Panel A). Panel A: the EF-Tu specific probe (a control) was the 0.4 kb HindIII-SacI fragment (part of the coding region), the SacI site used belonged to the vector; Panel B: the OP-1 specific probe was the 0.68 kb BstXI-BglI fragment (two thirds of the pro region and upstream sequences of the mature domain, not including any sequences from the 7-cysteine domain); Panel C: the Vgr-1 specific probe was the 0.26 kb PvuII-SacI fragment (part of the pro region and the amino-terminal sequences of the mature domain, including the first cysteine) (Lyons et al., 1989, Proc. Nat. Aca. Sci. 86: 4554, hereby incorporated by reference). Panel D: the OP-1 (3' flanking) specific probe was the 0.34 kb EarI-PstI fragment (3' untranslated sequences immediately following the sequences encoding OP-1).

In FIG. 3, the tissues to be used for RNA preparation were obtained from two week old mice (Panel A) or 5 week old mice (Panel B), with the exception of poly A+ RNA which was obtained from kidney adrenal gland of two week old mice (Panel B). Equal amounts of poly A+ RNA (15 μg for Panel A and 5 pg for Panel B) were loaded into each well. After electrophoresis (1.2% agarose-formaldehyde gels) and blotting, RNA was hybridized to the OP-1 specific 3' flanking probe described in the legend of FIG. 2 (Panel D). The 0.24-9.5 kb RNA ladder was used as size standard. The arrowheads indicate the OP-1 specific messages. The lower section of Panels A and B show the hybridization pattern obtained with the EF-Tu specific probe (a control).

Although the size of the Vgr-1 specific message is close to the 4 kb OP-1 species (FIG. 2 Panel C), the OP-1 4 kb mRNA is somewhat larger. To further rule out cross-hybridization with a non-OP-1 message, the 0.2 kb StuI-StuI fragment which represents the gene specific sequences immediately upstream of those encoding the 7-cysteine domain was used. This probe gave a hybridization pattern similar to the one shown in FIG. 2 Panel B (data not shown). A third probe, the 0.34 kb EarI-PstI fragment containing 3' untranslated sequences, also confirmed the pattern (FIG. 2 Panel D). Thus, the same four OP-1 specific messages were observed with three distinct probes.

The appearance of a new 4 kb OP-1 mRNA species was initially interpreted as cross hybridization of the OP-1 probe with Vgr-1 mRNA, which is approximately this size (FIG. 2 Panel C). However, the 4 kb message was detected with three different OP-1 specific probes, including one specific to the 3' untranslated region, and moreover it was separated from Vgr-1 message on the basis of size. Most likely, therefore, the 4 kb mRNA (and the three species of 1.8 kb, 2.2 kb and 2.4 kb) results from alternative splicing of OP-1 transcripts. The 4 kb OP-1 mRNA could also represent a bicistronic mRNA. The 4 kb message is a minor species in kidney, while it is more prominent in adrenal tissue.

The level of OP-1 expression was compared in different tissues using poly(A)$^+$ RNA prepared from brain, spleen, lung, kidney and adrenal gland, heart, and liver of 13 day post-natal mice. The RNA was analyzed on Northern blots by hybridization to various probes (FIG. 3. Equal amounts of mRNA, as judged by optical density, were fractionated on agarose formaldehyde gels. Ethidium bromide staining of the gels revealed some residual ribosomal RNA in addition to the mRNA and provided another assurance that the mRNA was not degraded and that there was not significant quantitative or qualitative variation in the preparation. As control for mRNA recovery, EF-Tu (translational elongation factor) mRNA was probed (assuming uniform expression of EF-Tu in most tissues). A great variation in the level of OP-1 expression was observed in spleen, lung, kidney and adrenal tissues whereas EF-Tu mRNA levels appeared relatively constant in these tissues (FIG. 3 Panel A). The highest level of OP-1 mRNA was found in the kidneys. Uniformly lower levels of EF-Tu mRNA were found in brain, heart and liver (FIG. 3 Panel A). Additional analysis of OP-1 mRNA showed the presence of significant amounts of OP-1 mRNA in the bladder (data not shown). In summary, next to kidney, bladder and adrenal tissue, brain tissue contained the highest levels of OP-1 RNA, whereas heart and liver did not give detectable signals.

OP-1 mRNA patterns display qualitative changes in the various tissues. Of the four messages found in brain, the 2.2 kb message is most abundant whereas in lung and spleen the 1.8 kb message predominates. Levels of the 1.8-2.4 kb in the kidney OP-1 mRNA are approximately two times higher in 3 day post-natal mice than in 17 day embryos, perhaps reflecting phases in bone and/or kidney development. mRNA was also prepared from carefully separated renal and adrenal tissues of 5 week old mice. Northern blot analysis (FIG. 3, Panel B) revealed that the high levels of 2.2 kb mRNA were derived from renal tissue whereas the 4 kb mRNA was more prominent in adrenal tissue.

The detection of of OP-1 message primarily in the kidney but also in bladder links OP-1 expression specifically with the urinary tract. Interestingly, the related Vgr-1 is also expressed at significant levels in kidney although its main site of expression in lung.

Once the tissue-specific expression of a given morphogen is known, cell types known to exist in that tissue or cell lines derived from that tissue can be screened, in a similar manner, to identify the cell type within that tissue that is actually responsible for the tissue specific synthesis and secretion of the morphogen. Once a cell type which produces the morphogen in an amount sufficient to detect increases or decreases in the production level of the morphogen upon exposure to a compound is identified, it may be used in tissue culture assay to rapidly screen for the ability of compound to upregulate or down regulate the synthesis and secretion of the morphogen. The level of morphogen production by the chosen cell type is determined with and without incubating the cell in culture with the compound, in order to assess the effects of the compound on the cell's ability to synthesize or secrete the morphogen. This can be accomplished by detection of the level of production of the morphogen either at the protein or mRNA level.

4. Growth of Cells in Culture

Cell cultures derived from kidney, adrenals, urinary bladder, brain, or other organs, may be prepared as described widely in the literature. For example, kidneys may be explanted from neonatal, new born, young or adult rodents (mouse or rat) and used in organ culture as whole or sliced (1-4 mm) tissues. Primary tissue cultures and established cell lines, also derived from kidney, adrenals, urinary, bladder, brain, or other tissues may be established in multiwell plates (6 well, 24 well, or 96 well) according to conventional cell culture techniques, and are cultured in the absence or presence of serum for a period of time (1-7 days). Cells may be cultured, for example, in Dulbecco's Modified Eagle medium (Gibco, Long Island, N.Y.) containing serum (e.g., fetal calf serum at 1%–10%, Gibco) or in serum-deprived medium, as desired, or in defined medium (e.g., containing insulin, transferrin, glucose, albumin, or other growth factors).

Samples for testing the level of morphogen production include culture supernatants or cell lysates, collected periodically and evaluated for OP-1 production by immunoblot analysis of a portion of the cell culture itself, collected periodically and used to prepare polyA+ RNA for RNA analysis (Sambrook et al., eds., *Molecular Cloning*, 1989, Cold Spring Harbor Press, Cold Spring Harbor, N.Y.). To monitor de novo OP-1 synthesis, some cultures are labeled with $^{35}$S-methionine/$^{35}$S-cysteine mixture for 6–24 hours and then evaluated for morphogen production by conventional immunoprecipitation methods (Sambrook et al., eds., *Molecular Cloning*, 1989, Cold Spring Harbor Press, Cold Spring Harbor, N.Y.). Alternatively, the production of morphogen or determination of the level of morphogen production may be ascertained using a simple assay for a parameter of cell growth, e.g., cellular proliferation or death. For example, where a morphogen is produced by a cultured cell line, the addition of antibody specific for the morphogen may result in relief from morphogen inhibition of cell growth. Thus, measurement of cellular proliferation can be used as an indication of morphogen production by a tissue.

5. Determination of Level of Morphogenic Protein

In order to quantitate the production of a morphogenic protein by a cell type, an immunoassay may be performed to detect the morphogen using a polyclonal or monoclonal antibody specific for that morphogen. For example, OP-1 may be detected using a polyclonal antibody specific for OP-1 in an ELISA, as follows.

1 µg/100 ul of affinity-purified polyclonal rabbit IgG specific for OP-1 is added to each well of a 96-well plate and incubated at 37° C. for an hour. The wells are washed four times with 0.16M sodium borate buffer with 0.15M NaCl (BSB), pH 8.2, containing 0.1% Tween 20. To minimize non-specific binding, the wells are blocked by filling completely with 1% bovine serum albumin (BSA) in BSB for 1 hour at 37° C. The wells are then washed four times with BSB containing 0.1% Tween 20. A 100 ul aliquot of an appropriate dilution of each of the test samples of cell culture supernatant is added to each well in triplicate and incubated at 37° C. for 30 min. After incubation, 100 ul biotinylated rabbit anti-OP-1 serum (stock solution is about 1 mg/ml and diluted 1:400 in BSB containing 1% BSA before use) is added to each well and incubated at 37° C. for 30 min. The wells are then washed four times with BSB containing 0.1% Tween 20. 100 ul strepavidin-alkaline (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5M Tris buffered Saline (TBS), pH 7.2. 50ul substrate (ELISA Amplification System Kit, Life Technologies, Inc., Bethesda, Md.) are added to each well incubated at room temperature for 15 min. Then, 50 ul amplifier (from the same amplification system kit) is added and incubated for another 15 min at room temperature. The reaction is stopped by the addition of 50 ul 0.3M sulphuric acid. The OD at 490 nm of the solution in each well is recorded. To quantitate OP-1 in culture media, a OP-1 standard curve is performed in parallel with the test samples.

6. Preparation of Polyclonal Antibody

Polyclonal antibody is prepared as follows. Each rabbit is given a primary immunization of 100 ug/500 ul E. coli-produced OP-1 monomer (amino acids 328-431 of SEQ. ID NO: 11) in 0.1% SDS mixed with 500 ul Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against OP-1 is detected in the serum using an ELISA assay. Then, the rabbit is boosted monthly with 100 ug of antigen and bled (15 ml per bleed) at days seven and ten after boosting.

7. Preparation of Monoclonal Antibody and Neutralizing Monoclonal Antibody

Monoclonal antibody specific for a given morphogen may be prepared as follows. A mouse is given two injections of E. coli produced OP-1 monomer (amino acids 328-431 in SEQ ID NO:11). The first injection contains 100ug of OP-1 in complete Freund's adjuvant and is given subcutaneously. The second injection contains 50 ug of OP-1 in incomplete adjuvant and is given intraperitoneally. The mouse then receives a total of 230 ug of OP-1 (amino acids 307-431 of SEQ ID NO:11) in four intraperitoneal injections at various times over an eight month period. One week prior to fusion, The mouse is boosted intraperitoneally with 100 ug of OP-1 (15-139) and 30 ug of the N-terminal peptide (Ser293-Asn309-Cys) conjugated through the added cys residue to bovine serum albumin with SMCC crosslinking agent. This boost is repeated five days (IP), four days (IP), three days (IP) and one day (IV) prior to fusion. The mouse spleen cells are then fused to myeloma (e.g., 653) cells at a ratio of 1:1 using PEG 1500 (Boehringer Mannheim), and the cell fusion is plated and screened for OP-1-specific antibodies using OP-1 (307-431) as antigen. The cell fusion and monoclonal screening are according to procedures widely available in the art. The neutralizing monoclonal is identified by its ability to block the biological activity of OP-1 when added to a cellular assay which responds biologically to added OP-1.

8. Identification of OP-1 Producing Cell Line Which Displays OP-1 Surface Receptors During the process of routinely testing the effects of increasing concentrations of OP-1 and TGF-β on the proliferation of various cell lines, a cell line was identified which, surprising, appears not only to synthesize and secrete OP-1, but also to display cell surface receptors to which the secreted OP-1 binds and acts to inhibit proliferation of the cells. This cell line was identified after the following observations. Addition of increasing concentrations of OP-1 or TGF-β failed to increase or decrease the relatively low basal rate of proliferation of the cells. However, addition of a monoclonal antibody, which neutralizes the activity of Op-1, resulted in a large increase in the proliferation of the cells. In addition, simultaneous addition of the same quantity of OP-1 neutralizing monoclonal to a fixed amount of OP-1 resulted in an increase in proliferation which was intermediate between the low basal level observed with OP-1 alone and the high level observed with the monoclonal alone. This cell line, which is an epithelial cell line that was derived from a bladder cell carcinoma, may be used in an assay of the invention. The parameter to be tested according to the invention is cellular proliferation. Thus, a compound(s) that increases or decreases the level of OP-1 production may be tested on this cell line as follows.

9. Assay for Identifying Drugs Which Affect OP-1Synthesis

A simple medium flux screening assay can be configured in a standard 24 or 96 well microtiter dishe, in which each well contains a constant number of a cell line having the characteristics described above. Increasing concentrations of an OP-1 neutralizing monoclonal antibody is added from left to right across the dish. A constant amount of different test substances is added from top to bottom on the dish. An increase in the synthesis and secretion of OP-1 (over its constitutive (non-induced) level) will be indicated by an increase in the amount of OP-1 neutralizing antibody required to release the cells from the antimitogenic activity of OP-1. A decrease in the synthesis and secretion of OP-1 (below its constitutive (repressed) level) will be indicated by the observation that decreased concentrations of the OP-1 neutralizing monoclonal antibody will be required to release the cells from the antimitogenic activity of OP-1. One of the major advantages of this assay is that the end point, i.e., the dilution of antibody which has an effect on cell proliferation, is a measure of mitosis, or an increase in the number of cells per well. Because several convenient and rapid assays exist for quantitating cell numbers, this assay is faster and requires significantly fewer steps to perform.

The assay may be performed as follows. After addition of appropriate concentrations of the OP-1 neutralizing monoclonal antibody and test substances to the wells containing the cells, the dishes are placed in an incubator at 37° C. for a period of 1-3 days. After completion of incubation/growth period, the dishes are removed and the cells in the individual wells are washed and stained with a vital stain, such as crystal violet. Washing and staining procedures are well-known in the art. The cells are then lysed and the stain dissolved in a constant amount of a solvent, such as ethanol. Quantitations of the dissolved stain, which is readily performed on an automated plate vendor, allows for direct quantitation of the number of cells in each well.

The above-described assay has the advantages of being rapid and easy to perform because it requires few steps. Another advantage is intrinsic to the assay; drugs which are screened according to this procedure that result in cell death (i.e., cytotoxic substances) are immediately, identifiable without the need of operator observation. In addition, although drugs that stop the growth of the cells (i.e., cytostatic substances) are scored as positive due to failure to see increases in cell numbers, they are automatically scored as suspect due to the failure of the highest concentrations of OP-1 neutralizing monoclonal antibody to release the cells from the antimitogenic activity of OP-1.

10. Candidate Drugs to Screen

The screening methods of the invention is used to test compounds for their effect on the production of morphogenic protein by a given cell type. Examples of compounds which may be screened include but are not limited to chemicals, biological response modifiers (e.g., lymphokines, cytokines, hormones, or vitamins), plant extracts, microbial broths and extracts medium conditioned by eukaryotic cells, body fluids, or tissue extracts.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method of screening a candidate compound for ability to modulate expression of a cellular gene encoding a protein comprising a naturally-occurring polypeptide, the amino acid sequence of said polypeptide comprising a sequence having at least 70% amino acid sequence homology with the C-terminal seven cysteine domain of human OP-1, residues 38 to 139 of SEQ ID No. 5, said protein having the property of inducing a developmental cascade of tissue-specific morphogenesis in a mammal, said method comprising the steps of:

(a) incubating a candidate compound with epithelial cells which express said cellular gene, for a time sufficient to allow said compound to modulate expression of said cellular gene and, (b) assaying said epithelial cells for the presence of or the amount of said protein expressed by said cellular gene, wherein a change in the level of said protein relative to the level thereof in said epithelial cells in the absence of said candidate compound is indicative of the ability of said compound to modulate expression of said cellular gene.

2. The method of claim 1 wherein the amino acid sequence of said polypeptide comprises a sequence defined by OPX, SEQ ID No. 29.

3. The method of claim 2 wherein said epithelial cells are cultured from brain or renal tissue.

4. The method of claim 2 wherein said epithelial cells are cultured from kidney, bladder or adrenal tissue.

5. The method of claim 1 wherein the presence of or the amount of said protein is assayed with an antibody selectively reactive with said naturally-occurring polypeptide.

6. The method of claim 1 wherein the presence of or the amount of said protein is assayed in step (b) by measuring cellular proliferation in cells which are sensitive to the concentration of said protein protein expressed by said cellular gene.

7. The method of claim 2 wherein said epithelial cells are epithelial carcinoma cells.

8. The method of claim 7 wherein said epithelial cells are an immortalized human bladder carcinoma cell line.

9. The method of claim 1 wherein the amino acid sequence of said naturally-occurring polypeptide comprises a sequence having at least 80% homology with the C-terminal seven cysteine domain of human OP-1, residues 38 to 139 of SEQ ID No. 5.

10. The method of claim 1 wherein the amino acid sequence of said naturally-occurring polypeptide comprises a sequence having at least 60% amino acid identity with the C-terminal seven cysteine domain of human OP-1, residues 38 to 139 of SEQ ID No. 5.

11. The method of claim 1 wherein the amino acid sequence of said naturally-occurring polypeptide comprises a sequence having at least 65% amino acid identity with the C-terminal seven cysteine domain of human OP-1, residues 38 to 139 of SEQ ID No. 5.

12. A method of screening a candidate compound for ability to modulate expression of a cellular gene encoding a protein comprising a naturally-occurring polypeptide, the amino acid sequence of said polypeptide comprising a sequence defined by Generic Sequence 6, SEQ ID No. 31, said protein having the property of inducing a developmental cascade of tissue-specific morphogenesis in a mammal, said method comprising the steps of:

incubating a candidate compound with epithelial cells which express said cellular gene, for a time sufficient to allow said compound to modulate expression of said cellular gene; and, (b) assaying said epithelial cells for the presence of or the amount of said protein expressed by said cellular gene, wherein a change in the level of said protein relative to the level thereof in said epithelial cells in the absence of said candidate compound is indicative of the ability of said compound to modulate expression of said cellular gene.

13. A method of screening a candidate compound for ability to modulate expression of a cellular gene encoding a naturally-occurring polypeptide, said polypeptide being selected from the group consisting of polypeptides depicted in Table II and naturally-occurring variants thereof, provided that any said variant when dimerized, forms a protein having the property of inducing a developmental cascade of tissue-specific morphogenesis in a mammal, said method comprising the steps of:

(a) incubating a candidate compound with epithelial cells which express said cellular gene, for a time sufficient to allow said compound to modulate expression of said cellular gene; and, (b) assaying said epithelial cells for the presence of or the amount of said naturally-occurring polypeptide, wherein a change in the level of said polypeptide relative to the level thereof in said epithelial cells in the absence of said candidate compound is indicative of the ability of said compound to modulate expression of said cellular gene.

14. The method of claim 13 wherein the presence of or the amount of said naturally-occurring polypeptide is determined using a nucleic acid probe that hybridizes, under stringent conditions, with RNA transcribed from said cellular gene.

15. The method of claim 14 wherein said nucleic acid probe hybridizes with an RNA transcript having a nucleic acid sequence encoding an amino acid sequence comprising at least residue 1 to residue 38 of human OP-1, SEQ ID No. 5.

16. The method of claim 14 wherein said nucleic acid probe hybridizes with an RNA transcript having a nucleic acid sequence which corresponds to an untranslated non-coding sequence downstream from the 3' terminus of a nucleic acid sequence encoding human OP-1, SEQ ID No. 5.

* * * * *

UNITED STATES PATENT AND TRADEMARK OFFICE
CERTIFICATE OF CORRECTION

PATENT NO. : 5,650,276
DATED : July 22, 1997
INVENTOR(S) : Smart et al.

It is certified that error appears in the above-identified patent and that said Letters Patent is hereby corrected as shown below:

Title page, line 5, before "which" insert --Aug. 30, 1991, abandoned,--; and after "667,274" insert --March 11, 1991, abandoned, 752,764, Aug. 30 1991, which is a continuation-in-part of 667,274, March 11, 1991, abandoned--.
Item [56] other publications
page 1, col. 1, line 35, delete "Piqueras" and insert --Paredes--.
page 1, col. 1, line 48, delete "Collogen" and insert --Collagen--.
page 1, col. 2, line 6, delete "Nat.Aca." and insert --Natl. Acad. --.
page 1, col. 2, line 38, delete the line in it's entirety.
Title page,
Abstract, line 3, delete "system" and insert --systems--.
Abstract, line 5, delete "phognic" and insert --phogen--.
page 2, col. 1, line 3, delete "2" and insert --3--.
page 2, col. 1, line 5, delete "Research" and insert --Research--.
page 2, col. 1, line 9, after "(004" insert a closed paren --)--.
page 2, col. 1, line 10, after "Biophy" insert --s--.
col. 15, line 8, after "morphogenic" insert an --s--.
col. 15, line 11, after "tissue" insert an --s--.
col. 86, line 59, after "assayed" insert --in step (b)--.
col. 86, line 64, delete "protein" (2nd occurrence).
col. 87, line 26, before "incubating" insert (a).

Signed and Sealed this

Twenty-third Day of March, 1999

Attest:

Q. TODD DICKINSON

Attesting Officer

Acting Commissioner of Patents and Trademarks